US009655920B2

(12) United States Patent
Connor et al.

(10) Patent No.: US 9,655,920 B2
(45) Date of Patent: May 23, 2017

(54) AMINE POLYMERS FOR USE AS BILE ACID SEQUESTRANTS

(75) Inventors: Eric Connor, Los Gatos, CA (US); Kalpesh Biyani, Newark, CA (US); Scott Hecker, Del Mar, CA (US); Inez Lees, Mountain View, CA (US); Paul Mansky, San Francisco, CA (US); YongQi Mu, Los Altos, CA (US); Faleh Salaymeh, Sunnyvale, CA (US); Hongmin Zhang, Fremont, CA (US); David Bergbreiter, College Station, TX (US); Grace Huynh, San Francisco, CA (US); Michael James Cope, Berkeley, CA (US); Elizabeth Goka, San Jose, CA (US); Angela Lee, San Jose, CA (US); Deidre Madsen, Sunnyvale, CA (US); Jun Shao, Fremont, CA (US); Xinnan Zhang, Campbell, CA (US)

(73) Assignee: Relypsa, Inc., Redwood City, CA (US)

( * ) Notice: Subject to any disclaimer, the term of this patent is extended or adjusted under 35 U.S.C. 154(b) by 1276 days.

(21) Appl. No.: 13/581,148

(22) PCT Filed: Feb. 24, 2011

(86) PCT No.: PCT/US2011/026106
§ 371 (c)(1),
(2), (4) Date: Aug. 20, 2014

(87) PCT Pub. No.: WO2011/106548
PCT Pub. Date: Sep. 1, 2011

(65) Prior Publication Data
US 2014/0356316 A1 Dec. 4, 2014

Related U.S. Application Data

(60) Provisional application No. 61/307,822, filed on Feb. 24, 2010, provisional application No. 61/307,820, filed on Feb. 24, 2010, provisional application No. 61/373,682, filed on Aug. 13, 2010.

(51) Int. Cl.
*A61K 31/785* (2006.01)
*C08G 73/02* (2006.01)
*A61K 45/06* (2006.01)

(52) U.S. Cl.
CPC ............ *A61K 31/785* (2013.01); *A61K 45/06* (2013.01); *C08G 73/02* (2013.01); *C08G 73/0206* (2013.01)

(58) Field of Classification Search
None
See application file for complete search history.

(56) References Cited

U.S. PATENT DOCUMENTS

| 3,692,895 A | 9/1972 | Nelson et al. |
|---|---|---|
| 5,428,112 A | 6/1995 | Ahlers et al. |
| 5,430,110 A | 7/1995 | Ahlers et al. |
| 6,294,163 B1 | 9/2001 | Dhal et al. |
| 6,365,186 B1 * | 4/2002 | Huval et al. ................. 424/486 |
| 6,383,500 B1 | 5/2002 | Wooley et al. |
| 2005/0131138 A1 | 6/2005 | Connor et al. |
| 2005/0147580 A1 | 7/2005 | Connor et al. |
| 2005/0209423 A1 | 9/2005 | Chang et al. |

FOREIGN PATENT DOCUMENTS

| EP | 1 840 127 A1 | 3/2007 |
|---|---|---|
| WO | 94/04596 A1 | 3/1994 |
| WO | 00/38664 A2 | 7/2000 |
| WO | 2005/041902 A2 | 5/2005 |
| WO | 2005/065291 A2 | 7/2005 |
| WO | 2005/092039 A2 | 10/2005 |
| WO | 2007/130463 A2 | 11/2007 |
| WO | 2008/011047 A2 | 1/2008 |
| WO | 2008/027551 A2 | 3/2008 |
| WO | 2008/076242 A1 | 6/2008 |
| WO | 2008/103368 A1 | 8/2008 |
| WO | 2008/133954 A1 | 11/2008 |
| WO | 2009/097127 A1 | 8/2009 |
| WO | 2009/122400 A1 | 10/2009 |
| WO | 2009/158625 A2 | 12/2009 |
| WO | 2011/106542 A2 | 9/2011 |
| WO | 2011/106545 A1 | 9/2011 |

OTHER PUBLICATIONS

Davidson et al., "Colesevelam hydrochloride: a non-absorbed, polymeric cholesterol-lowering agent", 2000, Exp. Opin. Invest. Drugs, vol. 9(11), pp. 2663-2671.*
Bell, D. S. H., et al., "Rediscovering Bile Acid Sequestrants," Diabetes, Obesity and Metabolism, 2009, 8 Pages, vol. 11, No. 12.
Huval, C. C., et al., "Ammonium and Guanidinium Functionalized Hydrogels as Bile Acid Sequestrants: Synthesis, Characterization, and Biological Properties," Journal of Macromolecular Science, 2004, pp. 231-244, vol. 41, No. 3, Abstract only.
Huval, C. C., et al., "Syntheses of Hydrophobically Modified Cationic Hydrogels by Copolymerization of Alkyl Substituted Diallylamine Monomers and Their Use as Bile Acid Sequestrants," European Polymer Journal, 2004, pp. 693-701, vol. 40.
Qian, L., et al., "Modified Guanidine Polymers: Synthesis and Antimicrobial Mechanism Revealed by AFM," Polymer, 2008, pp. 2471-2475, vol. 49.
Shang, Q., et al., "Colesevelam Improves Insulin Resistance in a Diet-Induced Obesity (F-DIO) Rat Model by Increasing the Release of GLP-1," American Journal of Physiology. Gastrointestinal and Liver Physiology, 2009, pp. G419-G424, vol. 298, No. 3.

(Continued)

*Primary Examiner* — Robert A Wax
*Assistant Examiner* — Randeep Singh
(74) *Attorney, Agent, or Firm* — Senniger Powers LLP

(57) ABSTRACT

The present invention provides crosslinked amine polymers effective for binding and removing bile salts from the gastrointestinal tract. These bile acid binding polymers or pharmaceutical compositions thereof can be administered to subjects to treat various conditions, including hypercholesteremia, diabetes, pruritus, irritable bowel syndrome-diarrhea (IBS-D), bile acid malabsorption, and the like.

17 Claims, 4 Drawing Sheets

(56) References Cited

OTHER PUBLICATIONS

Suwa, K., et al., "Synthesis and Functionalities of Poly(N-Vinylalkylamide). VI. A Novel Thermosensitive Hydrogel Crosslinked Poly(N-Vinylisobutyramide)," Journal of Polymer Science: Part A: Polymer Chemistry, 1997, pp. 3377-3384, vol. 35, No. 15.
Worner, C., et al., "Polynitrile- and Polyamine-Functional Poly(trimethylene imine) Dendrimers," Angewandte Chemie International Edition in English, Sep. 1993, pp. 1306-1308, vol. 32, No. 9.
Yamamoto, K., et al., "Synthesis and Functionalities of Poly(N-vinylalkylamide). 13. Synthesis and Properties of Thermal and pH Stimuli-Responsive Poly(vinylamine) Copolymers," Macromolecules, 2001, pp. 8014-8020, vol. 34, No. 23.
Database Reaxys, XP-002637512, Retrieved from EPOQUE, Database Accession No. 7725121, May 6, 2011, 2 pages.
Database Registry, Chemical Abstracts Service, XP-002642310, Retrieved from STN, Database Accession No. 870121-81-6, Dec. 16, 2005, 1 page.
Database Registry, Chemical Abstracts Service, XP-002637513, Retrieved from STN, Database Accession No. 870121-87-2, Dec. 16, 2005, 1 page.

\* cited by examiner

AMINE POLYMERS FOR USE AS BILE ACID SEQUESTRANTS

FIELD OF THE INVENTION

The present invention generally relates to amine polymers useful to bind bile acids in the gastrointestinal tract of a patient in need of bile acid removal. These polymers and pharmaceutical compositions thereof are useful to lower cholesterol, particularly, non-high density lipoprotein (non-HDL), or more particularly, low-density lipoprotein (LDL) cholesterol, in patients in need thereof.

BACKGROUND OF THE INVENTION

Cholesterol is used by the body as a structural component of cell membranes. In addition, it is a basic building block for the production of many hormones, adrenal steroids, vitamin D and bile acids. Elevated levels of cholesterol carried in particles of low density lipoprotein cholesterol (LDL-C), or less specifically, cholesterol not carried in particles of high-density cholesterol (non HDL-C) are associated with an increased risk of coronary heart disease. A direct link between high blood cholesterol and cardiovascular disease (CVD) has been confirmed for both non-statin and statin trials, consistent with a direct relationship between LDL-C lowering and CVD reduction. These studies as well as many others have led to recommendations by health authorities for lowering elevated total cholesterol and LDL-C levels.

Bile acids are amphipathic detergents with micelle-forming properties that are synthesized in the liver from cholesterol and solubilize lipids to aid in their uptake from the gastrointestinal lumen. Common bile acids found in man include unconjugated bile acids (for example cholic acid, chenodeoxycholic acid, deoxycholic acid, lithocholic acid) and conjugated bile acids (for example taurocholic acid, glycocholic acid, glycochenodeoxycholic acid, taurochenodeoxycholic acid, glycodeoxycholic acid, taurodeoxycholic acid, glycolithocholic acid, and taurolithocholic acid). After a meal, bile acids are released by the gall bladder. At ileal pH, the bile acids are predominantly deprotonated and are in their salt form. The majority of bile acids are reabsorbed, primarily by active transport in the distal ileum, with elimination in the feces being the primary route of cholesterol excretion.

A bile acid sequestrant can bind bile acids to prevent reabsorption of the bile acids and cause more of the bile acids to be excreted in the stool. The sequestrant reduces the amount of bile acids reabsorbed by the intestine and subsequently transported to the liver. To compensate for this disruption in enterohepatic circulation and consequent reduction of the endogenous bile acid pool, hepatic cholesterol 7-alpha-hydroxylase is upregulated. This results in additional conversion of cholesterol into bile acids, thereby restoring the bile acid pool. Upregulation of cholesterol conversion to bile acids also involves a cascade of signaling that results in up-regulation of liver LDL-receptors and consequent lowering of serum LDL-C levels, amongst other effects.

Existing bile acid sequestrants do not reduce the serum LDL-cholesterol concentration enough without requiring the patient to take either large amounts of the sequestrant or another drug that is combined with the sequestrant (e.g., statins). These reduce patient compliance and tolerance. Thus, bile acid sequestrants capable of more effectively removing bile salts from the gastrointestinal tract with equal or lower doses are needed.

SUMMARY OF THE INVENTION

The present invention provides an amine polymer that is effective for binding and removing bile salts from the gastrointestinal tract.

One aspect of the invention is an amine polymer that comprises repeat units derived from polymerization of an amine monomer having six, seven or eight possible reaction sites and a crosslinking monomer having two or three possible reaction sites, wherein the molar ratio of the amine monomer to the crosslinking monomer is in the range of from 1:3 to about 1:1.1, and the amine polymer has a binding affinity for bile acids of at least 0.46 mmol/g when measured using an in vitro A assay.

Another aspect is an amine polymer comprising the reaction product of an amine monomer having six, seven or eight possible reaction sites and a crosslinking monomer, wherein units of the polymer have the structure of formula 1

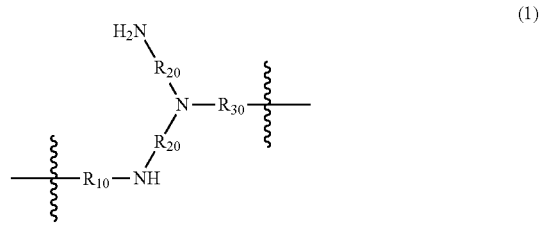

wherein $R_{10}$ is derived from the crosslinking monomer and is $C_2$ to $C_{16}$ alkylene, —NH—C(NH)—NH—, —NH—C($NH_2^+$)—NH—, or $C_2$ to $C_{50}$ alkylene wherein one or more of the —$CH_2$— groups of the alkylene group is replaced with an amide, a carbonyl, an ether, an ester, a cycloalkyl, or a heterocyclo functional group, or one or more of the —$CH_2$— groups of the alkylene group is substituted with hydroxy; $R_{30}$ is derived from the amine monomer and is $C_2$ to $C_{12}$ alkylene, arylene, diformylheterocyclo, or $C_2$ to $C_{12}$ alkylene wherein one or more of the —$CH_2$— groups of the alkylene group is replaced with an amide, a carbonyl, a cycloalkyl, an aryl, or a heterocyclo functional group; each $R_{20}$ is independently $C_2$ to $C_6$ alkylene or $C_2$ to $C_6$ alkylene wherein one or more of the —$CH_2$— groups of the alkylene group is replaced with an amide functional group; and at least one of $R_{10}$ or $R_{30}$ is a hydrophobic group having a calculated log P (c Log P) of greater than 4.

A further aspect is an amine polymer that comprises the reaction product of an amine monomer having six, seven or eight possible reaction sites and a crosslinking monomer wherein units of the polymer have the general structure of formula 1 wherein $R_{10}$ is derived from the crosslinking monomer and is $C_2$ to $C_{16}$ alkylene, —NH—C(NH)—NH—, —NH—C($NH_2^+$)—NH—, or $C_2$ to $C_{50}$ alkylene wherein one or more of the —$CH_2$— groups of the alkylene group is replaced with an amide, a carbonyl, an ether, an ester, a cycloalkyl, or a heterocyclo functional group, or one or more of the —$CH_2$— groups of the alkylene group is substituted with hydroxy; $R_{30}$ is derived from the amine monomer and is $C_2$ to $C_6$ alkylene; each $R_{20}$ is independently $C_2$ to $C_6$ alkylene or $C_2$ to $C_6$ alkylene wherein one or more of the —$CH_2$— groups of the alkylene group is replaced with an amide functional group; and $R_{10}$ is a hydrophobic group having a calculated log P (c Log P) of greater than 4.

Yet another aspect is an amine polymer that comprises the reaction product of an amine monomer having six, seven or eight possible reaction sites and a crosslinking monomer wherein units of the polymer have the general structure of formula 1 wherein $R_{10}$ is derived from the crosslinking monomer and is $C_8$ to $C_{16}$ alkylene, or $C_8$ to $C_{50}$ alkylene wherein one or more of the —$CH_2$— groups of the alkylene group is replaced with an amide, a carbonyl, an ether, an ester, a cycloalkyl, an aryl, or a heterocyclo functional group; $R_{30}$ is derived from the amine monomer and is $C_2$ to $C_{12}$ alkylene, arylene, diformylheterocyclo, or $C_2$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; and each $R_{20}$ is independently $C_2$ to $C_6$ alkylene or $C_2$ to $C_6$ alkylene wherein one or more of the —$CH_2$— groups of the alkylene group is replaced with an amide functional group.

Yet another aspect of the another aspect is an amine polymer that comprises the reaction product of an amine monomer having six, seven or eight possible reaction sites and a crosslinking monomer wherein units of the polymer have the general structure of formula 1 wherein $R_{10}$ is derived from the crosslinking monomer and is $C_2$ to $C_6$ alkylene, or $C_2$ to $C_6$ alkylene wherein one or more of the —$CH_2$— groups of the alkylene group is replaced with an amide, a carbonyl, an ether, an ester, a cycloalkyl, an aryl, or a heterocyclo functional group, or one or more of the —$CH_2$— groups of the alkylene group is substituted with hydroxy; $R_{30}$ is derived from the amine monomer and is $C_8$ to $C_{16}$ alkylene, arylene, diformylheterocyclo, or $C_8$ to $C_{16}$ alkylene wherein one or more of the —$CH_2$— groups of the alkylene group is replaced with an amide, a carbonyl, an ether, an ester, a cycloalkyl, an aryl, or a heterocyclo functional group, or one or more of the —$CH_2$— groups of the alkylene group is substituted with hydroxy; and each $R_{20}$ is independently $C_2$ to $C_6$ alkylene or $C_2$ to $C_6$ alkylene wherein one or more of the —$CH_2$— groups of the alkylene group is replaced with an amide functional group.

A further aspect of the invention is an amine polymer that comprises the reaction product of an amine monomer having six, seven or eight possible reaction sites and a crosslinking monomer having two or three possible reaction sites, wherein the polymer is insoluble in water, at least some of said amine secondary nitrogen atoms are part of a cross-linked polymer network, and the crosslinking monomer is a hydrophobic group having a calculated log P (c Log P) of greater than 4; and the crosslinking monomer is a compound having the formula X—$R_1$—X, wherein each X is independently a leaving group, and $R_1$ is $C_8$ to $C_{50}$ alkylene or $C_8$ to $C_{50}$ alkylene wherein one or more of the —$CH_2$— groups of the alkylene group is replaced with an amide, a carbonyl, an ether, an ester, a cycloalkyl, an aryl, or a heterocyclo functional group.

Yet a further aspect of the invention is an amine polymer that comprises the reaction product of an amine monomer having six, seven or eight possible reaction sites and a crosslinking monomer having two or three possible reaction sites, wherein the polymer is insoluble in water, at least some of said amine secondary nitrogen atoms are part of a crosslinked polymer network, and the amine monomer has at least one segment that is a $C_8$ to $C_{16}$ alkylene, arylene, or $C_8$ to $C_{50}$ alkylene wherein one or more of the —$CH_2$— groups of the alkylene group is replaced with an amide, a carbonyl, an ether, an ester, a cycloalkyl, an aryl, or a heterocyclo functional group, and the segment has a calculated log P (c Log P) of greater than 4; and the crosslinking monomer is a compound having the formula X—$R_1$—X, wherein each X is independently a leaving group, and $R_1$ is $C_2$ to $C_6$ alkylene, or $C_2$ to $C_6$ alkylene wherein one or more of the —$CH_2$— groups of the alkylene group is replaced with an amide, a carbonyl, an ether, an ester, a cycloalkyl, an aryl, or a heterocyclo functional group, or one or more of the —$CH_2$— groups of the alkylene group is substituted with hydroxy.

Another aspect is an amine polymer that comprises repeat units derived from polymerization of an amine monomer having six, seven or eight possible reaction sites and a crosslinking monomer having two or three possible reaction sites, wherein the molar ratio of the amine monomer to the crosslinking monomer is in the range of from 1:3 to about 1:1, and wherein: the polymer binds phosphate in vitro in an amount of less than 0.3 mmol/gram of polymer when measured using a B assay; and the polymer binds bile acids with an in vitro capacity of greater than about 3 mmol/gram of polymer when measured using a B assay.

Yet another aspect is an amine polymer comprising units of the polymer having nodes of positive charge separated by aliphatic segments, wherein the nodes of positive charge have a charge density of at least 19.0 mEq/g and a molecular weight of at least 200.0 g/mol and at least one aliphatic segment is bonded to each node of positive charge, the at least one aliphatic segment having a calculated log P (c Log P) greater than 4 and wherein each of the nodes of positive charge does not contain an aliphatic segment having a calculated log P (c Log P) greater than 4.

A further aspect is an amine polymer comprising units of the polymer having nodes of positive charge separated by aliphatic segments, wherein the nodes of positive charge have a charge density greater than 17.3 mEq/g and the structure of formula A

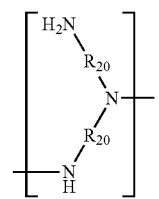

each $R_{20}$ being independently $C_3$ to $C_8$ alkylene or $C_3$ to $C_8$ alkylene wherein one or more of the —$CH_2$— groups of the alkylene group is replaced with an amide functional group; and wherein at least one aliphatic segment is bonded to each node of positive charge, each aliphatic segment having a calculated log P (c Log P) greater than 4.

Yet another aspect is an amine polymer comprising units of the polymer having the structure of formula 1 wherein $R_{10}$ is $C_2$ to $C_{16}$ alkylene, arylene, —NH—C(NH)—NH—, —NH—C($NH_2^+$)—NH—, dimethylbiphenyl, or $C_2$ to $C_{50}$ alkylene wherein one or more of the —$CH_2$— groups of the alkylene group is replaced with an amide, a carbonyl, an ether, an ester, a cycloalkyl, an aryl, or a heterocyclo functional group, or one or more of the —$CH_2$— groups of the alkylene group is substituted with hydroxy; $R_{30}$ is $C_2$ to $C_{12}$ alkylene, arylene, diformylheterocyclo, or $C_2$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; and each $R_{20}$ is independently $C_2$ to $C_8$ alkylene or $C_2$ to $C_8$ alkylene wherein one or more of the —$CH_2$— groups of the alkylene group is replaced with an amide functional group; the polymer binds phosphate in vitro in an amount of less than 0.3 mmol/gram of polymer when measured using a B assay; and the polymer binds bile acids with an in vitro capacity of greater than about 3 mmol/gram of polymer when measured using a B assay.

Another aspect is an amine polymer that comprises repeat units derived from polymerization of an amine monomer and a crosslinking monomer, wherein the amine monomer is an amine of formula 2 having the structure:

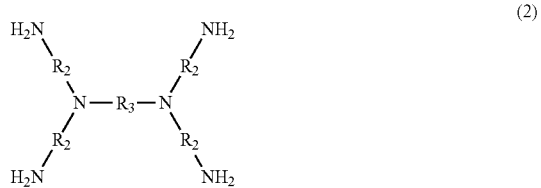

(2)

wherein each $R_2$ is independently $C_2$ to $C_8$ alkylene or $C_2$ to $C_8$ alkylene wherein one or more of the —$CH_2$— groups of the alkylene group is replaced with at least one amide functional group, and $R_3$ is $C_2$ to $C_{12}$ alkylene, arylene, diformylheterocyclo, or $C_2$ to $C_8$ alkylene wherein one or more of the —$CH_2$— groups of the alkylene group is replaced with an amide, a carbonyl, an ether, an ester, a cycloalkyl, an aryl, or a heterocyclo functional group; and the crosslinking monomer is guanidine, a guanidinium salt, a compound having the formula X—$R_1$—X, or a combination thereof, wherein each X is independently a leaving group, $R_1$ is $C_8$ to $C_{16}$ alkylene, or $C_5$ to $C_{50}$ alkylene wherein one or more of the —$CH_2$— groups of the alkylene group is replaced with an amide, a carbonyl, an ether, an ester, a cycloalkyl, an aryl, or a heterocyclo functional group.

Yet another aspect is an amine polymer derived from polymerization of an amine monomer and a crosslinking monomer wherein the amine monomer is an amine of formula 3 having the structure:

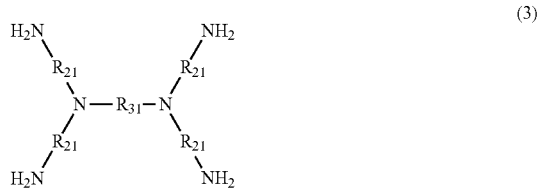

(3)

wherein each $R_{21}$ is independently $C_2$ to $C_8$ wherein one or more of the —$CH_2$— groups of the alkylene group is replaced with at least one sulfur atom, and $R_{31}$ is $C_2$ to $C_{12}$ alkylene, arylene, diformylheterocyclo, or $C_2$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; and the crosslinking monomer is guanidine, a guanidinium salt, a compound having the formula X—$R_1$—X, or a combination thereof, wherein each X is independently a leaving group, and $R_1$ is $C_2$ to $C_{16}$ alkylene, arylene, dimethylbiphenyl, or $C_2$ to $C_{50}$ alkylene wherein one or more of the —$CH_2$— groups of the alkylene group is replaced with an amide, a carbonyl, an ether, an ester, a cycloalkyl, an aryl, or a heterocyclo functional group, or one or more of the —$CH_2$— groups of the alkylene group is substituted with hydroxy.

A further aspect is an amine polymer that comprises repeat units derived from polymerization of an amine monomer of formula 2 and a crosslinking monomer, wherein each $R_2$ is independently $C_2$ to $C_8$ alkylene or $C_2$ to $C_8$ alkylene wherein one or more of the —$CH_2$— groups of the alkylene group is replaced with an amide functional group; and $R_3$ is $C_2$ to $C_{12}$ alkylene, arylene, diformylheterocyclo, or $C_2$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; and a portion of the nitrogen atoms of the amine polymer are substituted with a ligand selected from aminoalkyl, aryl, arylalkyl, oxoalkyl, cycloalkyl, (cycloalkyl)alkyl, guanidino, heterocyclo, heterocyloalkyl, (trialkylammonio)alkyl, 2-(protected amino)-m-(heterocyclo)-1-oxo$C_m$alkyl, 2-(protected amino)-1-oxo$C_m$alkyl, 2-(protected amino)-3-methyl-1-oxo$C_m$alkyl, 2-(protected amino)-4-methyl-1-oxo$C_m$alkyl, 2-(protected amino)-1-oxo-m-aryl$C_m$alkyl, 2-(protected amino)-m-(alkylthio)-1-oxo$C_m$alkyl, 2-(protected amino)-m-(aryl)-1-oxo$C_m$alkyl, 2-(protected amino)-m-carboxy-1-oxo$C_m$alkyl, 2-(protected amino)-m-guanidino-1-oxo$C_m$alkyl, 2-(protected amino)-(m−1)-hydroxy-1-oxo$C_m$alkyl, 2-(protected amino)-m-hydroxy-1-oxo$C_m$alkyl, 2-(protected amino)-m-mercapto-1-oxo$C_m$alkyl, m-(alkylamino)-m-oxo$C_m$alkyl, m-(alkylheterocyclo)$C_m$alkyl, m-amino-2-(protected amino)-1-oxo$C_m$alkyl, m-amino-2-(protected amino)-1,m-dioxo$C_m$alkyl, m-(x-amino$C_x$alkyl)heterocyclo$C_m$alkyl, (m−1)-amino-m-(heterocyclo)-1-oxo$C_m$alkyl, m-(arylalkylamino)-m-oxo$C_m$alkyl, m-(x-(alkylthio)$C_x$alkylamino)-m-oxo$C_m$alkyl, m-(x-amino$C_x$alkylamino)-m-oxo$C_m$alkyl, m-(x-amino-x-oxo$C_x$alkylamino)-m-oxo$C_m$alkyl, m-(x-carboxy$C_x$alkylamino)-m-oxo$C_m$alkyl, m-(heterocycloalkylamino)-m-oxo$C_m$alkyl, m-(x-hydroxy$C_x$alkylamino)-m-oxo$C_m$alkyl, m-((x−1)-hydroxy$C_x$alkylamino)-m-oxo$C_m$alkyl, m-(x-mercapto$C_x$alkylamino)-m-oxo$C_m$alkyl, m-(x-trialkylammonio$C_x$alkyl)heterocyclo$C_m$alkyl, m-(x-(2-(alkoxy)benzamido)$C_x$alkylamino)-m-oxo$C_m$alkyl, m-(x-(3-(alkoxy)benzamido)$C_x$alkylamino)-m-oxo$C_m$alkyl, m-(x-(4-(alkoxy)benzamido)$C_x$alkylamino)-m-oxo$C_m$alkyl, a ligand of formula 4

*—$R_{46}$—$R_{47}$—$R_{48}$ (4)

or a combination thereof, wherein $R_{46}$ is $C_6$ to $C_{16}$ alkylene, $R_{47}$ is 1,y-bis(1-methylpiperidin-4-yl)$C_y$alkylene, $R_{48}$ is $C_6$ to $C_{16}$ alkyl, m is an integer from 3 to 12, x is an integer from 1 to 12, y is an integer from 1 to 14, and z is an integer from 1 to 16.

Another aspect of the invention is an amine of formula 6 having the structure:

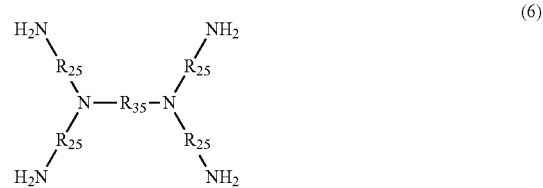

(6)

wherein each $R_{25}$ is independently $C_2$ to $C_8$ alkylene or $C_2$ to $C_8$ alkylene wherein one or more of the —$CH_2$— groups of the alkylene group is replaced with at least one amide functional group, and $R_{35}$ is $C_8$ to $C_{16}$ alkylene, or $C_8$ to $C_{16}$ alkylene wherein one or more of the —$CH_2$— groups of the alkylene group is replaced with an amide, a carbonyl, an ether, an ester, a cycloalkyl, an aryl, or a heterocyclo functional group.

Yet a further aspect is an amine polymer useful as a bile acid sequestrant, wherein, in a buffer solution at 37° C. containing less than 2.6 mM taurocholic acid, the amine polymer binds more of the acid than sevelamer and in a buffer solution at 37° C. containing more than 5.0 mM taurocholic acid the amine polymer binds more bile acid that colesevelam.

Other objects and features will be in part apparent and in part pointed out hereinafter.

DESCRIPTION OF THE PREFERRED EMBODIMENTS

Figure 1A:
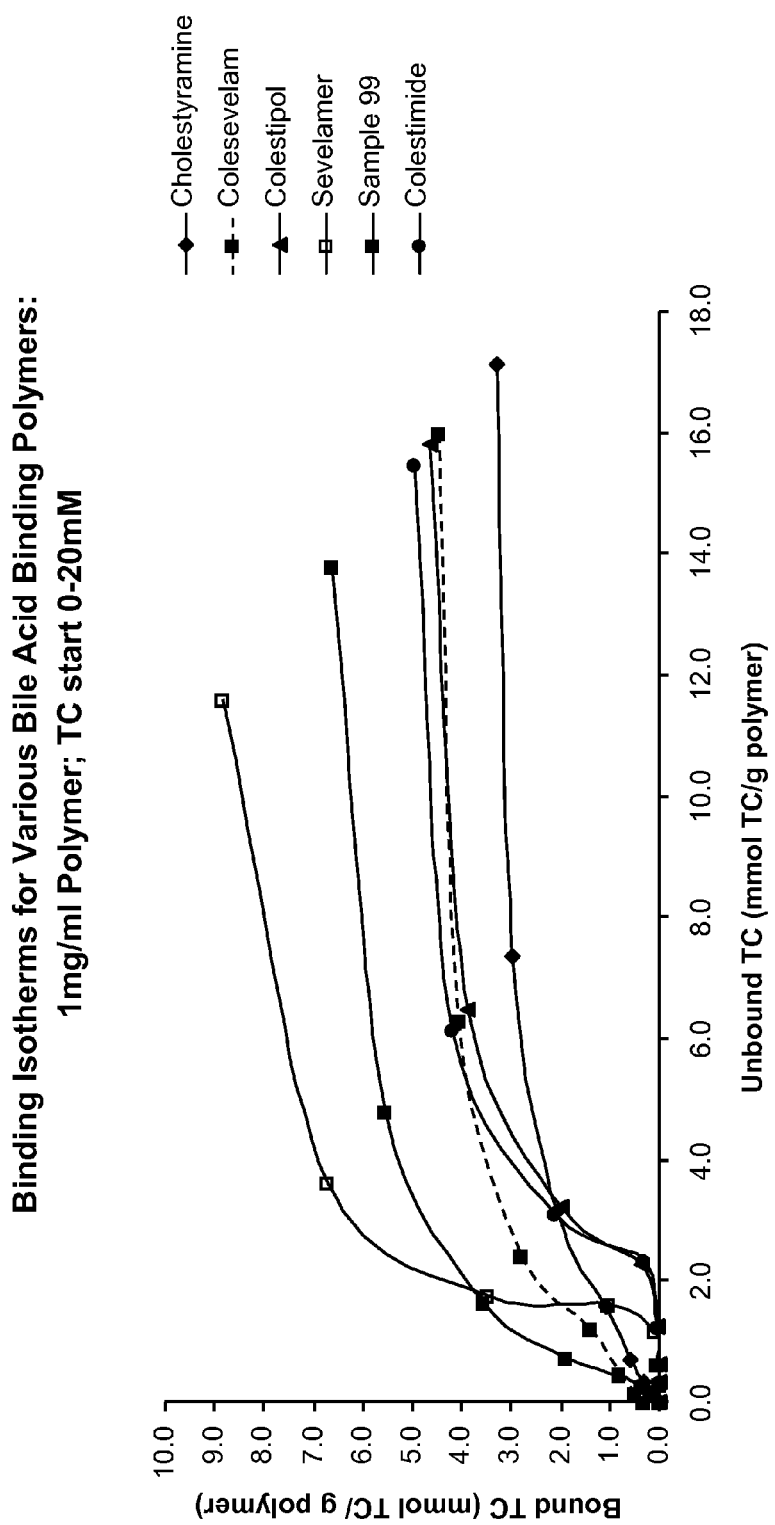
FIG. 1A is a graph of the unbound taurocholic acid concentration versus the bound taurocholic acid concentration for various bile acid binders at taurocholic acid concentrations up to 20 mM.

The present invention is an amine polymer useful for binding bile salts, pharmaceutical compositions comprising the amine polymer, and methods of treating hypercholesterolemia, diabetes or other conditions that might benefit from bile acid sequestration in the gastrointestinal tract and/or increased fecal excretion of bile acids and/or bile acid metabolites, by administering the amine polymer to an animal subject in need thereof. The amine polymers exhibit increased affinity and/or capacity for binding bile salts and/or their retention as compared to commercial bile acid sequestrants. The polymers have a combination of hydrogen bonding and electrostatic properties, charged nitrogen atoms, hydrophobicity and/or polymer architecture to provide such increased affinity and/or capacity for bile salts. The terms "bile acid" and "bile salt" are used interchangeably herein and those of skill in the art will understand that a bile acid will be present in salt form and, to a lesser degree, in the protonated form in the gastrointestinal tract.

The amine polymer can comprise repeat units derived from polymerization of an amine monomer having six, seven or eight possible reaction sites and a crosslinking monomer having two or three possible reaction sites, wherein the molar ratio of the amine monomer to the crosslinking monomer is in the range of from 1:3 to about 1:1.1, and the amine polymer has a binding affinity for bile acids of at least 0.46 mmol/g when measured using an in vitro A assay.

Also, the amine polymer can comprise the reaction product of an amine monomer having six, seven or eight possible reaction sites and a crosslinking monomer, wherein units of the polymer have the structure of formula 1:

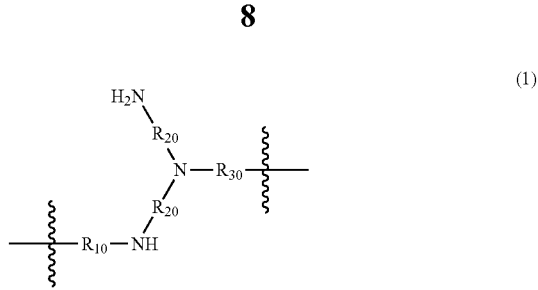

wherein $R_{10}$ is derived from the crosslinking monomer and is $C_2$ to $C_{16}$ alkylene, —NH—C(NH)—NH—, —NH—C(NH$_2^+$)—NH—, or $C_2$ to $C_{50}$ alkylene wherein one or more of the —$CH_2$— groups of the alkylene group is replaced with an amide, a carbonyl, an ether, an ester, a cycloalkyl, or a heterocyclo functional group, or one or more of the —$CH_2$— groups of the alkylene group is substituted with hydroxy; $R_{30}$ is derived from the amine monomer and is $C_2$ to $C_{12}$ alkylene, arylene, diformylheterocyclo, or $C_2$ to $C_{12}$ alkylene wherein one or more of the —$CH_2$— groups of the alkylene group is replaced with an amide, a carbonyl, a cycloalkyl, an aryl, or a heterocyclo functional group; each $R_{20}$ is independently $C_2$ to $C_6$ alkylene or $C_2$ to $C_6$ alkylene wherein one or more of the —$CH_2$— groups of the alkylene group is replaced with an amide functional group; and at least one of $R_{10}$ or $R_{30}$ is a hydrophobic group having a calculated log P (c Log P) of greater than 4.

The amine polymer can also comprise the reaction product of an amine monomer having six, seven or eight possible reaction sites and a crosslinking monomer wherein units of the polymer have the general structure of formula 1 wherein $R_{10}$ is derived from the crosslinking monomer and is $C_2$ to $C_{16}$ alkylene, —NH—C(NH)—NH—, —NH—C(NH$_2^+$)—NH—, or $C_2$ to $C_{50}$ alkylene wherein one or more of the —$CH_2$— groups of the alkylene group is replaced with an amide, a carbonyl, an ether, an ester, a cycloalkyl, or a heterocyclo functional group, or one or more of the —$CH_2$— groups of the alkylene group is substituted with hydroxy; $R_{30}$ is derived from the amine monomer and is $C_2$ to $C_6$ alkylene; each $R_{20}$ is independently $C_2$ to $C_6$ alkylene or $C_2$ to $C_6$ alkylene wherein one or more of the —$CH_2$— groups of the alkylene group is replaced with an amide functional group; and $R_{10}$ is a hydrophobic group having a calculated log P (c Log P) of greater than 4.

Additionally, the amine polymer can comprise the reaction product of an amine monomer having six, seven or eight possible reaction sites and a crosslinking monomer wherein units of the polymer have the general structure of formula 1 wherein $R_{10}$ is derived from the crosslinking monomer and is $C_8$ to $C_{16}$ alkylene, or $C_8$ to $C_{50}$ alkylene wherein one or more of the —$CH_2$— groups of the alkylene group is replaced with an amide, a carbonyl, an ether, an ester, a cycloalkyl, an aryl, or a heterocyclo functional group; $R_{30}$ is derived from the amine monomer and is $C_2$ to $C_{12}$ alkylene, arylene, diformylheterocyclo, or $C_2$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; and each $R_{20}$ is independently $C_2$ to $C_6$ alkylene or $C_2$ to $C_6$ alkylene wherein one or more of the —$CH_2$— groups of the alkylene group is replaced with an amide functional group.

The amine polymer can also comprise the reaction product of an amine monomer having six, seven or eight possible reaction sites and a crosslinking monomer wherein units of the polymer have the general structure of formula 1 wherein $R_{10}$ is derived from the crosslinking monomer and is $C_2$ to $C_6$ alkylene, or $C_2$ to $C_6$ alkylene wherein one or more of the —$CH_2$— groups of the alkylene group is replaced with an amide, a carbonyl, an ether, an ester, a cycloalkyl, an aryl, or a heterocyclo functional group, or one or more of the —$CH_2$— groups of the alkylene group is substituted with hydroxy; $R_{30}$ is derived from the amine monomer and is $C_8$ to $C_{16}$ alkylene, arylene, diformylheterocyclo, or $C_8$ to $C_{16}$ alkylene wherein one or more of the —$CH_2$— groups of the alkylene group is replaced with an amide, a carbonyl, an ether, an ester, a cycloalkyl, an aryl, or a heterocyclo functional group; and each $R_{20}$ is independently $C_2$ to $C_6$ alkylene or $C_2$ to $C_6$ alkylene wherein one or more of the —$CH_2$— groups of the alkylene group is replaced with an amide functional group.

The amine polymers described herein can have a binding affinity for bile acids of at least 0.46 mmol/g when measured in vitro using an in vitro A assay. The amine polymers described herein can also have a molar ratio of the amine monomer to the crosslinking monomer in the range of from 1:3 to about 1:1.1. For the amine polymers having a structure of formula 1, the primary and secondary amine atoms can have a calculated ratio from 1:1 to about 1:5.

The amine polymer can also comprise the reaction product of an amine monomer having six, seven or eight possible reaction sites and a crosslinking monomer having two or three possible reaction sites, wherein the polymer is insoluble in water, at least some of said amine secondary nitrogen atoms are part of a crosslinked polymer network, and the crosslinking monomer is a compound having the formula X—$R_1$—X, wherein each X is independently a leaving group, and $R_1$ is $C_8$ to $C_{50}$ alkylene, or $C_8$ to $C_{50}$ alkylene wherein one or more of the —$CH_2$— groups of the alkylene group is replaced with an amide, a carbonyl, an ether, an ester, a cycloalkyl, an aryl, or a heterocyclo functional group and the calculated log P (c Log P) of the crosslinking monomer is greater than 4.

The amine polymer can also comprise the reaction product of an amine monomer having six, seven or eight possible reaction sites and a crosslinking monomer having two or three possible reaction sites, wherein the polymer is insoluble in water, at least some of said amine secondary nitrogen atoms are part of a crosslinked polymer network, and the amine monomer has at least one segment that is a $C_8$ to $C_{16}$ alkylene, arylene, or $C_8$ to $C_{50}$ alkylene wherein one or more of the —$CH_2$— groups of the alkylene group is replaced with an amide, a carbonyl, an ether, an ester, a cycloalkyl, an aryl, or a heterocyclo functional group, and a calculated log P (c Log P) of the at least one segment of the amine monomer is greater than 4; and the crosslinking monomer is a compound having the formula X—$R_1$—X, wherein each X is independently a leaving group, and $R_1$ is $C_2$ to $C_6$ alkylene, or $C_2$ to $C_6$ alkylene wherein one or more of the —$CH_2$— groups of the alkylene group is replaced with an amide, a carbonyl, an ether, an ester, a cycloalkyl, an aryl, or a heterocyclo functional group, or one or more of the —$CH_2$— groups of the alkylene group is substituted with hydroxy.

Further, the amine polymer can comprise repeat units derived from polymerization of an amine monomer having six, seven or eight possible reaction sites and a crosslinking monomer having two or three possible reaction sites, wherein the molar ratio of the amine monomer to the crosslinking monomer is in the range of from 1:3 to about 1:1.1, and wherein: the polymer binds phosphate in vitro in an amount of less than 0.3 mmol/gram of polymer when measured using a B assay; and the polymer binds bile acids with an in vitro capacity of greater than about 3 mmol/gram of polymer when measured using a B assay.

The amine polymer can comprise units of the polymer having the structure of formula 1 wherein $R_{10}$ is $C_2$ to $C_{16}$ alkylene, arylene, —NH—C(NH)—NH—, —NH—C($NH_2^+$)—NH—, dimethylbiphenyl, or $C_2$ to $C_{50}$ alkylene wherein one or more of the —$CH_2$— groups of the alkylene group is replaced with an amide, a carbonyl, an ether, an ester, a cycloalkyl, an aryl, or a heterocyclo functional group, or one or more of the —$CH_2$— groups of the alkylene group is substituted with hydroxy; $R_{30}$ is $C_2$ to $C_{12}$ alkylene, arylene, diformylheterocyclo, or $C_2$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; and each $R_{20}$ is independently $C_2$ to $C_8$ alkylene or $C_2$ to $C_8$ alkylene wherein one or more of the —$CH_2$— groups of the alkylene group is replaced with an amide functional group; the polymer binds phosphate in vitro in an amount of less than 0.3 mmol/gram of polymer when measured using a B assay; and the polymer binds bile acids with an in vitro capacity of greater than about 3 mmol/gram of polymer when measured using a B assay. In some instances, the amine polymer comprises the reaction product of an amine monomer having six, seven or eight possible reaction sites and a crosslinking monomer and $R_{10}$ is derived from the crosslinking monomer and $R_{30}$ is derived from the amine monomer. In some cases, the amine polymer binds phosphate in vitro in an amount of less than 0.2 mmol/gram of polymer when measured using a B assay.

Some of the amine polymers having units of the polymer of Formula 1 can have an $R_{30}$ of ethylene, propylene, butylene, pentylene, hexylene, heptylene, octylene, decylene, undecylene, dodecylene, 3,3'-(1H-imidazole-3-ium-1,3-diyl)dipropyl, 1,4-phenylenedimethyl, 1,6-dioxohexane-1,6-diyl, or 2,6-diformylpyridine. Further, in some amine polymers having units of the polymer of Formula 1, $R_{30}$ is $C_3$ to $C_{12}$ alkylene; particularly, $R_{30}$ is butylene; also $R_{30}$ can be decylene or dodecylene. Further for amine polymers having units of the polymer of Formula 1, each $R_{20}$ can independently be $C_2$ to $C_6$ alkylene; each $R_{20}$ can independently be $C_2$ to $C_4$ alkylene; particularly, each $R_{20}$ can be propylene.

Also, the amine polymer comprises units of the polymer having nodes of positive charge separated by aliphatic segments. The nodes of positive charge have a charge density of at least 19.0 mEq/g and a molecular weight of at least 200.0 g/mol and at least one aliphatic segment is bonded to each node of positive charge, the at least one aliphatic segment having a calculated log P (c Log P) greater than 4 and wherein each of the nodes of positive charge does not contain an aliphatic segment having a calculated log P (c Log P) greater than 4.

In some instances, the amine polymer comprises units of the polymer having nodes of positive charge separated by aliphatic segments, wherein the nodes of positive charge have a charge density greater than 17.3 mEq/g and the structure of formula A

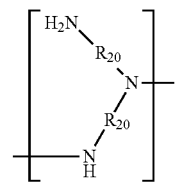

wherein each $R_{20}$ is independently $C_3$ to $C_8$ alkylene or $C_3$ to $C_8$ alkylene wherein one or more of the —$CH_2$— groups of the alkylene group is replaced with an amide functional group; and wherein at least one aliphatic segment is bonded to each node of positive charge, each aliphatic segment having a calculated log P (c Log P) greater than 4. The aliphatic segments separating the nodes of positive charge can be a $C_8$ to $C_{16}$ alkylene, or $C_8$ to $C_{50}$ alkylene wherein one or more of the —$CH_2$— groups of the alkylene group is replaced with an amide, a carbonyl, an ether, an ester, a cycloalkyl, an aryl, or a heterocyclo functional group. For some of the polymers, the polymer binds phosphate in vitro in an amount of less than 0.3 mmol/gram of polymer when measured using a B assay; and the polymer binds bile acids with an in vitro capacity of greater than about 3 mmol/gram of polymer when measured using the B assay. In some cases, the polymer binds phosphate in vitro in an amount of less than 0.2 mmol/gram of polymer when measured using the B assay. Also, in some of the polymers, each of the nodes of positive charge does not contain an aliphatic segment having a calculated log P (c Log P) greater than 4.

An amine polymer can also comprise repeat units derived from polymerization of an amine monomer and a crosslinking monomer, wherein the amine monomer is an amine of formula 2 having the structure:

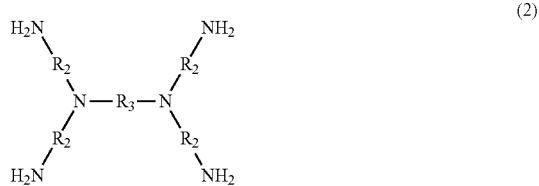

(2)

wherein each $R_2$ is independently $C_2$ to $C_8$ alkylene or $C_2$ to $C_8$ alkylene wherein one or more of the —$CH_2$— groups of the alkylene group is replaced with at least one amide functional group, and $R_3$ is $C_2$ to $C_{12}$ alkylene, arylene, diformylheterocyclo, or $C_2$ to $C_8$ alkylene wherein one or more of the —$CH_2$— groups of the alkylene group is replaced with an amide, a carbonyl, an ether, an ester, a cycloalkyl, an aryl, or a heterocyclo functional group; and the crosslinking monomer is guanidine, a guanidinium salt, a compound having the formula X—$R_1$—X, or a combination thereof, wherein each X is independently a leaving group, $R_1$ is $C_8$ to $C_{16}$ alkylene, or $C_5$ to $C_{50}$ alkylene wherein one or more of the —$CH_2$— groups of the alkylene group is replaced with an amide, a carbonyl, an ether, an ester, a cycloalkyl, an aryl, or a heterocyclo functional group, or one or more of the —$CH_2$— groups of the alkylene group is substituted with hydroxy. In some instances, $R_1$ is $C_8$ to $C_{16}$ alkylene, or $C_5$ to $C_{50}$ alkylene wherein one or more of the —$CH_2$— groups of the alkylene group is replaced with an amide, a carbonyl, an ether, an ester, a cycloalkyl, an aryl, or a heterocyclo functional group.

Some of the amine polymers described herein above are derived from an amine monomer which is an amine of formula 2 wherein each $R_2$ is independently $C_2$ to $C_8$ alkylene or $C_2$ to $C_8$ alkylene wherein one or more of the —$CH_2$— groups of the alkylene group is replaced with an amide functional group, and $R_3$ is $C_2$ to $C_{12}$ alkylene, arylene, diformylheterocyclo, or $C_2$ to $C_8$ alkylene wherein one or more of the —$CH_2$— groups of the alkylene group is replaced with an amide, a carbonyl, an ether, an ester, a cycloalkyl, an aryl, or a heterocyclo functional group. In some instances, the crosslinking monomer used in deriving the polymers is guanidine, a guanidinium salt, a compound having the formula X—$R_1$—X, or a combination thereof, wherein each X is independently a leaving group, $R_1$ is $C_8$ to $C_{16}$ alkylene, dimethylbiphenyl, or $C_2$ to $C_{50}$ alkylene wherein one or more of the —$CH_2$— groups of the alkylene group is replaced with a phenyl, piperidinium or imidazolium functional group. In some cases, $R_1$ is $C_8$ to $C_{16}$ alkylene, dimethylbiphenyl, or $C_2$ to $C_{50}$ alkylene wherein one or two of the —$CH_2$— groups of the alkylene group is replaced with one or two phenyl, piperidinium or imidazolium functional groups.

Others of the amine polymers described herein are derived from the polymerization of an amine of formula 2 wherein each $R_2$ is independently $C_2$ to $C_8$ alkylene or $C_2$ to $C_8$ alkylene wherein one or more of the —$CH_2$— groups of the alkylene group is replaced with an amide functional group, and $R_3$ is $C_8$ to $C_{16}$ alkylene, arylene, diformylheterocyclo, or $C_8$ to $C_{16}$ alkylene wherein one or more of the —$CH_2$— groups of the alkylene group is replaced with an amide, a carbonyl, an ether, an ester, a cycloalkyl, an aryl, or a heterocyclo functional group; and a crosslinking monomer which is a compound having the formula X—$R_1$—X, wherein each X is independently a leaving group, $R_1$ is $C_2$ to $C_6$ alkylene or $C_2$ to $C_6$ alkylene wherein one or more of the —$CH_2$— groups of the alkylene group is replaced with an amide, a carbonyl, an ether, an ester, a cycloalkyl, an aryl, or a heterocyclo functional group, or one or more of the —$CH_2$— groups of the alkylene group is substituted with hydroxy.

The amine polymers derived from an amine monomer of Formula 2 can have an $R_3$ of ethylene, propylene, butylene, pentylene, hexylene, heptylene, octylene, decylene, undecylene, dodecylene, 3,3'-(1H-imidazole-3-ium-1,3-diyl)dipropyl, 1,4-phenylenedimethyl, 1,6-dioxohexane-1,6-diyl, or 2,6-diformylpyridine. Further, in some amine polymers derived from an amine monomer of Formula 2, $R_3$ is $C_3$ to $C_{12}$ alkylene; particularly, $R_3$ is butylene; also $R_3$ can be decylene or dodecylene. Further for amine polymers derived from an amine monomer of Formula 2, each $R_2$ can independently be $C_2$ to $C_6$ alkylene; each $R_2$ can independently be $C_2$ to $C_4$ alkylene; particularly, each $R_2$ can be propylene.

In some embodiments, the amine polymer can have the general structure of formula 5

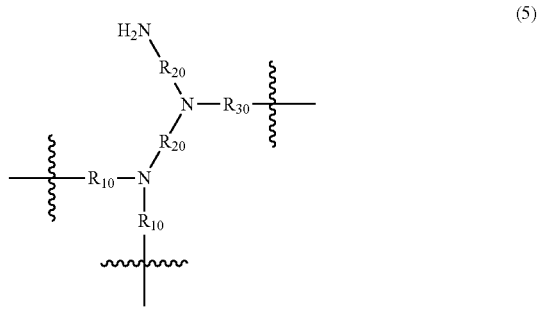

(5)

wherein $R_{10}$, $R_{20}$, and $R_{30}$ have the definitions above in connection with formula 1. Formula 5 represents a crosslink within the polymer network, which may form. In some instances, the crosslink can be represented in Formula 5 as a tetrasubstituted nitrogen (quaternized) to generate a formula containing $N(R_{20})(R_{10})_3$ or the crosslink can be represented in Formula 1 as $N(R_{20})(R_{10})(R_{10})$.

Additionally, the amine polymer can be derived from polymerization of an amine monomer and a crosslinking monomer wherein the amine monomer is an amine of formula 3 having the structure:

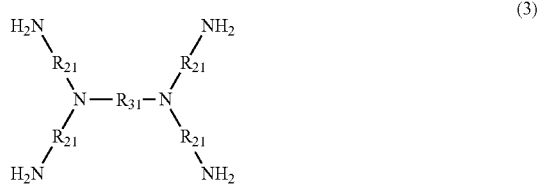

(3)

wherein each $R_{21}$ is independently $C_2$ to $C_8$ wherein one or more of the —$CH_2$— groups of the alkylene group is replaced with at least one sulfur atom, and $R_{31}$ is $C_2$ to $C_{12}$ alkylene, arylene, diformylheterocyclo, or $C_2$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; and the crosslinking monomer is guanidine, a guanidinium salt, a compound having the formula X—$R_1$—X, or a combination thereof, wherein each X is independently a leaving group, and $R_1$ is $C_2$ to $C_{16}$ alkylene, arylene, dimethylbiphenyl, or $C_2$ to $C_{50}$ alkylene wherein one or more of the —$CH_2$— groups of the alkylene group is replaced with an amide, a carbonyl, an ether, an ester, a cycloalkyl, an aryl, or a heterocyclo functional group, or one or more of the —$CH_2$— groups of the alkylene group is substituted with hydroxy. In some instances, each $R_{21}$ is m-sulfidoC$_m$alkyl, m is an integer from 1 to 6 and $R_{31}$ is $C_3$ to $C_8$ alkylene. In some amine polymers derived from an amine monomer of Formula 3, $R_{31}$ is $C_3$ to $C_{12}$ alkylene; particularly, $R_{31}$ is butylene; also $R_{31}$ can be decylene or dodecylene.

Further, an amine of formula 6 has the structure:

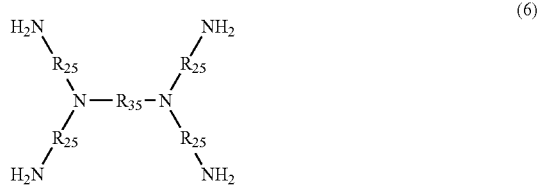

(6)

wherein each $R_{25}$ is independently $C_2$ to $C_8$ alkylene or $C_2$ to $C_8$ alkylene wherein one or more of the —$CH_2$— groups of the alkylene group is replaced with at least one amide functional group, and $R_{35}$ is $C_8$ to $C_{16}$ alkylene, or $C_8$ to $C_{16}$ alkylene wherein one or more of the —$CH_2$— groups of the alkylene group is replaced with an amide, a carbonyl, an ether, an ester, a cycloalkyl, an aryl, or a heterocyclo functional group. In some embodiments, each $R_{25}$ is independently $C_3$ to $C_6$ alkylene; particularly propylene. In various instances, $R_{35}$ is $C_{10}$ to $C_{14}$ alkylene; particularly decylene or dodecylene. The amine of Formula 6 can be used as an amine monomer in the polymerization reaction to form some of the amine polymers described herein.

Many of the amine polymers described herein can undergo a post polymerization reaction, which comprises reaction of the amine polymer with at least one additional crosslinking monomer or a ligand. When the amine polymers undergo such a post polymerization reaction with two crosslinking monomers, the reaction can proceed with both the crosslinking monomers present (e.g., by using cross linking monomers with different reactivity rates) or the amine monomer can react with one crosslinking monomer and then react with the second crosslinking monomer (e.g., the cross linking monomers are added sequentially to the reactor or the polymer is recovered prior to reaction with the second cross linking monomer). These reactions with two or more different crosslinking monomers can provide improved yield or improved physical characteristics. When these further reactions occur with an additional ligand, the crosslinking monomer and the ligand can be added simultaneously or sequentially as well.

Further, the amine monomer is other than a dendrimer wherein a dendrimer has a hyperbranched fractal-like structure that emanates from a central core and consists of a large number of terminal groups with a definite geometrical growth (Peppas et al., "Dendrimers and star polymers for pharmaceutical and medical applications," Proceed. Intern. Symp. Control. Rel. Bioact. Mater, 20:143-144 (1993)).

In the amine polymers described herein the crosslinking monomer can be guanidine, a guanidinium salt, a compound having the formula X—$R_1$—X, or a combination thereof, wherein each X is independently a leaving group, and $R_1$ is $C_2$ to $C_{16}$ alkylene, arylene, dimethylbiphenyl, or $C_2$ to $C_{50}$ alkylene wherein one or more of the —$CH_2$— groups of the alkylene group is replaced with an amide, a carbonyl, an ether, an ester, a cycloalkyl, an aryl, or a heterocyclo functional group, or one or more of the —$CH_2$— groups of the alkylene group is substituted with hydroxy. In some instances, the crosslinking monomer is X—$R_1$—X wherein each X is independently a leaving group, and $R_1$ is $C_8$ to $C_{16}$ alkylene, or $C_8$ to $C_{50}$ alkylene wherein one or more of the —$CH_2$— groups of the alkylene group is replaced with a heterocyclo functional group. In other instances, the crosslinking monomer is X—$R_1$—X wherein each X is independently a leaving group, and $R_1$ is $C_2$ to $C_6$ alkylene wherein one or more of the —$CH_2$— groups of the alkylene group is replaced with a heterocyclo functional group, or one or more of the —$CH_2$— groups of the alkylene group is substituted with hydroxy. In other instances, the crosslinking monomer is guanidine, a guanidinium salt, a compound having the formula X—$R_1$—X, or a combination thereof, wherein each X is independently a leaving group, $R_1$ is $C_8$ to $C_{16}$ alkylene, dimethylbiphenyl, or $C_2$ to $C_{50}$ alkylene wherein one or more of the —$CH_2$— groups of the alkylene group is replaced with one or two phenyl, piperidinium or imidazolium functional groups.

For the amine polymers having a crosslinking monomer of formula X—$R_1$—X, where $R_1$ is $C_2$ to $C_{50}$ alkylene wherein one or more of the —$CH_2$— groups of the alkylene group is replaced with one or two phenyl, piperidinium or imidazolium functional groups, the functional groups can be p-xylene, 1,3-bis(m-haloC$_m$alkyl)-1H-imidazol-3-ium, 4,4'-(C$_x$alkane-1,x-diyl)bis(1-(m-haloC$_m$alkyl)-1-methylpiperidinium), or 1-(q-haloC$_q$alkyl)-3-(m-(3-(p-haloC$_p$alkyl)-1H-imidazol-3-ium-1-yl)C$_m$alkyl)-1H-imidazol-3-ium, wherein m is an integer from 2 to 14, p is an integer from 2 to 14, q is an integer from 2 to 14, and x is an integer from 2 to 8. For some amine polymers where the crosslinking monomer is X—$R_1$—X, X is independently a leaving group, and $R_1$ is $C_8$ to $C_{50}$ alkylene or $C_8$ to $C_{50}$ alkylene wherein one or more of the —$CH_2$— groups of the alkylene group is replaced with a heterocyclo functional group.

In various amine polymers, the crosslinking monomer is guanidine, guanidinium hydrohalide, 1,3-bis(3-halopropyl)-1H-imidazol-3-ium, 4,4'-(propane-1,3-diyl)bis(1-(10-halodecyl)-1-methylpiperidinium), 1-(12-halododecyl)-3-(12-(3-(12-halododecyl)-1H-imidazol-3-ium-1-yl)dodecyl)-1H-imidazol-3-ium, or 1-(10-halododecyl-3-(10-(3-(10-halodecyl)-1H-imidazol-3-ium-1-yl)decyl)-1H-imidazol-3-ium.

In some of the amine polymers, the crosslinking monomer is guanidine, a compound having the formula X—$R_1$—X wherein $R_1$ is $C_8$ to $C_{16}$ alkylene, or a combination thereof, and the polymer comprises a comonomer, the comonomer being $C_m$alkane-1,m-diyldiamine, alkylenedicycloalkanamine, (m-amino$C_m$alkyl)heterocycle, 3-(m-amino$C_m$alkyl)-1H-imidazol-3-ium, or a combination thereof, wherein m is an integer from 2 to 16, and each X is independently a leaving group, such as hexane-1,6-diyldiamine, heptane-1,7-diylamine, octane-1,8-diyldiamine, nonane-1,9-diylamine, decane-1,10-diyldiamine, undecane-1,11-diylamine, dodecane-1,12-diyldiamine, 4,4'-methylenedicyclohexanamine, 3-(3-aminopropyl)-1H-imidazol-3-ium, or a combination thereof. In some of the amine polymers, $R_1$ is $C_8$ to $C_{14}$ alkylene; particularly, $R_1$ is decylene or dodecylene. In other amine polymers, $R_1$ is $C_2$ to $C_6$ alkylene or $C_2$ to $C_6$ alkylene wherein one or more of the —$CH_2$— groups of the alkylene group is substituted with hydroxy; particularly, $R_1$ is —$CH_2$—CH(OH)—$CH_2$—, and the polymer comprises the comonomer.

In the amine polymers where the crosslinking monomer is X—$R_1$—X, X is halo, epoxy, diaziridino, mesylate, sulfate, phosphate, aldehyde, ketone, or a combination thereof. Leaving groups are well known and can be selected from those known in the art, such as those in Larock, Comprehensive Organic Transformations (VCH 1989), e.g., p. 397 et seq.

The amine polymers can comprise a comonomer, the comonomer being $C_m$alkane-1,m-diyldiamine, alkylenedicycloalkanamine, (m-amino$C_m$alkyl)heterocycle, 3-(m-amino$C_m$alkyl)-1H-imidazol-3-ium, or a combination thereof, wherein m is an integer from 2 to 16, and each X is independently a leaving group.

In one preferred embodiment, $R_1$ is $C_8$ to $C_{14}$ alkylene or $C_8$ to $C_{12}$ alkylene, such as decylene or dodecylene. In another preferred embodiment, $R_1$ is a $C_2$ to $C_6$ alkylene wherein one or more of the —$CH_2$— groups of the alkylene group is substituted with hydroxy, and more preferably a $C_2$ to $C_4$ alkylene wherein one or more of the —$CH_2$— groups of the alkylene group is substituted with hydroxy, such as —$CH_2$—CH(OH)—$CH_2$—. In the amine polymers wherein units of the polymer have the structure of Formula 1, $R_{10}$ can be $C_8$ to $C_{14}$ alkylene or $C_8$ to $C_{12}$ alkylene, such as decylene or dodecylene. In another preferred embodiment, $R_{10}$ is a $C_2$ to $C_6$ alkylene wherein one or more of the —$CH_2$— groups of the alkylene group is substituted with hydroxy, and more preferably a $C_2$ to $C_4$ alkylene wherein one or more of the —$CH_2$— groups of the alkylene group is substituted with hydroxy, such as —$CH_2$—CH(OH)—$CH_2$—.

The various embodiments reflect that the amine polymer has nodes of positive charge separated by aliphatic segments. The aliphatic segments are preferably hydrophobic. The hydrophobicity is combined with sufficient positive charge for efficient and effective affinity and retention of bile salts. The combination provides an unexpected improvement in bile acid binding affinity, binding capacity, retention and removal as compared to (i) conventional bile acid binders having hydrophilic crosslinkers that prevent the collapsing of the polymer network due to the absorption of hydrophobic elements, such as bile acids and fatty acids present in the GI and (ii) conventional bile acid binders with insufficient charge density in proximity to the hydrophobic elements. In various embodiments, a node of positive charge is generally a collection of three or more nitrogen atoms is defined by an appropriate combination of charge density, molecular weight and/or structure. The charge density of a node is generally greater than 16.5 mEq/g, greater than 17.3 mEq/g, greater than 19 mEq/g, and even more specifically greater than 22 mEq/g. Charge density is calculated in accordance with formulas known to those of skill in the art assuming a 100% degree of ionization of the nitrogen atoms for purposes of the calculation. The formula used herein is that the charge density in mEq/g units is equal to the number of nitrogen atoms in the node multiplied by one over the molecular weight of the node multiplied by one thousand or (# N atoms)×(1/molecular weight)×(1000). The formula weight of the node of positive charge is calculated for the neutral amine by adding hydrogen atoms to each nitrogen atom of the node until each nitrogen atom has three bonds. The nodes of positive charge can have a molecular weight of greater than 50 mol/g, greater than 100 mol/g, greater than 125 mol/g or greater than 200 mol/g. For example, the charge density and molecular weight for various nodes are detailed in Table 1.

TABLE 1

Charge density and molecular weight of selected nodes

| Node | Molecular weight | Charge Density (mEq/g) |
|---|---|---|
| (structure with NH₂) | 43.07 | 23 |
| (structure with H₂N, NH, H₂N) | 131.22 | 22.9 |
| (structure H₂N–––NH₂) | 116.20 | 17.2 |

TABLE 1-continued
Charge density and molecular weight of selected nodes
| Node | Molecular weight | Charge Density (mEq/g) |
|---|---|---|
| 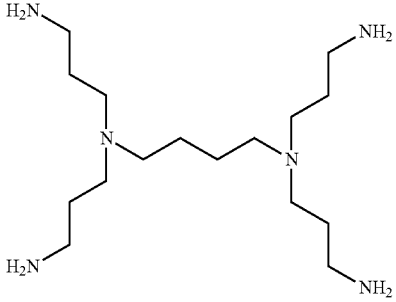 [SMILES: NCCCN(CCCN)CCCCN(CCCN)CCCN] | 316.53 | 19.0 |
| 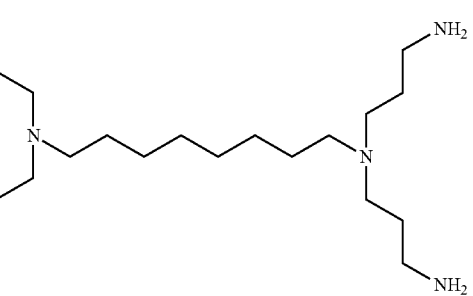 | 372.64 | 16.1 |
| 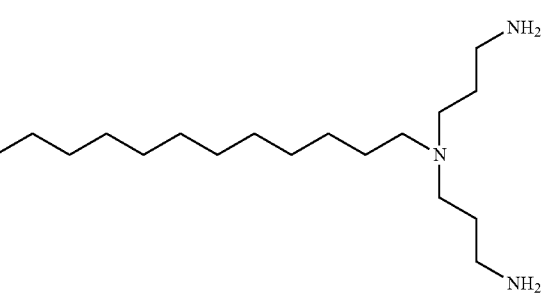 | 428.74 | 14.0 |
| 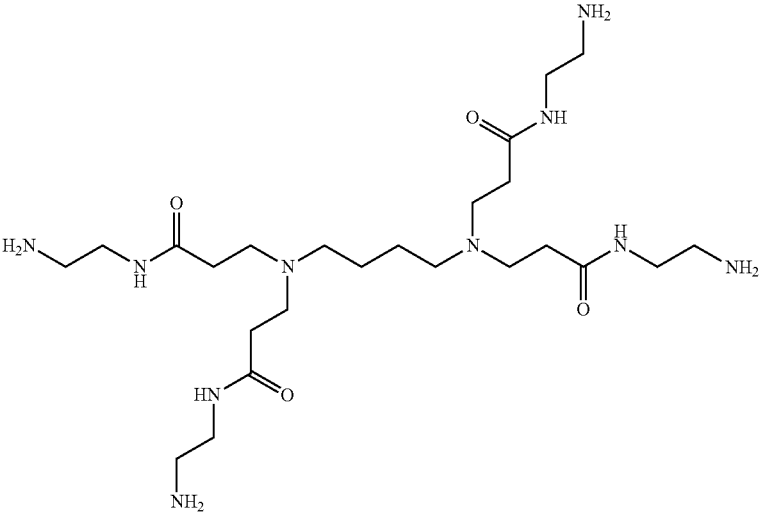 [SMILES: NCCNC(=O)CCN(CCCCN(CCC(=O)NCCN)CCC(=O)NCCN)CCC(=O)NCCN] | 544.73 | 18.4 |

A node of positive charge preferably has the structure of formula A

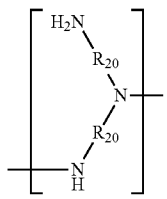

wherein each $R_{20}$ is independently $C_3$ to $C_8$ alkylene or $C_3$ to $C_8$ alkylene wherein one or more of the —$CH_2$— groups of the alkylene group is replaced with an amide functional group.

In some embodiments, the nodes of positive charge are separated by hydrophobic aliphatic segments. The hydrophobicity of an aliphatic segment is expressed by the calculated log P, as discussed herein.

The amine polymer can also comprise repeat units derived from polymerization of an amine monomer of formula 2 and a crosslinking monomer, wherein the amine monomer of formula 2 has the structure:

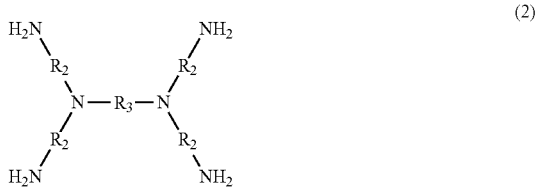

wherein each $R_2$ is independently $C_2$ to $C_8$ alkylene or $C_2$ to $C_8$ alkylene wherein one or more of the —$CH_2$— groups of the alkylene group is replaced with an amide functional group; and $R_3$ is $C_2$ to $C_{12}$ alkylene, arylene, diformylheterocyclo, or $C_2$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; and a portion of the nitrogen atoms of the amine polymer are substituted with a ligand selected from aminoalkyl, aryl, arylalkyl, oxoalkyl, cycloalkyl, (cycloalkyl)alkyl, guanidino, heterocyclo, heterocyloalkyl, (trialkylammonio)alkyl, 2-(protected amino)-m-(heterocyclo)-1-oxoC$_m$alkyl, 2-(protected amino)-1-oxoC$_m$alkyl, 2-(protected amino)-3-methyl-1-oxoC$_m$alkyl, 2-(protected amino)-4-methyl-1-oxoC$_m$alkyl, 2-(protected amino)-1-oxo-m-arylC$_m$alkyl, 2-(protected amino)-m-(alkylthio)-1-oxoC$_m$alkyl, 2-(protected amino)-m-(aryl)-1-oxoC$_m$alkyl, 2-(protected amino)-m-carboxy-1-oxoC$_m$alkyl, 2-(protected amino)-m-guanidino-1-oxoC$_m$alkyl, 2-(protected amino)-(m−1)-hydroxy-1-oxoC$_m$alkyl, 2-(protected amino)-m-hydroxy-1-oxoC$_m$alkyl, 2-(protected amino)-m-mercapto-1-oxoC$_m$alkyl, m-(alkylamino)-m-oxoC$_m$alkyl, m-(alkylheterocyclo)C$_m$alkyl, m-amino-2-(protected amino)-1-oxoC$_m$alkyl, m-amino-2-(protected amino)-1,m-dioxoC$_m$alkyl, m-(x-aminoC$_x$alkyl)heterocycloC$_m$alkyl, (m−1)-amino-m-(heterocyclo)-1-oxoC$_m$alkyl, m-(arylalkylamino)-m-oxoC$_m$alkyl, m-(x-(alkylthio)C$_x$alkylamino)-m-oxoC$_m$alkyl, m-(x-aminoC$_x$alkylamino)-m-oxoC$_m$alkyl, m-(x-amino-x-oxoC$_x$alkylamino)-m-oxoC$_m$alkyl, m-(x-carboxyC$_x$alkylamino)-m-oxoC$_m$alkyl, m-(heterocycloalkylamino)-m-oxoC$_m$alkyl, m-(x-hydroxyC$_x$alkylamino)-m-oxoC$_m$alkyl, m-((x−1)-hydroxyC$_x$alkylamino)-m-oxoC$_m$alkyl, m-(x-mercaptoC$_x$alkylamino)-m-oxoC$_m$alkyl, m-(x-trialkylammonioC$_x$alkyl)heterocycloC$_m$alkyl, m-(x-(2-(alkoxy)benzamido)C$_x$alkylamino)-m-oxoC$_m$alkyl, m-(x-(3-(alkoxy)benzamido)C$_x$alkylamino)-m-oxoC$_m$alkyl, m-(x-(4-(alkoxy)benzamido)C$_x$alkylamino)-m-oxoC$_m$alkyl, a ligand of formula 4

$$*—R_{46}—R_{47}—R_{48} \quad (4)$$

or a combination thereof, wherein $R_{46}$ is $C_6$ to $C_{16}$ alkylene, $R_{47}$ is 1,y-bis(1-methylpiperidin-4-yl)C$_y$alkylene, $R_{48}$ is $C_6$ to $C_{16}$ alkyl, m is an integer from 3 to 12, x is an integer from 1 to 12, y is an integer from 1 to 14, and z is an integer from 1 to 16.

The amine polymers described herein can also have a portion of the nitrogen atoms of the amine polymer substituted with a ligand post-polymerization of alkyl, aminoalkyl, aryl, arylalkyl, oxoalkyl, cycloalkyl, (cycloalkyl)alkyl, guanidino, heterocyclo, heterocycloalkyl, (trialkylammonio)alkyl, 2-(protected amino)-m-(heterocyclo)-1-oxoC$_m$alkyl, 2-(protected amino)-1-oxoC$_m$alkyl, 2-(protected amino)-3-methyl-1-oxoC$_m$alkyl, 2-(protected amino)-4-methyl-1-oxoC$_m$alkyl, 2-(protected amino)-1-oxo-m-arylC$_m$alkyl, 2-(protected amino)-m-(alkylthio)-1-oxoC$_m$alkyl, 2-(protected amino)-m-(aryl)-1-oxoC$_m$alkyl, 2-(protected amino)-m-carboxy-1-oxoC$_m$alkyl, 2-(protected amino)-m-guanidino-1-oxoC$_m$alkyl, 2-(protected amino)-(m−1)-hydroxy-1-oxoC$_m$alkyl, 2-(protected amino)-m-hydroxy-1-oxoC$_m$alkyl, 2-(protected amino)-m-mercapto-1-oxoC$_m$alkyl, m-(alkylamino)-m-oxoC$_m$alkyl, m-(alkylheterocyclo)C$_m$alkyl, m-amino-2-(protected amino)-1-oxoC$_m$alkyl, m-amino-2-(protected amino)-1,m-dioxoC$_m$alkyl, m-(x-aminoC$_x$alkyl)heterocycloC$_m$alkyl, (m−1)-amino-m-(heterocyclo)-1-oxoC$_m$alkyl, m-(arylalkylamino)-m-oxoC$_m$alkyl, m-(x-(alkylthio)C$_x$alkylamino)-m-oxoC$_m$alkyl, m-(x-aminoC$_x$alkylamino)-m-oxoC$_m$alkyl, m-(x-amino-x-oxoC$_x$alkylamino)-m-oxoC$_m$alkyl, m-(x-carboxyC$_x$alkylamino)-m-oxoC$_m$alkyl, m-(heterocycloalkylamino)-m-oxoC$_m$alkyl, m-(x-hydroxyC$_x$alkylamino)-m-oxoC$_m$alkyl, m-((x−1)-hydroxyC$_x$alkylamino)-m-oxoC$_m$alkyl, m-(x-mercaptoC$_x$alkylamino)-m-oxoC$_m$alkyl, m-(x-trialkylammonioC$_x$alkyl)heterocycloC$_m$alkyl, m-(x-(2-(alkoxy)benzamido)C$_x$alkylamino)-m-oxoC$_m$alkyl, m-(x-(3-(alkoxy)benzamido)C$_x$alkylamino)-m-oxoC$_m$alkyl, m-(x-(4-(alkoxy)benzamido)C$_x$alkylamino)-m-oxoC$_m$alkyl, a ligand of formula 4

$$*—R_{46}—R_{47}—R_{48} \quad (4)$$

or a combination thereof, wherein $R_{46}$ is $C_6$ to $C_{16}$ alkylene, $R_{47}$ is 1,y-bis(1-methylpiperidin-4-yl)C$_y$alkylene, $R_{48}$ is $C_6$ to $C_{16}$ alkyl, m is an integer from 3 to 12, x is an integer from 1 to 12, y is an integer from 1 to 14, and z is an integer from 1 to 16.

In some embodiments, the ligand is arylalkyl selected from naphthalen-2-ylalkyl or naphthalen-1-ylalkyl; heterocycloalkyl selected from m-(1-methylpyrrolidinium-1-yl)C$_m$alkyl, m-(2-(1H-indol-3-yl)ethylamino)-m-oxoC$_m$alkyl, m-(2-methylthiazol-3-ium-3-yl)C$_m$alkyl, m-(benzo[d]thiazol-3-ium-3-yl)C$_m$alkyl, m-(pyridinium-1-yl)C$_m$alkyl, m-(tetrahydro-1 H-thiophenium-1-yl)C$_m$alkyl, z-(1,2-dialkyl-1H-imidazol-3-ium-3-yl)C$_z$alkyl, m-(2,3-dialkyl-1H-imidazol-3-ium-1-yl)C$_m$alkyl, z-(1-alkyl-1H-imidazol-3-ium-3-yl)C$_z$alkyl, m-(3-alkyl-1H-imidazol-3-ium-1-yl)C$_m$alkyl, or z-(thiazol-3-ium-3-yl)C$_z$alkyl; 2-(protected amino)-m-(heterocyclo)-1-oxoC$_m$alkyl selected from 2-(protected amino)-m-(1H-indol-3-yl)-1-oxoC$_m$-alkyl or 2-(protected amino)-m-(1H-imidazol-4-yl)-1-oxoC$_m$alkyl; 2-(protected amino)-1-oxo-m-phenylC$_m$alkyl; 2-(protected amino)-m-(hydroxyphenyl)-1-oxoC$_m$alkyl; m-(alkylheterocyclo)C$_m$alkyl selected from m-(3-alkyl-1H-imidazol-3-ium-1-yl)C$_m$alkyl, m-(1-alkyl-1H-imidazol-3-ium-3-yl) C$_m$alkyl, m-(1-alkyl-2-methyl-1H-imidazol-3-ium-3-yl) C$_m$alkyl, or m-(3-alkyl-2-methyl-1H-imidazol-3-ium-1-yl) C$_m$alkyl; m-(x-aminoC$_x$alkyl)heterocycloC$_m$alkyl selected from m-(3-(x-aminoC$_x$alkyl)-1H-imidazol-3-ium-1-yl) C$_m$alkyl or m-(1-(x-aminoC$_x$alkyl)-1H-imidazol-3-ium-3-yl) C$_m$alkyl; (m−1)-amino-m-(1H-indol-2-yl)-1-oxoC$_m$alkyl; m-(arylalkylamino)-m-oxoC$_m$alkyl selected from m-(hydroxyphenalkylamino)-m-oxoC$_m$alkyl or m-(phenalkylamino)-m-oxo-C$_m$alkyl; m-(x-(heterocyclo)C$_x$alkyl) heterocycloC$_m$alkyl selected from m-(1-(x-(1-methyl-1H-imidazol-3-ium-3-yl)C$_x$alkyl)-1H-imidazol-3-ium-3-yl) C$_m$alkyl, m-(1-(x-(3-methyl-1H-imidazol-3-ium-1-yl)C$_x$alkyl)-1H-imidazol-3-ium-3-yl) C$_m$alkyl, m-(3-(x-(1-methyl-1H-imidazol-3-ium-3-yl)C$_x$alkyl)-1H-imidazol-3-ium-1-yl) C$_m$alkyl, or m-(3-(x-(3-methyl-1H-imidazol-3-ium-1-yl)C$_x$alkyl)-1H-imidazol-3-ium-1-yl) C$_m$alkyl; m-(x-(1H-imidazol-4-yl)C$_x$alkylamino)-m-oxoC$_m$alkyl; or m-(x-trialkylammonioC$_x$alkyl)heterocycloC$_m$alkyl selected from m-(3-(x-trialkylammonio)C$_x$alkyl)-1H-imidazol-3-ium-1-yl)C$_m$alkyl or m-(1-(x-trialkylammonio)C$_x$alkyl)-1H-imidazol-3-ium-3-yl)C$_m$alkyl wherein m is an integer from 3 to 12, x is an integer from 1 to 12, and z is an integer from 1 to 16.

In some instances, the ligand is derived from an amino acid. Such ligands include, but are not limited to, 2-(protected amino)-m-(heterocyclo)-1-oxoC$_m$alkyl, m-amino-2-(protected amino)-1,m-dioxoC$_m$alkyl, m-amino-2-(protected amino)-1-oxoC$_m$alkyl, 2-(protected amino)-1-oxoC$_m$alkyl, 2-(protected amino)-m-(alkylthio)-1-oxoC$_m$alkyl, 2-(protected amino)-m-(hydroxyphenyl)-1-oxoC$_m$alkyl, 2-(protected amino)-1-oxo-m-phenylC$_m$alkyl, 2-(protected amino)-m-(1H-imidazol-4-yl)-1-oxoC$_m$alkyl, 2-(protected amino)-m-carboxy-1-oxoC$_m$alkyl, 2-(protected amino)-3-methyl-1-oxoC$_m$alkyl, 2-(protected amino)-4-methyl-1-oxoC$_m$alkyl, 2-(protected amino)-m-mercapto-1-oxoC$_m$alkyl, 2-(protected amino)-(m−1)-hydroxy-1-oxoC$_m$alkyl, 2-(protected amino)-m-hydroxy-1-oxoC$_m$alkyl, 2-(protected amino)-m-guanidino-1-oxoC$_m$alkyl, m-(x-(alkylthio)C$_x$alkylamino)-m-oxoC$_m$alkyl, m-(hydroxyphenalkylamino)-m-oxoC$_m$alkyl, m-oxo-m-(phenalkylamino)-m-oxoC$_m$alkyl, m-(x-(1H-imidazol-4-yl)C$_x$alkylamino)-m-oxoC$_m$alkyl, m-(x-carboxyC$_x$alkylamino)-m-oxoC$_m$alkyl, m-(alkylamino)-m-oxoC$_m$alkyl, m-(x-mercaptoC$_x$alkylamino)-m-oxoC$_m$alkyl, m-((x−1)-hydroxyC$_x$alkylamino)-m-oxoC$_m$alkyl, m-(x-hydroxyC$_x$alkylamino)-m-oxoC$_m$alkyl, m-(x-aminoC$_x$alkylamino)-m-oxoC$_m$alkyl, or m-(x-amino-x-oxoC$_x$alkylamino)-m-oxoC$_m$alkyl, wherein m is an integer from 3 to 12, and x is an integer from 1 to 12.

Some of the amine polymers described herein have a portion of the nitrogen atoms of the amine polymer substituted with a ligand of 2-(tert-butoxycarbonylamino)-3-(1H-indol-3-yl)-1-oxopropyl, 5-(2-(4-(nonyloxy)benzamido)ethylamino)-5-oxopentyl, (4,5-dihydro-1H-imidazolyl, 10-(pyridinium-1-yl)decyl, 2-(1H-indol-3-yl)ethyl, 5-(2-(1H-indol-3-yl)ethylamino)-5-oxopentyl, 2-amino-3-(1H-indol-2-yl)-1-oxopropyl, 3-(1,2-dimethyl-1H-imidazol-3-ium-3-yl)propyl, 10-(1,2-dimethyl-1H-imidazol-3-ium-3-yl)decyl, 10-(1-methyl-1H-imidazol-3-ium-3-yl)decyl, 3-(thiazol-3-ium-3-yl)propyl, 3-aminopropyl, 3-cyclohexylpropyl, 3-phenylpropyl, 3-(trimethylammonio)propyl, 3-(1-methylpyrrolidinium-1-yl)propyl, 3-(2-methylthiazol-3-ium-3-yl)propyl, 3-(benzo[d]thiazol-3-ium-3-yl)propyl, 3-(tetrahydro-1H-thiophenium-1-yl)propyl, 3-(3-methyl-1H-imidazol-3-ium-1-yl)propyl, 3-(1-methyl-1H-imidazol-3-ium-3-yl)propyl, 3-(3-(3-aminopropyl)-1H-imidazol-3-ium-1-yl)propyl, 3-(1-(3-aminopropyl)-1H-imidazol-3-ium-3-yl)propyl, 3-(3-(5-trimethylammonio)pentyl)-1H-imidazol-3-ium-1-yl)propyl, 3-(1-(5-trimethylammonio)pentyl)-1H-imidazol-3-ium-3-yl)propyl, 3-(3-decyl-1H-imidazol-3-ium-1-yl)propyl, 3-(1-decyl-1H-imidazol-3-ium-3-yl)propyl, 3-(3-(9-(3-methyl-1H-imidazol-3-ium-1-yl)nonyl)-1H-imidazol-3-ium-1-yl)propyl, 3-(1-(9-(1-methyl-1H-imidazol-3-ium-3-yl)nonyl)-1H-imidazol-3-ium-3-yl) propyl, 3-(1-(9-(3-methyl-1H-imidazol-3-ium-1-yl)nonyl)-1H-imidazol-3-ium-3-yl)propyl, 3-(3-(9-(1-methyl-1H-imidazol-3-ium-3-yl)nonyl)-1H-imidazol-3-ium-1-yl) propyl, 4-(3-decyl-1H-imidazol-3-ium-1-yl)butyl, 4-(1-decyl-1H-imidazol-3-ium-3-yl)butyl, 10-(1-decyl-2-methyl-1H-imidazol-3-ium-3-yl)decyl, 10-(3-decyl-2-methyl-1H-imidazol-3-ium-1-yl)decyl, 3-(1,2-dimethyl-1H-imidazol-3-ium-3-yl)propyl, 3-(2,3-dimethyl-1H-imidazol-3-ium-1-yl) propyl, 10-(2,3-dimethyl-1H-imidazol-3-ium-1-yl)decyl, 10-(1,2-dimethyl-1H-imidazol-3-ium-3-yl)decyl, 10-(1-methyl-1H-imidazol-3-ium-3-yl)decyl, 10-(3-methyl-1H-imidazol-3-ium-1-yl)decyl, 10-(1-butyl-1H-imidazol-3-ium-3-yl)decyl, 10-(3-butyl-1H-imidazol-3-ium-1-yl)decyl, 10-(pyridinium-1-yl)decyl, 10-(1-methylpyrrolidinium-1-yl)decyl, naphthalen-2-ylmethyl, naphthalen-1-ylmethyl, 4-amino-2-(tert-butoxycarbonylamino)-1,4-dioxobutyl, 2-(tert-butoxycarbonylamino)-1-oxoethyl, 2-(tert-butoxycarbonylamino)-4-(methylthio)-1-oxobutyl, 5-(3-(methylthio)propylamino)-5-oxopentyl, 2-(tert-butoxycarbonylamino)-3-(4-hydroxyphenyl)-1-oxopropyl, 5-(4-hydroxyphenethylamino)-5-oxopentyl, 2-(tert-butoxycarbonylamino)-1-oxo-3-phenylpropyl, 5-oxo-5-(phenethylamino)pentyl, 2-(tert-butoxycarbonylamino)-3-(1H-imidazol-4-yl)-1-oxopropyl, 5-(2-(1H-imidazol-4-yl)ethylamino)-5-oxopentyl, 2-(tert-butoxycarbonylamino)-3-carboxy-1-oxopropyl, 5-(2-carboxyethylamino)-5-oxopentyl, 2-(tert-butoxycarbonylamino)-3-methyl-1-oxobutyl, 5-(isobutylamino)-5-oxopentyl,(3R)-2-(tert-butoxycarbonylamino)-3-methyl-1-oxopentyl,(R)-5-(2-methylbutylamino)-5-oxopentyl, 2-(tert-butoxycarbonylamino)-3-mercapto-1-oxopropyl, 5-(2-mercaptoethylamino)-5-oxopentyl,(3R)-2-(tert-butoxycarbonylamino)-3-hydroxy-1-oxobutyl,(R)-5-(2-hydroxypropylamino)-5-oxopentyl, 6-amino-2-(tert-butoxycarbonylamino)-1-oxohexyl, 5-(5-aminopentylamino)-5-oxopentyl, 5-amino-2-(tert-butoxycarbonylamino)-1,5-dioxopentyl, 5-(4-amino-4-oxobutylamino)-5-oxopentyl, 2-(tert-butoxycarbonylamino)-5-guanidino-1-oxopentyl, 5-(4-guanidinobutylamino)-5-oxopentyl, 2-(tert-butoxycarbonylamino)-3-hydroxy-1-oxopropyl, 5-(2-hydroxyethylamino)-5-oxopentyl, 2-(tert-butoxycarbonylamino)-4-methyl-1-oxopentyl, 5-(isopentylamino)-5-oxopentyl, 2-(tert-butoxycarbonylamino)-4-carboxy-1-oxobutyl, 5-(3-carboxypropylamino)-5-oxopentyl, 2-(tert-butoxycarbonylamino)-1-oxopropyl, 5-(ethylamino)-5-oxopentyl, a ligand of formula 4

$$*-R_{46}-R_{47}-R_{48} \quad (4)$$

or a combination thereof, wherein $R_{46}$ is decylene, $R_{47}$ is 1,3-bis(1-methylpiperidin-4-yl)propane, and $R_{48}$ is decyl.

Some of the amine polymers described herein have a portion of the nitrogen atoms of the amine polymer substituted with a ligand of 2-(tert-butoxycarbonylamino)-3-(1H-indol-3-yl)-1-oxopropyl, 5-(2-(4-(nonyloxy)benzamido)ethylamino)-5-oxopentyl, (4,5-dihydro-1H-imidazolyl, 10-

(pyridinium-1-yl)decyl, 2-(1H-indol-3-yl)ethyl, 5-(2-(1H-indol-3-yl)ethylamino)-5-oxopentyl, 2-amino-3-(1H-indol-2-yl)-1-oxopropyl, 3-(1,2-dimethyl-1H-imidazol-3-ium-3-yl)propyl, 10-(1,2-dimethyl-1H-imidazol-3-ium-3-yl)decyl, 10-(1-methyl-1H-imidazol-3-ium-3-yl)decyl, 3-(thiazol-3-ium-3-yl)propyl, 3-aminopropyl, 3-cyclohexylpropyl, 3-phenylpropyl, 3-(trimethylammonio)propyl, 3-(1-methylpyrrolidinium-1-yl)propyl, 3-(2-methylthiazol-3-ium-3-yl)propyl, 3-(benzo[d]thiazol-3-ium-3-yl)propyl, 3-(tetrahydro-1H-thiophenium-1-yl)propyl, 3-(3-methyl-1H-imidazol-3-ium-1-yl)propyl, 3-(1-methyl-1H-imidazol-3-ium-3-yl)propyl, 3-(3-(3-aminopropyl)-1H-imidazol-3-ium-1-yl)propyl, 3-(1-(3-aminopropyl)-1H-imidazol-3-ium-3-yl)propyl, 3-(3-(5-trimethylammonio)pentyl)-1H-imidazol-3-ium-1-yl)propyl, 3-(1-(5-trimethylammonio)pentyl)-1H-imidazol-3-ium-3-yl)propyl, 3-(3-decyl-1H-imidazol-3-ium-1-yl)propyl, 3-(1-decyl-1H-imidazol-3-ium-3-yl)propyl, 3-(3-(9-(3-methyl-1H-imidazol-3-ium-1-yl)nonyl)-1H-imidazol-3-ium-1-yl)propyl, 3-(1-(9-(1-methyl-1H-imidazol-3-ium-3-yl)nonyl)-1H-imidazol-3-ium-3-yl) propyl, 3-(1-(9-(3-methyl-1H-imidazol-3-ium-1-yl)nonyl)-1H-imidazol-3-ium-3-yl)propyl, 3-(3-(9-(1-methyl-1H-imidazol-3-ium-3-yl)nonyl)-1H-imidazol-3-ium-1-yl) propyl, 4-(3-decyl-1H-imidazol-3-ium-1-yl)butyl, 4-(1-decyl-1H-imidazol-3-ium-3-yl)butyl, 10-(1-decyl-2-methyl-1H-imidazol-3-ium-3-yl)decyl, 10-(3-decyl-2-methyl-1H-imidazol-3-ium-1-yl)decyl, 3-(1,2-dimethyl-1H-imidazol-3-ium-3-yl)propyl, 3-(2,3-dimethyl-1H-imidazol-3-ium-1-yl) propyl, 10-(2,3-dimethyl-1H-imidazol-3-ium-1-yl)decyl, 10-(1,2-dimethyl-1H-imidazol-3-ium-3-yl)decyl, 10-(1-methyl-1H-imidazol-3-ium-3-yl)decyl, 10-(3-methyl-1H-imidazol-3-ium-1-yl)decyl, 10-(1-butyl-1H-imidazol-3-ium-3-yl)decyl, 10-(3-butyl-1H-imidazol-3-ium-1-yl)decyl, 10-(pyridinium-1-yl)decyl, 10-(1-methylpyrrolidinium-1-yl)decyl, naphthalen-2-ylmethyl, naphthalen-1-ylmethyl, a ligand of formula 4

$$*-R_{46}-R_{47}-R_{48} \quad (4)$$

or a combination thereof, wherein $R_{46}$ is decylene, $R_{47}$ is 1,3-bis(1-methylpiperidin-4-yl)propane, and $R_{48}$ is decyl.

In the above ligands having protected amino groups, the protecting group is independently —C(O)OR$_{49}$, —C(O)R$_{50}$, wherein $R_{49}$ is alkyl or aryl, and $R_{50}$ is amino, hydrogen, alkyl, or haloalkyl. Protecting groups are well known in the art, and those known in the art may be used.

The amine polymers having a portion of the nitrogen atoms of the amine polymer substituted with a ligand can have about 5 mole % to about 60 mole % ligand based on the moles of amine monomer, about 5 mole % to about 50 mole % ligand based on the moles of amine monomer, or about 10 mole % to about 30 mole % ligand based on the moles of amine monomer.

The ratio of primary, secondary, and tertiary amines can be calculated by assuming complete reaction between the amine monomer and the crosslinking monomer and comparing the number of moles of the amine monomer and the crosslinking monomer along with the number of possible reaction sites on the crosslinking monomer. For example, when the amine polymer is N,N,N',N'-tetrakis(3-aminopropyl)-1,4-butanediamine (BTA), the amine has two tertiary amines and four primary amines before reacting with a crosslinking monomer. If the crosslinking monomer is dibromodecane and the mole ratio of BTA to dibromodecane is 1 to 1, two of the primary amine atoms will react with the crosslinking monomer to convert two of the primary amines to two secondary amines. Thus, the ratio of the primary to secondary to tertiary amines is 1 to 1 to 1.

Also, the amine polymers of the invention can bind various bile acids such that the concentration of bound taurocholic acid is greater than 1.5 mmol/g polymer and the concentration of unbound taurocholic acid is less than 1.0 mmol/g polymer when the polymer is placed in a buffer solution having a 2.5 mM taurocholic acid concentration at 37° C. and the concentration of bound taurocholic acid is greater than 5.0 mmol/g polymer and the concentration of unbound taurocholic acid is greater than 4.0 mmol/g polymer when the polymer is placed in a buffer solution having a taurocholic acid concentration of at least 10 mM at 37° C. Additionally, the amine polymers of the invention can bind bile acids such that the concentration of bound glycodeoxycholate is greater than 1.0 mmol/g polymer and the concentration of unbound glycodeoxycholate is less than 0.1 mmol/g polymer when the polymer is placed in a buffer solution having a 1.25 mM glycodeoxycholate concentration at 37° C. and the concentration of bound glycodeoxycholate is greater than 6.0 mmol/g polymer and the concentration of unbound glycodeoxycholate is greater than 2.0 mmol/g polymer when the polymer is placed in a buffer solution having a glycodeoxycholate concentration of at least 10 mM at 37° C.

Further, the amine polymer can be useful as a bile acid sequestrant, wherein, in a buffer solution at 37° C. containing less than 2.6 mM taurocholic acid, the amine polymer binds more of the acid than sevelamer and in a buffer solution at 37° C. containing more than 5.0 mM taurocholic acid the amine polymer binds more bile acid that colesevelam. The amine polymer can have the structure of any one of the amine polymers disclosed herein. Specifically, the amine polymer is derived from the polymerization of an amine monomer and a crosslinking monomer wherein the amine monomer comprises N,N,N',N'-tetrakis(3-aminopropyl)-1,12-diaminododecane and the crosslinking monomer comprises 1,3-dichloropropanol.

Figure 1B:
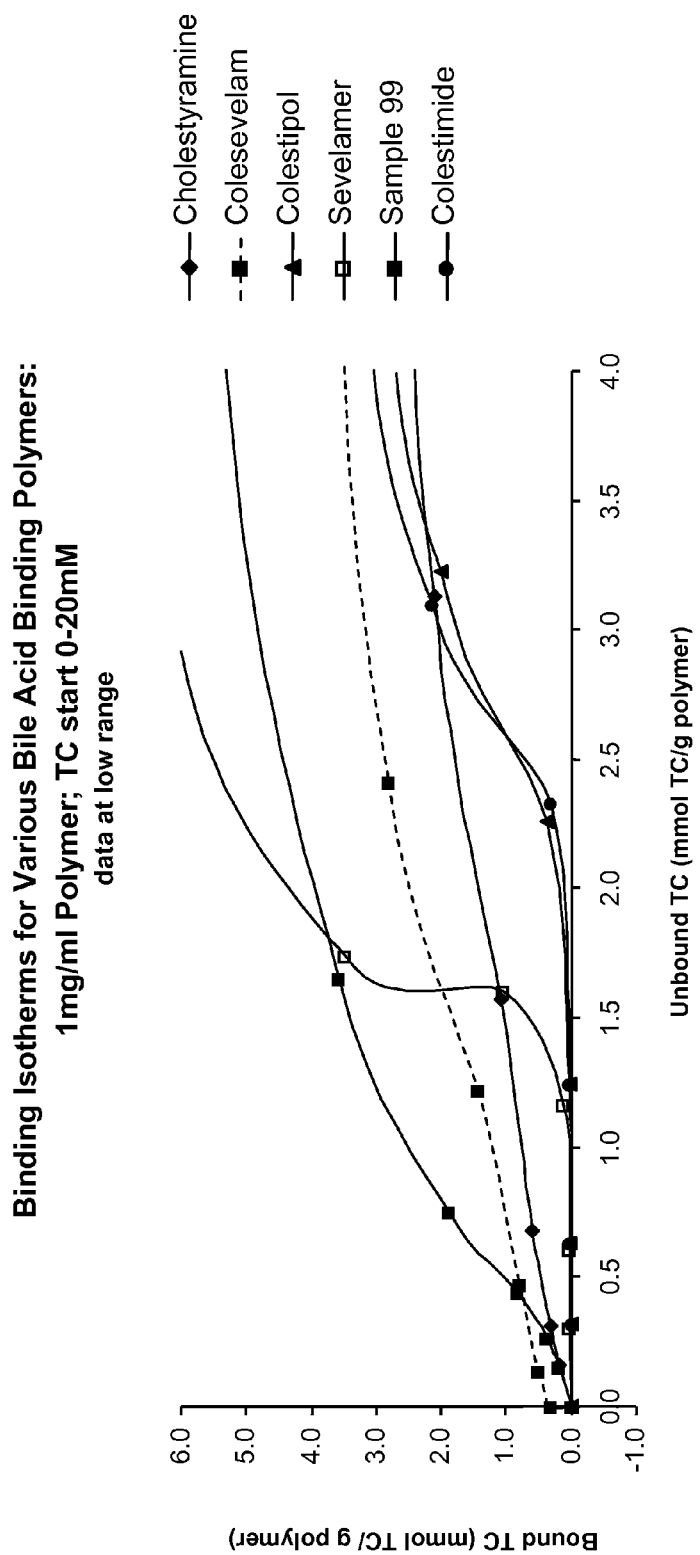
FIG. 1B is the same graph as FIG. 1A at taurocholic acid concentrations up to 5 mM.
Figure 2A:
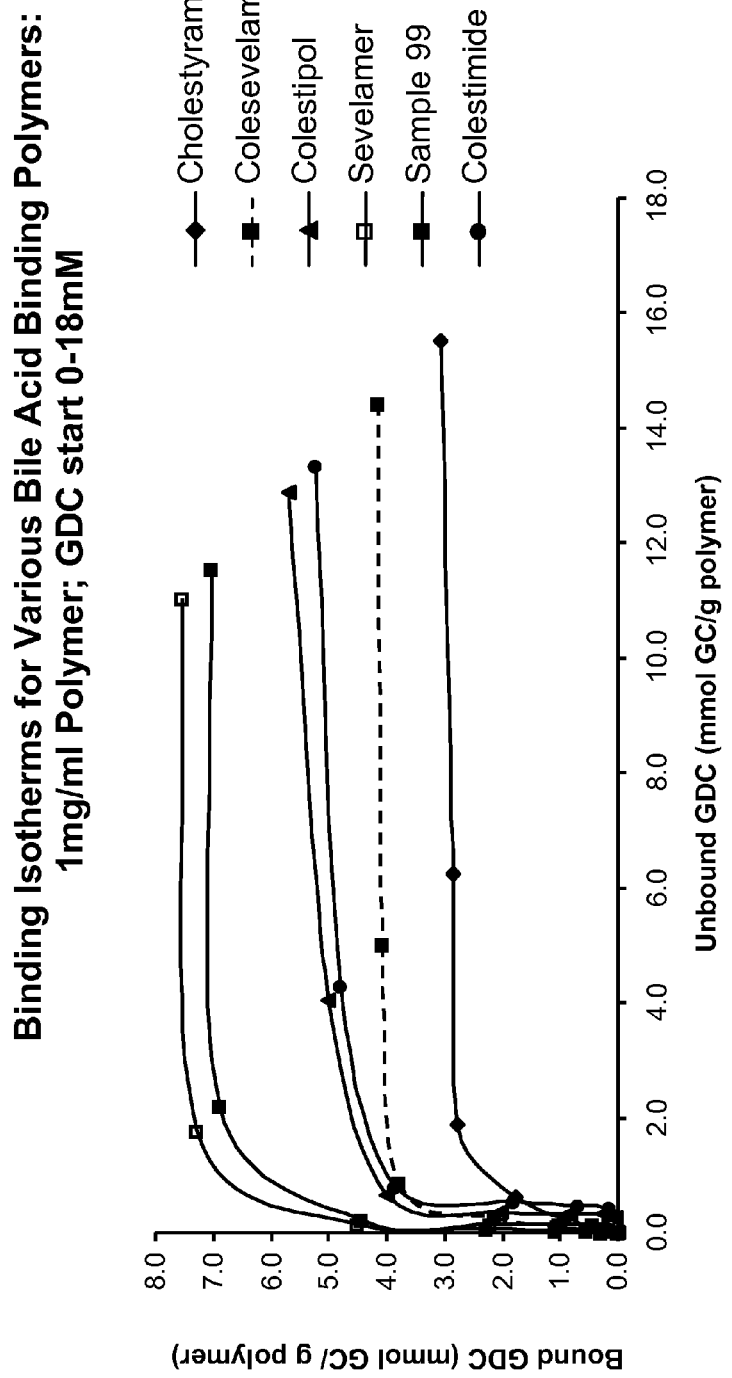
FIG. 2A is a graph of the unbound glycodeoxycholic acid concentration versus the bound taurocholic acid concentration for various bile acid binders at glycodeoxycholic acid concentrations up to 20 mM.
Figure 2B:
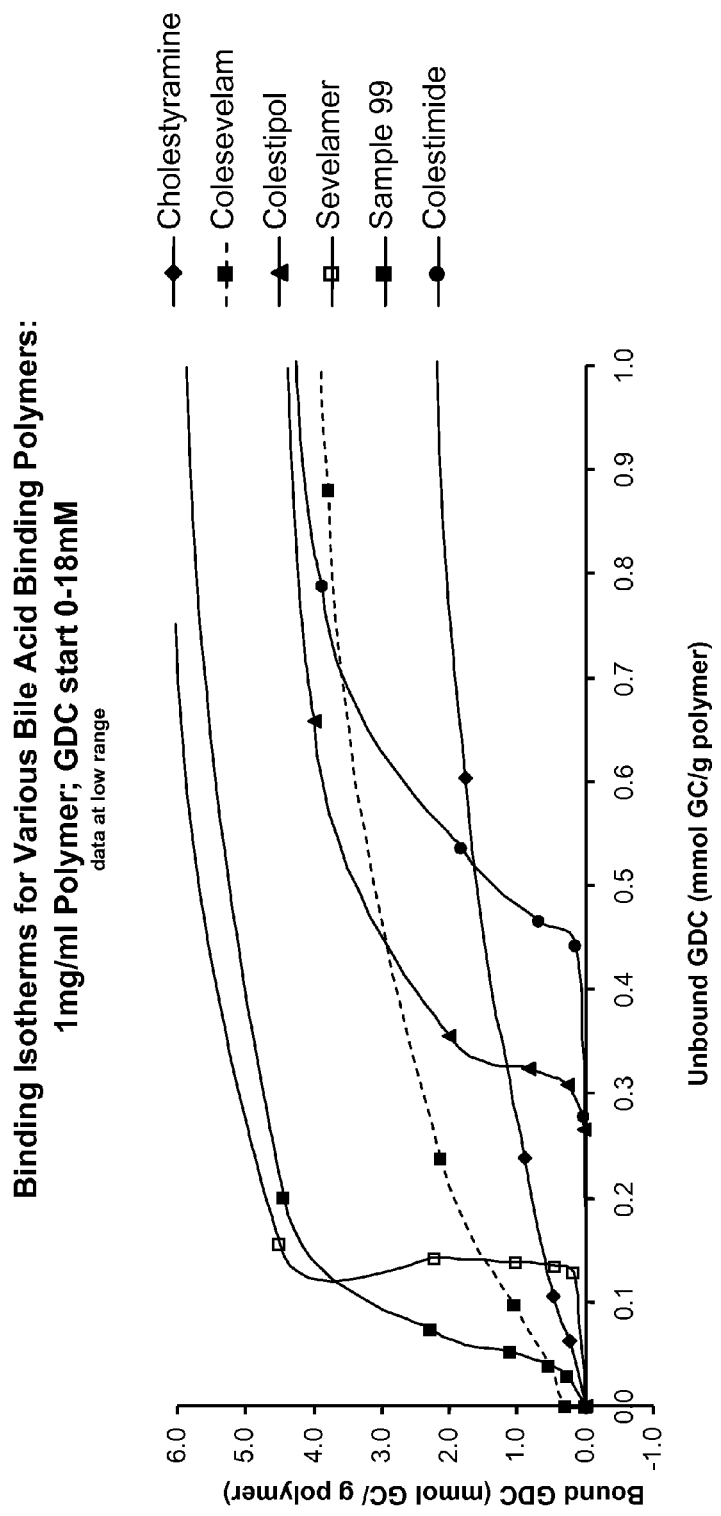
FIG. 2B is the same graph as FIG. 2A at glycodeoxycholic acid concentrations up to 5 mM.

Without wishing to be bound by any particular theory, the invention herein uses a combination of positive charge density and hydrophobicity to achieve unexpected bile acid binding affinity, binding capacity, retention and removal. The charge density comes from a concentration of positively charged nitrogen atoms that are separated by a hydrophobic segment. Hydrophobicity is expressed by the calculated log P, as discussed herein. Further, as shown in FIGS. 1 and 2, the present invention has a unique combination of high binding affinity at low concentrations of bile acids and high binding capacity for bile acids at high concentrations of bile acids. More specifically, at 37° C., in a buffer solution containing less than 2.6 mM taurocholic acid, the polymers of the present invention bound more bile acid than sevelamer, and in a buffer solution containing more than 5.0 mM taurocholic acid, the polymers of the present invention bound more bile acid than colesevelam. Even more specifically, at 37° C., in a buffer solution containing less than 2.0 mM taurocholic acid, the polymers of the present invention bound more bile acid than sevelamer, and in a buffer solution containing more than 7.0 mM taurocholic acid, the polymers of the present invention bound more bile acid than colesevelam. Yet more specifically, at 37° C., in a buffer solution containing less than 1.5 mM taurocholic acid, the polymers of the present invention bound more bile acid than sevelamer, and in a buffer solution containing more than 10.0 mM taurocholic acid, the polymers of the present invention bound more bile acid than colesevelam. In some embodiments, the Langmuir equation known to those of skill in the art can be used in a linear regression analysis to determine equilibrium binding constants that reflect the greater affinity than sevelamer and the greater binding capacity than colesevelam.

FIGS. 1 and 2 show graphs of the data from Example 50 plotted as the unbound bile acid in mmol bile acid per g polymer on the x-axis and bound bile acid in mmol bile acid per g polymer on the y-axis. With this data graphed in this manner, the trend of the bile acid binding shows that the polymer of Sample 99 binds more bile acid than the commercial bile acid sequestrants with the exception of colesevelam at low bile acid concentrations (i.e., less than 2.5 mM) and binds more bile acid than all the commercial bile acid sequestrants except sevelamer at high bile acid concentrations (i.e., greater than 5.0 mM).

Further, the calculated log P (c Log P) of at least one of $R_{10}$ or $R_{30}$ of Formula 1 of the amine polymers can be greater than 4, 4.5, 5, 5.5, 6, 6.5, 7, 7.5, or 8. The calculated log P (c Log P)(Clog P) is determined by drawing the structure of the crosslinker without the leaving groups in Chemdraw Ultra 11.0 (CambridgeSoft, Cambridge Mass.) and replacing the leaving groups with hydrogen, and selecting the chemical properties tool to calculate the c Log P. For example, for the crosslinker 1,10-dibromodecane, one would enter the structure of decane into Chemdraw and select "show chemical properties" from the "view" toolbar to calculate its c Log P as 5.984. If the crosslinker is a ring structure that opens during crosslinking, such as epichlorohydrin, the c Log P is determined by drawing the ring-opened structure as shown below for epichlorohydrin:

For example, the calculated log P (c Log P) for various segments is detailed in Table 2.

TABLE 2

Calculated log P (cLog P) of selected segments

| Segment | Calculated log P |
|---|---|
| 2,3-butanediol structure | −0.7512 |
| diether diol structure | −0.5108 |
| isopropanol structure | 0.0740 |
| 2-butanol structure | 0.603 |
| 2,6-heptanediol structure | 0.512 |
| — | 1.752 |
| propyl structure | 2.28 |
| diketone structure | 1.006 |
| 2,8-nonanediol structure | 1.57 |
| butyl structure | 2.81 |

TABLE 2-continued

Calculated log P (cLog P) of selected segments

| Segment | Calculated log P |
|---|---|
| (C7 alkyl chain) | 3.339 |
| (diketone with C7 chain) | 2.064 |
| (C8 alkyl chain) | 3.868 |
| (C9 alkyl chain) | 4.397 |
| (diketone with longer chain) | 3.122 |
| (C10 alkyl chain) | 4.926 |
| (C11 alkyl chain) | 5.455 |
| (C11 alkyl chain) | 4.67 |
| (C12 alkyl chain) | 5.984 |
| (C14 alkyl chain) | 7.042 |
| (C16 alkyl chain) | 8.1 |
| (C18 alkyl chain) | 9.158 |

One method for preparing the amine polymers described herein is to contact an amine monomer having six, seven or eight possible reaction sites or an amine monomer of Formulae 2 or 3 with a crosslinking monomer. The amine monomer and crosslinking monomer can be contacted in the presence of a solvent; the solvent is preferably a polar aprotic solvent (e.g., dimethyl formamide (DMF), dimethyl sulfoxide (DMSO), N,N-dimethylacetamide (DMAC), tetrahydrofuran (THF), methyltetrahydrofuran, dimethylsulfoxide), 1,4-dioxane, 2-pyrrolidinone, or 1-methyl-2-pyrrolidinone. Polar protic solvents can also be used (e.g. methanol, ethanol, isopropyl alcohol, butanol, pentanol, or ethylene glycol). Once the amine monomer and the crosslinking monomer are contacted, the reaction mixture is heated to from about 40° C. to about 120° C. or at about 60° C. to 70° C. for about 12 to 24 hours. After the reaction is complete, the polymer gel product is washed with a basic solution, followed by water, and then lyophilized until dry.

Monomers of the amine as defined in formulas 2 and/or 3 can be prepared using methods known to those of skill in the art, with specific examples of such syntheses in the examples below. In general, however, the desired core ($R_3$) is prepared or commercially available and converted into a tetranitrile using known synthetic routes. For certain embodiments, an alkyl tetranitrile is prepared by the addition of acrylonitrile to an alkyldiamine via a Michael-type reaction. An alkyl tetranitrile can also be prepared by the addition of a dihaloalkyl to 3,3'-iminodipropionitrile. Another approach of preparing an alkyl tetranitrile is via the synthesis of the primary amine protected form of bis(3-aminopropyl)amine, (e.g., bis(3-(t-butoxycarbonylamino)propyl)amine or bis((3-benzyloxycarbonylamino)propyl)amine) followed by the addition of the dihaloalkane, and subsequent deprotection (see for example, Protective Groups in Organic Synthesis by Theodore Greene, Wiley-Interscience, 1999). Thereafter, the alkyl tetranitrile intermediate is then hydrogenated. Hydrogenation can be accomplished using a variety of techniques including Raney-nickel and/or Raney-cobalt catalysts followed by washing. A general hydrogenation procedure with Raney cobalt would combine the alkyl tetranitrile with hydrogen at a pressure from 100 to 5000 psi (e.g., about 1300-1500 psi) with or without $NH_3$ (e.g., about 40 psi $NH_3$) at a temperature of 50 to 120° C. (e.g., about 100° C.) in a solvent (e.g., water, methanol, ethanol, toluene, etc.) with adequate stirring and reaction time.

The amine polymers of the invention have various chemical, structural and physical properties that contribute to their capacity for binding bile acids and/or their affinity for binding bile acids preferentially over fatty acids, phosphates and/or other compounds present in the gastrointestinal tract.

The amine polymer can be administered in the form of a salt, or as a partial salt, or as salt free base. The "salt" has nitrogen atoms or groups in all or some of the repeat units that are protonated to create a positively charged nitrogen atom associated with a negatively charged counterion. The anionic counterions can be selected to minimize adverse effects on the patient. Examples of suitable counterions include $Cl^-$, $Br^-$, $CH_3OSO_3^-$, $HSO_4^-$, $SO_4^{2-}$, nitrate, $HCO_3^-$, $CO_3^{2-}$, acetate, lactate, phosphate, hydrophosphate, fumarate, malate, pyruvate, malonate, benzoate, glucuronate, oxalate, acetylglycinate, succinate, propionate, butyrate, ascorbate, citrate, tartrate, maleate, folate, an amino acid derivative, a nucleotide, a lipid, a phospholipid, or a combination thereof. The counterions can be the same as, or different from, each other. For example, the reaction product can contain two different types of counterions. In most cases, not all of the nitrogen atoms will be in a salt form, with the percent of nitrogen atoms in a salt form being dictated by certain properties, such as flowability, storage time, and weight.

To determine the in vitro binding affinity for bile salts under conditions that are intended to mimic in certain respects those conditions found in the lower small intestine, the amine polymer is analyzed using assay A. The A assay combines the polymer to be analyzed in a desired concentration with a solution that mimics certain conditions present in the lower small intestine as described in Protocol 1 in the examples. After a period of time, the polymers are recovered by centrifugation and the supernatants are sampled, filtered to remove any remaining particulates and assayed for ion concentrations by liquid chromatography (LC). By comparing the equilibrium concentrations of glycocholate ($GC_{eq}$), glycodeoxycholate ($GDC_{eq}$), oleyl glycerol ($OG_{eq}$) and/or oleic acid ($OA_{eq}$) in the presence of the polymer to their concentrations in test solution in the absence of the polymer, the amount of each component bound under these experimental conditions in mmoles/g polymer is calculated. The in vitro bile salt binding affinity under the conditions of the A assay in Protocol 1 results in a maximum of about 0.75 mmol/gram polymer. Thus, the in vitro bile salt binding affinity for the amine polymers of this invention is from about 0.34 to about 0.75 mmol/gram polymer, particularly from about 0.46 to about 0.75 mmol/gram polymer, and more particularly, from about 0.55 to about 0.75 mmol/gram polymer when measured in the Assay A solution. Further, in some embodiments, the in vitro bile salt binding affinity for the amine polymers of this invention is greater than 0.55 mmol/gram polymer, greater than 0.60 mmol/gram polymer, or greater than 0.65 mmol/gram polymer.

In some cases the concentration of phosphate ions was also determined on a strong anion exchange column by liquid chromatography using a basic mobile phase in order to measure the phosphate binding affinity. The polymers of the invention bind phosphate in vitro in an amount of less than 0.3 mmol/gram of polymer, particularly less than 0.2 mmol/gram of polymer, more particularly up to about 0.15 mmol/gram polymer, and even more particularly, up to about 0.10 mmol/gram polymer when measured using a B assay.

To determine the in vitro binding capacity for bile salts under conditions that are intended to mimic in certain respects those conditions found in the upper small intestine after a meal, the amine polymer is analyzed using Assay B. In Assay B, the polymer to be analyzed is combined in a desired concentration with a solution that mimics certain conditions present in the upper small intestine as described in Protocol 2 in the examples. The same general procedure as described above was used to calculate the amount of each component bound. The in vitro bile salt binding capacity under the conditions of the B assay in Protocol 2 results in a maximum of about 3.7 mmol/gram polymer. Thus, the in vitro bile salt binding capacity for the amine polymers is from about 0.28 to about 3.7 mmol/gram polymer, particularly from about 2.22 to about 3.7 mmol/gram polymer, and more particularly from about 3 to about 3.7 mmol/gram polymer when measured in the assay B solution.

To determine the in vivo binding retention for bile salts, the amine polymer is analyzed in a hamster model. The hamster model provides a complex and relevant measure of the polymer's binding capacity for bile acids, its binding affinity for bile acids over other anions, and its ability to retain bound bile acids and to increase the excretion of bile acids and bile acids metabolites from the gastrointestinal tract into the feces. Preferably, Golden Syrian hamsters may be used as they have a similar bile acid profile to that of humans. Male Golden Syrian hamsters are acclimated and then placed on a high-fat, high-sucrose western diet, D12079B (Research Diet, New Brunswick, N.J.) for several days before the study is started. The amine polymers to be analyzed are blended into western diet at the desired dose to prepare the test diets. The hamsters are held in individual metabolic cages allowing the separation and collection of feces. Animals from the test groups are switched to the test diets, while animals from the untreated group are kept on western diet without added amine polymer. Food intake is measured for four consecutive days. For each hamster, feces from the last three days of the treatment period are collected, pooled, lyophilized, and then homogenized by grinding in a mortar and pestle. The feces samples are then extracted for fecal bile salt analysis. In some cases, a baseline treatment period is conducted where all groups of animals are placed in metabolic cages as described above and fed only on western diet without added test article. Feces are collected as described above and the effect of the amine polymer on bile salt fecal excretion is determined by comparing baseline versus treatment periods. Otherwise, the effect of amine polymers on bile salt fecal excretion is determined by comparing untreated versus test groups. Hamster fecal bile salts are analyzed as described in the examples. The amine polymers can have a calculated in vivo binding capacity at least 25%, 50%, 75%, 100%, 125%, 150%, 175% or 200% greater than colesevelam hydrochloride when measured at a dosage of 0.5% of the total feed intake in male Golden Syrian hamsters fed a Western diet.

The amine polymers can have a calculated in vivo bile salt binding capacity of at least about 0.35 mmol bile salt/gram of polymer when measured in humans. The amine polymers can have an in vivo binding capacity in a human of at least 0.35 mmol bile salt per gram of polymer, at least 0.4 mmol bile salt per gram of polymer, at least 0.5 mmol bile salt per gram of polymer, at least 0.6 mmol bile salt per gram of polymer, or more.

Polymers of the invention are crosslinked materials, meaning that they do not generally dissolve in solvents however they can swell with solvents or absorb the solvent. As used herein, "swelling ratio" refers to the number of grams of solvent taken up by one gram of crosslinked polymer when equilibrated in an aqueous environment. The swelling ratio is sensitive to the polymer solvent interaction parameter as described in Flory Huggins (Flory P. J. "Principles of Polymer Chemistry, Cornell Ithica Pub. 1953). When more than one measurement of swelling is taken for a given polymer, the mean of the measurements is taken to be the swelling ratio. The swelling ratio in water, or in physiological isotonic buffer, which is representative of the gastrointestinal tract (for example United States Pharmacopeia Simulated Intestinal Fluid or Simulated Gastric Fluid), is typically in the range of about 1 to about 10 g of swelling solution (solvent)/g of polymer, particularly about 2 to 6, and more particularly about 2 to about 4. The counterion content of the polymer can affect the swelling ratio, in the examples listed below, a chloride counterion is used, and the chloride content is stated. The counterion content can be as much as 25 wt. % of the total weight of the polymer and as little as <1% of the total weight of the polymer.

The amine polymers can be particles having a mean diameter from about 10 microns to about 200 microns. In some of the embodiments, the amine polymer particles are substantially spherical beads. These beads can have a mean diameter from about 10 microns to about 200 microns. As used herein, the term "substantially" means generally rounded particles having an average aspect ratio of about 1.0 to about 2.0. Aspect ratio is the ratio of the largest linear dimension of a particle to the smallest linear dimension of the particle. Aspect ratios may be easily determined by those of ordinary skill in the art. This definition includes spherical particles, which by definition have an aspect ratio of 1.0. In some embodiments, the particles have an average aspect ratio of about 1.0, 1.2, 1.4, 1.6, 1.8 or 2.0. The particles may be round or elliptical when observed at a magnification wherein the field of view is at least twice the diameter of the particle.

The substantially spherical beads can be prepared using methods known to a person skilled in the art. For example, a preferred mode of synthesis is a heterogeneous process. Such processes are also referred to as polymerization in dispersed media and include direct or inverse suspension, emulsion, precipitation, dispersion or micro emulsion polymerization, reaction in aerosol or using bulk polymerization methods. In inverse suspension, the continuous phase can be selected from apolar solvents such as silicone, toluene, benzene, hydrocarbon solvents or oils, halogenated solvents, supercritical carbon dioxide, and the like. The discrete phase for the inverse suspension system comprises solubilizing the monomer and crosslinker in water; this can be achieved by the addition of an acid such as hydrochloric acid to form the amine salt, which renders the organic amine substantially more water soluble and dispersing the amine solution in a water-immiscible solvent to form an emulsion. With a direct suspension or emulsion process, water can be used as the continuous phase, although salt brines are also useful to "salt out" the monomer and crosslinker into the discrete phase, as described in U.S. Pat. No. 5,414,068. The monomers can be dispersed either neat or as a solution in the continuous phase using a cosolvent. The crosslinking monomer can be added to the reaction in a semicontinuous fashion (staged addition) allowing the polymerization reaction to occur. Isolation of the beads can be carried out by filtration, washing and drying. Size can be further controlled or modified by reduction processes such as extrusion and grinding.

The yield and efficiency of the reaction of crosslinker and amine monomer can be increased by the addition of a Dean-Stark process to a suspension polymerization reaction. During the Dean-Stark process water is removed, which concentrates the reaction mixture (e.g., amine and crosslinker). Without being limited by any particular theory, the concentrating process allows any reactive chain ends on the growing network to react, driving the reaction to completion. Generally, the temperature also rises as the water is removed. Increased efficiency in the reaction may allow for the use of lower amounts of crosslinker and may produce a product having higher purity.

Thus, when preparing polymer beads, the ratio of the crosslinker to amine monomer can change depending on the process conditions (e.g., salting out or Dean-Stark conditions), monomer purity and the desired physical properties (e.g., swelling ratio, particle size, etc.). In various embodiments, the mole ratio of the amine monomer (e.g., of formula 2 or formula 3) to the crosslinking monomer is from about 1:1 to about 1:5; preferably, from about 1:1 to about 1:3 and more specifically from about 1:1.1 to about 1:3.

Polymers can be obtained by methods known to those in the art, examples of which are illustrated in the Examples herein. The crosslinked amine polymer particle is generally a reaction product of a reaction mixture that is subjected to reaction conditions. The reaction mixture may also generally contain components that are not chemically incorporated into the product. The reaction mixture typically comprises monomers.

In general, the reactions are conducted such that a polymer network is generated, which is insoluble but can be solvated into a gel. When the interpenetrating solvent is water, the insoluble material is described as a hydrogel. The reaction is carried either in solution, in bulk (i.e. using the neat monomers and crosslinking compounds) or in dispersed media. The reaction may start with the introduction of for example, temperature change or irradiation. In general amine polymers can be prepared by chain growth or step growth. Step growth polymerization involves the polymerization of monomers that contain unsaturated functional groups, including radical polymerization, cationic polymerization and anionic polymerization. Step growth polymerization involves the reaction of bifunctional or polyfunctional monomers that grow via, dimers, trimers to longer oligomers. When using a polyfunctional amine containing monomer, the growth results in a branched polymer. Network formation occurs when the polymer chains react with each other. Parameters that effect the network formation reaction include temperature, solvent choice, the concentrations of monomers and crosslinkers, and the ratio of the monomer to the crosslinking monomer. For polyamines such as that formed from an amine monomer and multi functional alkyl bromide crosslinker, desirable solvents have a high dielectric constant and include the following, but are not limited to, water, methanol, (and alcoholic solvents), N, N-dimethylformamide, methylpyrrolidone, dimethylsulfoxide, tetrahydrofuran, methyltetrahydrofuran and acetonitrile. The addition of a base maybe desired in some cases.

Polymerization reactions to prepare the amine polymers include preparing an aqueous solution of the amine monomer, optionally with a surfactant, and adding an organic phase containing an organic solvent and optionally, a surfactant, to the aqueous phase. The crosslinker then can be added in a batch or a semi-continuous fashion. For example, the crosslinker can be added to the polymerization all at once or can be added slowly over a period of time.

The amine polymer particles have a mean diameter of from about 10 µm to about 200 µm. Specific ranges are where the amine polymer particles have a mean diameter of from about 20 µm to about 200 µm, from about 20 µm to about 150 µm, or from about 20 µm to about 125 µm. Other ranges include from about 35 µm to about 150 µm, from about 35 µm to about 125 µm, from about 50 µm to about 125 µm, or from about 50 µm to about 100 µm. Particle sizes, including mean diameters, distributions, etc. can be determined using techniques known to those of skill in the art. For example, U.S. Pharmacopeia (USP)<429> discloses methods for determining particle sizes.

Various amine polymer particles also have less than about 4 volume percent of the particles that have a diameter of less than about 10 µm; particularly, less than about 2 volume percent of the particles that have a diameter of less than about 10 µm; more particularly, less than about 1 volume percent of the particles that have a diameter of less than about 10 µm; and even more particularly, less than about 0.5 volume percent of the particles that have a diameter of less than about 10 µm. In other cases, specific ranges are less than about 4 volume percent of the particles that have a diameter of less than about 20 µm; less than about 2 volume percent of the particles that have a diameter of less than about 20 µm; less than about 1 volume percent of the particles that have a diameter of less than about 20 µm; less than about 0.5 volume percent of the particles that have a diameter of less than about 20 µm; less than about 2 volume percent of the particles that have a diameter of less than about 30 µm; less than about 1 volume percent of the particles that have a diameter of less than about 30 µm; less than about 1 volume percent of the particles that have a diameter of less than about 30 µm; less than about 1 volume percent of the particles that have a diameter of less than about 40 µm; or less than about 0.5 volume percent of the particles that have a diameter of less than about 40 µm. In various embodiments, the amine polymer has a particle size distribution wherein not more than about 5 volume % of the particles have a diameter less than about 30 µm (i.e., D(0.05)<30 µm), not more than about 5 volume % of the particles have a diameter greater than about 250 µm (i.e., D(0.05)>250 µm), and at least about 50 volume % of the particles have a diameter in the range from about 70 to about 150 µm.

The particle distribution of the amine polymer can be described as the span. The span of the particle distribution is defined as (D(0.9)−D(0.1))/D(0.5), where D(0.9) is the value wherein 90% of the particles have a diameter below that value, D(0.1) is the value wherein 10% of the particles have a diameter below that value, and D(0.5) is the value wherein 50% of the particles have a diameter above that value and 50% of the particles have a diameter below that value as measured by laser diffraction. The span of the particle distribution is typically from about 0.5 to about 1, from about 0.5 to about 0.95, from about 0.5 to about 0.90, or from about 0.5 to about 0.85. Particle size distributions can be measured using Niro Method No. A 8 d (revised September 2005), available from GEA Niro, Denmark, using the Malvern Mastersizer.

It has now been found that when using the amine polymers and the compositions of the present invention, a once-a-day dose is substantially equivalent to a twice-a-day dose, which is also substantially equivalent to a three-times-a-day dose. Generally, the once per day or twice per day administration of a daily amount of the polymer or the composition has a bile acid removal that is not statistically significantly different from the removal of the same polymer or composition at the same daily amount administered three times per day.

Additionally, the invention is directed to methods of removing bile acids from an animal subject by administering an amine polymer or a pharmaceutical composition comprising an amine polymer, wherein less than 25% of subjects taking the polymer or composition once per day experience mild or moderate gastrointestinal adverse events at a dose of 6.0 grams/day or less. Gastrointestinal adverse events may include flatulence, diarrhea, abdominal pain, constipation, stomatitis, nausea and/or vomiting. In some aspects, the polymer or composition is administered twice a day and less than 25% of subjects taking the polymer or composition twice per day experience mild or moderate gastrointestinal adverse events. In some instances, the subjects taking the polymer or composition once per day or twice per day experience no severe gastrointestinal adverse events. The amine polymers or pharmaceutical compositions of the present invention have about 50% or more tolerability as compared to the same polymer or composition of the same daily amount administered three times a day. For example, for every two patients in which administration of the polymer three times a day is well tolerated, there is at least one patient in which administration of the polymer once a day or twice a day is well tolerated.

When administration is well tolerated, there should be little or no significant dose modification or dose discontinuation by the subject. In some embodiments, well tolerated means there is no apparent dose response relationship for gastrointestinal adverse events. In some of these embodiments, well tolerated means that the following gastrointestinal adverse effects are not reported from a statistically significant number of subjects, including those effects selected from the group consisting of flatulence, diarrhea, abdominal pain, constipation, stomatitis, nausea and vomiting.

In other embodiments, the present invention provides a method of removing bile acids from the gastrointestinal tract of an animal subject in need thereof, comprising administering an effective amount of an amine polymer or a composition comprising an amine polymer, wherein the polymer or composition is as well tolerated as administering substantially the same amount of the same polymer or composition three times per day. In some instances, the subject is experiencing hypercholesteremia and thus the method treats hypercholesteremia. In other instances, the method lowers serum cholesterol.

Without wanting to be bound by any particular theory, the tolerability of the polymer or composition comprising the polymers results from physical properties that the amine polymers may possess, including a viscosity when hydrated and sedimented of from about 10,000 Pa·s to about 2,500,000 Pa·s, from about 10,000 Pa·s to about 2,000,000 Pa·s, from about 10,000 Pa·s to about 1,500,000 Pa·s, from about 10,000 Pa·s to about 1,000,000 Pa·s, from about 10,000 Pa·s to about 500,000 Pa·s, or from about 10,000 Pa·s to about 250,000 Pa·s, from about 30,000 Pa·s to about 3,000,000 Pa·s, from about 30,000 Pa·s to about 2,000,000 Pa·s, or from about 30,000 Pa·s to about 1,000,000 Pa·s, the viscosity being measured at a shear rate of 0.01 sec$^{-1}$. This viscosity is measured using a wet polymer prepared by mixing the polymer thoroughly with a slight excess of simulated intestinal fluid (per USP <26>), allowing the mixture to sediment for 3 days at 37° C., and decanting free liquid from the sedimented wet polymer. The steady state shear viscosity of this wet polymer can be determined using a Bohlin VOR Rheometer (available from Malvern Instruments Ltd., Malvern, U.K.) or equivalent with a parallel plate geometry (upper plate of 15 mm diameter and lower plate of 30 mm diameter, and gap between plates of 1 mm) and the temperature maintained at 37° C.

The amine polymers may further have a hydrated and sedimented yield stress of from about 150 Pa to about 4000 Pa, from about 150 Pa to about 3000 Pa, from about 150 Pa to about 2500 Pa, from about 150 Pa to about 1500 Pa, from about 150 Pa to about 1000 Pa, from about 150 Pa to about 750 Pa, or from about 150 Pa to about 500 Pa, from about 200 Pa to about 4000 Pa, from about 200 Pa to about 2500 Pa, from about 200 Pa to about 1000 Pa, or from about 200 Pa to about 750 Pa. Dynamic stress sweep measurements (i.e., yield stress) can be made using a Reologica STRESSTECH Rheometer (available from Reologica Instruments AB, Lund, Sweden) or equivalent in a manner known to those of skill in the art. This rheometer also has a parallel plate geometry (upper plate of 15 mm diameter, lower plate of 30 mm diameter, and gap between plates of 1 mm) and the temperature is maintained at 37° C. A constant frequency of 1 Hz with two integration periods can be used while the shear stress is increased from 1 to $10^4$ Pa.

Amine polymers used in this invention may also have desirable compressibility and bulk density when in the form of a dry powder. Some of the particles of the amine polymers in the dry form have a bulk density of from about 0.8 g/cm$^3$ to about 1.5 g/cm$^3$, from about 0.82 g/cm$^3$ to about 1.5 g/cm$^3$, from about 0.84 g/cm$^3$ to about 1.5 g/cm$^3$, from about 0.86 g/cm$^3$ to about 1.5 g/cm$^3$, from about 0.8 g/cm$^3$ to about 1.2 g/cm$^3$, or from about 0.86 g/cm$^3$ to about 1.2 g/cm$^3$. The bulk density affects the volume of amine polymer needed for administration to a patient. For example, a higher bulk density means that a lower volume will provide the same number of grams of amine polymer. This lower volume can improve patient compliance by allowing the patient to perceive they are taking a smaller amount due to the smaller volume.

A powder composed of the particles of the amine polymer in dry form has a compressibility index of from about 3 to about 30, from about 3 to about 25, from about 3 to about 20, from about 3 to about 15, from about 3 to about 13, from about 5 to about 25, from about 5 to about 20, or from about 5 to about 15. The compressibility index is defined as 100*(TD-BD)/TD, wherein BD and TD are the bulk density and tap density, respectively. Bulk density (BD) and tapped density (TD) are used to calculate a compressibility index (CI). Standardized procedures for this measurement are specified as USP <616>. A quantity of the powder is weighed into a graduated cylinder. The mass M and initial (loosely packed) volume $V_o$ are recorded. The cylinder is then placed on an apparatus which raises and then drops the cylinder, from a height of 3 mm±10%, at a rate of 250 times (taps) per minute. The volume is measured after 500 taps and then again after an additional 750 taps (1250 total). If the difference in volumes after 500 and 1250 taps is less than 2%, then the final volume is recorded as $V_f$ and the experiment is complete. Otherwise, tapping is repeated in increments of 1250 taps at a time, until the volume change before and after tapping is less than 2%. The following quantities are calculated from the data:

Bulk Density (BD)=$M/V_o$

Tapped Density (TD)=$M/V_f$

Compressibility Index (CI, also called Carr's Index)=100*(TD−BD)/TD.

The powder form of the amine polymers settles into its smallest volume more easily than polymers conventionally used to treat hypercholesteremia. This makes the difference between the bulk density and the tap density (measured powder density after tapping a set number of times) from about 3% to about 30%, from about 3% to about 25%, from about 3% to about 20%, from about 3% to about 15%, from about 3% to about 10%, from about 5% to about 35%, from about 5% to about 30%, or from about 5% to about 20% of the bulk density.

The polymers and pharmaceutical compositions described herein retain a significant amount of the bound bile salts throughout the small intestine, and specifically, the bile salts bound by the polymer are not released prior to entry into the colon or excretion of the polymer in the feces. The term "significant amount" as used herein is not intended to mean that the entire amount of the bound bile salt are retained prior to fecal excretion or entry in to the colon. A sufficient amount of the bound bile salts are retained, such that a therapeutic and/or prophylactic benefit is obtained. For example, it may be sufficient for a polymer to retain bile acids such that there is a significant increase in the amount of bile acids entering the colon. The bile acids may then be released from the polymer but may still substantially be excreted either intact or as metabolites in the feces and thus for purposes of this invention have been sufficiently retained. Retention of bile acids may be measured by measuring the amounts of bile acids in the feces or in colonic aspirates or extracts above baseline levels (i.e., above the amount of bile acids retained in the feces when no polymer is administered to the animal subject). Particular amounts of bound bile salts that can be retained range from about 5% to about 100% above baseline levels. The polymer or pharmaceutical composition should retain at least about 5% of the bound bile salts, more particularly at least about 10%, even more particularly at least about 25% and most particularly at least about 50% of the bound bile salts above baseline levels. Retention of bile acids by the polymer can be calculated either directly by in vitro methods or indirectly by in vivo methods. The period of retention is generally during the time that the polymer or composition is being used therapeutically or prophylactically. When the polymer or composition is used to bind and remove bile salts from the gastrointestinal tract, the retention period is the time of residence of the polymer or composition in the gastrointestinal or the average residence time of the polymer or composition in the small intestine.

The polymers and pharmaceutical compositions described herein may result in an increased ratio of primary to secondary bile acids excreted in the feces. Bile acids may be characterized by their site of synthesis and modification; primary bile acids (for example cholic acid and chenodeoxycholic acid) are synthesized in hepatocytes from cholesterol and secondary or tertiary bile acids (for example deoxycholic acid and lithocholic acid) are the products of bacterial dehydroxylation in the terminal ileum and colon. Primary bile acids may be deconjugated and/or dehydroxylated to convert them to secondary or tertiary bile acids; for example deoxycholate (from cholate) and lithocholate (from chenodeoxycholate). A change in the ratio of excreted bile acids towards primary or unmetabolized bile acids is a measure of in vivo retention of bile acids by polymers. The amine polymers, in an in vivo measurement, can produce on average at least 11% primary bile acids in the feces based on total bile acids in the feces. In various embodiments, the amine polymers bind at least 15% or at least 20% primary bile acids in the feces based on the total bile acids in the feces.

Generally, the amine polymers are not significantly absorbed from the gastrointestinal tract. Depending upon the size distribution of the amine polymer particles, clinically insignificant amounts of the polymers may be absorbed. More specifically, about 90% or more of the polymer is not absorbed, about 95% or more is not absorbed, even more specifically about 97% or more is not absorbed, and most specifically about 98% or more of the polymer is not absorbed.

The amine polymers can be used to remove bile salts from an animal subject by administering an effective amount of the polymer to an animal subject in need thereof. The bile salts can be bound and retained by the amine polymer and then removed from the gastrointestinal tract in the feces. Further, the amine polymers can be used to reduce serum LDL-cholesterol, or serum non-HDL-cholesterol, in an animal subject. In some instances, the mean serum LDL can be decreased by at least 15%, at least 20%, at least 25%, at least 30% or more after 2, 4, 12, 26, 52 or more weeks of treatment with the amine polymer at a daily dose at which the subject experiences no severe gastrointestinal adverse events. In some instances, the daily dose of the amine polymer is about 6.0 g/day, 5.0 g/day, 4.0 g/day, 3.0, 2.5, or 2.0 g/day or less.

Further, the amine polymers can be administered to improve glycemic control in a human subject with Type II diabetes mellitus. Preferably, when a human subject with Type II diabetes mellitus is treated, glycated hemoglobin ($Hb_{A1c}$) can be decreased by at least 0.5%, at least 0.6%, at least 0.7%, at least 0.8%, at least 0.9%, at least 1.0% or more after 18, 26, 52 or more weeks of treatment with the amine polymer at a daily dose at which the subject experiences no severe gastrointestinal adverse events. In some instances, the daily dose of the amine polymer is about 6.0 g/day, 5.0 g/day, 4.0 g/day, 3.0, 2.5, or 2.0 g/day or less. Also, the fasting plasma glucose can be decreased by at least 14 mg/dL (0.8 mmol/L), at least 16 mg/dL (0.9 mmol/L), at least 18 mg/dL (1 mmol/L), at least 20 mg/dL (1.1 mmol/L) or more after 2, 4, 12, 26, 52 or more weeks of treatment with the amine polymer at a daily dose at which the subject experiences no severe gastrointestinal adverse events. In some instances, the daily dose of the amine polymer is about 6.0 g/day, 5.0 g/day, 4.0 g/day, 3.0, 2.5, or 2.0 g/day or less.

Further, the amine polymers can be used to ameliorate, treat or slow progression of Alzheimer's disease.

The amine polymers can also be used to treat non-alcoholic statohepatitis, cholestatic pruritus, irritable bowel syndrome with diarrhea (IBS-D), idiopathic bile acid malabsorption, genetic or congenital Fibroblast Growth Factor 19 (FGF19) deficiency or a combination thereof. When the amine polymers are used to treat cholestatic pruritus, they can be used in combination with an oral or topical antipruritic containing, for example, an antihistamine, a corticosteroid, a local anesthetic, a counterirritant, an opioid, an opioid receptor antagonist, or other therapies including but not limited to crotamiton, doxepin, mirtazapine, capsaicin, tacrolimus, linoleic acid, gabapentin, activated charcoal, thalidomide, naltrexone, erythropoietin, nicergoline, naltrexone, nalmefene, butorphanol, naloxone, rifampin, ondansetron, ursodeoxycholate, S-adenosyl-L-methionine, serotonin-selective reuptake inhibitors, phenobarbital, dronabinol, phototherapy, or a combination thereof.

When the amine polymers are used to treat IBS-D, they can be used in combination with antidiarrheals such as opiates, opioid or opioid analogs including loperamide, codeine, diphenoxylate, serotonin receptor antagonists such as alosetron, ramosetron and cilansetron, serotonin-selective reuptake inhibitors, tricyclic antidepressants such as amitriptyline and desipramine or drugs reducing the levels of serotonin (5-HT), antispasmodic drugs including anticholinergics such as hyoscyamine or dicyclomine, chloride secretion blockers such as crofelemer and probiotics.

As used herein, an animal subject can be a human or other mammal in need of either bile salt removal, reduction of serum LDL-cholesterol, or non HDL-cholesterol concentration, increase in HDL-C or improved glycemic control.

The methods, polymers and compositions described herein are suitable for removal of bile salts from an animal subject wherein the subject is in need of such bile salt removal. For example, patients experiencing hypercholesterolemia or hyperlipidemia benefit from such bile salt removal. The methods described herein are applicable to these patients regardless of the underlying condition that is causing the high serum cholesterol levels or need for bile acid removal.

The amine polymers can be administered once, twice, or three times a day. If the amine polymer is administered once a day, it may be administered just before, with, or just after the largest meal of the day. Also, if administered once a day, it may be administered in connection with the largest, on average during a twenty-four hour period, release of bile acids from the gall bladder, which is typically in the morning. Further, it is preferred that the amine polymer is administered at least 3 hours before or after any agents that might have an adverse interaction with the amine polymers.

The dosage regimen to treat hypercholesterolemia, atherosclerosis, diabetes, Alzheimer's disease, non-alcoholic steatohepatits, cholestatic pruritus, IBS-D, idiopathic bile acid malabsorption or reduce plasma cholesterol with the combination therapy and pharmaceutical compositions of the present invention can be selected using a variety of factors. These include the type, age, weight, sex, diet, and medical condition of the patient, the severity of the disease, the route of administration, pharmacological consideration such as the activity, efficacy, pharmacokinetics and toxicology profiles of the particular compound employed, whether a drug delivery system is utilized, and whether the amine polymer is administered as part of a drug combination. Thus, the dosage regimen actually employed may vary widely.

Initial treatment of a patient suffering from a hyperlipidemic condition such as hypercholesterolemia and/or atherosclerosis can begin with the dosages indicated above. Treatment should generally be continued as necessary over a period of several weeks to several months or years until the condition has been controlled or eliminated. Patients undergoing treatment with the amine polymers disclosed herein can be routinely monitored by, for example, measuring serum LDL and total cholesterol levels by any of the methods well known in the art, to determine the effectiveness of the combination therapy. Repeated analysis of such data permits modification of the treatment regimen during therapy so that optimal effective amounts of each type of agent are administered at any point in time, and so that the duration of treatment can be determined as well. In this way, the treatment regimen/dosing schedule can be rationally modified over the course of therapy so that the lowest amount of amine polymer and optionally, combination treatment, is administered and so that administration is continued only so long as is necessary to successfully treat the hyperlipidemic condition such as hypercholesterolemia and atherosclerosis.

If necessary, the amine polymers or pharmaceutical compositions may be administered in combination with other therapeutic agents. The choice of therapeutic agents that can be co-administered with the compounds of the invention will depend, in part, on the condition being treated. For example, various agents can be co-administered with the amine polymer, including agents used in reducing serum LDL-cholesterol or non-HDL-cholesterol, which comprise a hydroxymethyl-glutaryl-coenzyme A (HMG CoA) reductase inhibitor, a fibrate, a cholesterol absorption inhibitor, niacin (i.e. nicotinic acid or derivatives thereof), a phytosterol, an intestinal lipase inhibitor, an intestinal or secreted phospholipase A2 inhibitor, inhibitors of the synthesis or normal activity of Apo-B100, agonists of the synthesis or normal activity of ApoA, or any agent that modulates cholesterol absorption or metabolism, or a combination thereof. In some instances, the HMG CoA reductase inhibitor comprises a statin, such as atorvastatin, cerivastatin, fluvastatin, lovastatin, mevastatin, pitavastatin, pravastatin, rosuvastatin, simvastatin, or a combination thereof. The cholesterol absorption inhibitor can comprise ezetimibe. The fibrate can be benzafibrate, ciprofibrate, clofibrate, gemfibrozil, fenofibrate, or a combination thereof. The intestinal lipase inhibitor can comprise orlisatat. In some instances, the amine polymers or pharmaceutical compositions may be administered in combination with a HMG CoA reductase inhibitor and niacin (e.g., lovastatin and niacin), or a HMG CoA reductase inhibitor and a cholesterol absorption inhibitor (e.g., simvastatin and ezetimibe), or a HMG CoA reductase inhibitor and an intestinal lipase inhibitor.

In another example, other agents can be co-administered with the amine polymer, including agents used in preventing or treating diabetes, obesity or other dyslipidemias, such as a sulfonylurea, a biguanidine, a glitazone, a thiazolidindione, an activator of peroxisome poliferator-activated receptors (PPARs), an alpha-glucosidase inhibitor, a potassium channel antagonist, an aldose reductase inhibitor, a glucagon antagonist, a retinoid X receptor (RXR) antagonist, a farnesoid X receptor (FXR) agonist, a FXR antagonist, glucagon-like peptide-1 (GLP-1), a GLP-1 analog, a dipeptidyl peptidase IV (DPP-IV) inhibitor, amylin, an amylin analog, an SGLT2 inhibitor, insulin, an insulin secretagogue, a thyroid hormone, a thyroid hormone analog, an alpha glucosidase inhibitor or a combination thereof. The biguanidine can be metformin, buformin, phenformin, or a combination thereof. The thiazolidindione can be pioglitazone, rivoglitazone, rosiglitazone, troglitazone, or a combination thereof. The sulfonylurea can be acetohexamide, chlorpropamide, tolbutamide, tolazamide, glipizide, gliclazide, glibenclamide, gliquidone, glyclopyramide, glimepiride, or a combination thereof. The DPP-IV inhibitor can be alogliptin, linagliptin, saxagliptin, sitagliptin, vildagliptin, or a combination thereof. The GLP-1 analog can be exenatide, liraglutide, albiglutide, or a combination thereof. The alpha glucosidase inhibitor can be acarbose, miglitol or voglibose.

The term dyslipidemia is taken to mean a deviation in at least one of total serum cholesterol, LDL-cholesterol, non-HDL cholesterol, HDL-cholesterol or triglyceride from that considered normal by the National Cholesterol Education Program or other suitable bodies. In another example, other agents can be co-administered with the amine polymer, including an anti-platelet agent, a beta-blocker, a renin-angiotensin-aldosterone system (RAAS) inhibitor, a RAAS modulator (e.g., angiotensin converting enzyme inhibitors, renin inhibitors, angiotensin receptor blockers, aldosterone antagonists or sodium channel blockers, including amiloride, triamterene, trimethoprim, and pentamidine) or a combination thereof.

The amine polymers can also be administered with other cholesterol-lowering agents such as acifran, azacosterol, benfluorex, β-benzalbutyramide, carnitine, chondroitin sulfate, clomestrone, detaxtran, dextran sulfate sodium, 5,8,11, 14,17-eicosapentaenoic acid, eritadenine, furazabol, meglutol, melinamide, mytatrienediol, ornithine, γ-oryzanol, pantethine, pentaerythritol tetraacetate, α-phenybutyramide, priozadil, probucol, β-sitosterol, sultosilic acid, piperazine salt, tiadenol, triparanol, xenbucin, or a combination thereof.

Other agents that can be advantageously used for treatment in combination with the amine polymers are a squalene epoxidase inhibitor, a squalene synthetase inhibitor (or squalene synthase inhibitor), an acyl-coenzyme A, cholesterol acyltransferase (ACAT) inhibitor (including selective inhibitors of ACAT-1 or ACAT-2, as well as dual inhibitors of ACAT-1 and ACAT-2), a microsomal triglyceride transfer protein (MTP) inhibitor, probucol, a cholesterol absorption inhibitor (e.g., ezetimibe and 1-(4-fluorophenyl)-3(R)-3(S)-(4-fluorophenyl)-3-hydroxypropyl), 4(S)-4-hydroxyphenol (-2-azetidinone) described in U.S. Pat. Nos. 5,727,115 and 5,846,966), a LDL receptor inducer, a platelet aggregation inhibitor (e.g., a glycoprotein IIb/IIa fibrinogen receptor antagonist), aspirin, vitamin $B_6$ (or pyridoxine), vitamin $B_{12}$ (or cyanocobalamin), a water-soluble pharmaceutical salt or ester of folic acid (e.g., sodium salt and the methylglucamine salt), an anti-oxidant vitamin (e.g., vitamin C and E and beta-carotene), or a combination thereof.

The term "treating" as used herein includes achieving a therapeutic benefit. By therapeutic benefit is meant eradication, amelioration, or prevention of the underlying disorder being treated. For example, in a hypercholesterolemia patient, therapeutic benefit includes eradication or amelioration of the underlying hypercholesterolemia. Also, a therapeutic benefit is achieved with the eradication, amelioration, or prevention of one or more of the physiological symptoms associated with the underlying disorder such that an improvement is observed in the patient, notwithstanding that the patient may still be afflicted with the underlying disorder. In some treatment regimens, the amine polymer or composition of the invention may be administered to a patient at risk of developing hypercholesterolemia or diabetes or to a patient reporting one or more of the physiological symptoms of hypercholesterolemia or diabetes, even though a diagnosis of hypercholesterolemia or diabetes may not have been made.

The pharmaceutical compositions of the present invention include compositions wherein the amine polymers are present in an effective amount, i.e., in an amount effective to achieve therapeutic or prophylactic benefit. The actual amount effective for a particular application will depend on the patient (e.g., age, weight, etc.), the condition being treated, and the route of administration. Determination of an effective amount is well within the capabilities of those skilled in the art, especially in light of the disclosure herein. The effective amount for use in humans can be estimated from animal models. For example, a dose for humans can be formulated to achieve gastrointestinal concentrations that have been found to be effective in animals. In various embodiments, the human patient takes about 0.5 g to about 10 g per day, preferably about 0.5 g to about 5 g per day, more preferably, about 0.5 g to about 3 g per day, about 0.5 g to about 2.5 g per day, and most preferably about 0.5 g to about 2.0 g per day.

The polymers and compositions described herein can be used as food products and/or food additives. They can be added to foods prior to consumption or during packaging.

The amine polymers or pharmaceutically acceptable salts thereof, or compositions described herein, can be delivered to the patient using a wide variety of routes or modes of administration. The most preferred routes for administration are oral, intestinal, or rectal. Rectal routes of administration are known to those of skill in the art. Intestinal routes of administration generally refer to administration directly into a segment of the gastrointestinal tract, e.g., through a gastrointestinal tube or through a stoma. The most preferred route for administration is oral.

The polymers (or pharmaceutically acceptable salts thereof) may be administered per se or in the form of a pharmaceutical composition wherein the active compound(s) is in admixture or mixture with one or more pharmaceutically acceptable excipients. Pharmaceutical compositions for use in accordance with the present invention may be formulated in a conventional manner using one or more pharmaceutically acceptable excipients comprising carriers, diluents, and auxiliaries which facilitate processing of the active compounds into preparations which can be used physiologically. Proper composition is dependent upon the route of administration chosen.

For oral administration, the polymers or compositions of the invention can be formulated readily by combining the polymer or composition with pharmaceutically acceptable excipients well known in the art. Such excipients enable the compositions of the invention to be formulated as powders, tablets, pills, dragees, capsules, liquids, gels, syrups, slurries, suspensions, wafers, and the like, for oral ingestion by a patient to be treated. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose or sucrose; cellulose preparations such as, for example, maize starch, wheat starch, rice starch, potato starch, gelatin, gum tragacanth, methyl cellulose, hydroxypropyl methylcellulose, sodium carboxymethylcellulose, and/or polyvinyl pyrrolidone (PVP); and various flavoring agents known in the art. If desired, disintegrating agents may be added, such as the cross-linked polyvinyl pyrrolidone, agar, or alginic acid or a salt thereof such as sodium alginate.

Additionally, the amine polymer composition can comprise one or more fat-soluble vitamins such as vitamin A, D, E, K, or a combination thereof. An amount of the fat-soluble vitamin can be added to the composition sufficient to deliver about the daily dietary intake level (i.e., the Reference Daily Intake (RDI)), which is currently 3000 IU, 400 IU, 30 IU, 80 gig, respectively, for vitamin A, D, E, and K.

In various embodiments, the active ingredient (e.g., polymer) constitutes over about 20%, more particularly over about 50%, even more particularly over about 75%, and most particularly more than about 90% by weight of the oral dosage form, the remainder comprising suitable excipient(s).

The amine polymers or pharmaceutical compositions can be administered in the form of a chewable or mouth-disintegrating tablet, a liquid, a powder, a powder contained within a sachet, a soft gelatin capsule, or a hard gelatin capsule. In some embodiments, the polymers of the invention are provided as pharmaceutical compositions in the form of liquid compositions. In various embodiments, the pharmaceutical composition contains an amine polymer dispersed in a suitable liquid excipient. Suitable liquid excipients are known in the art; see, e.g., Remington's Pharmaceutical Sciences.

An effective amount of the polymers of the invention can be administered to the animal subject in less than four unit doses per day, such as in less than four tablets per day. The "dosage unit" or "unit dose" is a tablet, capsule or other oral dosage form containing an amount of the amine polymer. The polymer is generally administered in 4, 3, 2 or 1 unit doses in a 24-hour period, which provides a daily dose of the polymer to the subject under treatment.

Unless otherwise indicated, an "alkyl" group as described herein alone or as part of another group is an optionally substituted linear saturated monovalent hydrocarbon radical containing from one to twenty carbon atoms and preferably one to twelve carbon atoms, or an optionally substituted branched saturated monovalent hydrocarbon radical containing three to twenty carbon atoms, and preferably three to eight carbon atoms. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term "amide" as used herein represents a bivalent (i.e., difunctional) amido linkage (i.e.,

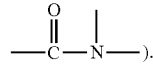

).

The term "aryl" as used herein alone or as part of another group denotes an optionally substituted monovalent aromatic hydrocarbon radical, preferably a monovalent monocyclic or bicyclic group containing from 6 to 12 carbons in the ring portion, such as phenyl, biphenyl, naphthyl, substituted phenyl, substituted biphenyl or substituted naphthyl. Phenyl and substituted phenyl are the more preferred aryl groups. The term "aryl" also includes heteroaryl.

The term "cycloalkyl" as used herein denotes optionally an optionally substituted cyclic saturated monovalent bridged or non-bridged hydrocarbon radical containing from three to eight carbon atoms in one ring and up to 20 carbon atoms in a multiple ring group. Exemplary unsubstituted cycloalkyl groups include cyclopropyl, cyclobutyl, cyclopentyl, cyclohexyl, cycloheptyl, cyclooctyl, adamantyl, norbornyl, and the like.

The term "-ene" as used as a suffix as part of another group denotes a bivalent radical in which a hydrogen atom is removed from each of two terminal carbons of the group, or if the group is cyclic, from each of two different carbon atoms in the ring. For example, alkylene denotes a bivalent alkyl group such as methylene (—CH$_2$—) or ethylene (—CH$_2$CH$_2$—), and arylene denotes a bivalent aryl group such as o-phenylene, m-phenylene, or p-phenylene. For clarity, addition of the -ene suffix is not intended to alter the definition of the principal word other than denoting a bivalent radical. Thus, continuing the example above, alkylene denotes an optionally substituted linear saturated bivalent hydrocarbon radical.

The term "ether" as used herein represents a bivalent (i.e., difunctional) ether linkage (i.e., —O—).

The term "ester" as used herein represents a bivalent (i.e., difunctional) ester linkage (i.e., —C(O)O—).

The term "heteroaryl," as used herein alone or as part of another group, denotes an optionally substituted monovalent monocyclic or bicyclic aromatic radical of 5 to 10 ring atoms in protonated or unprotonated form, where one or more, preferably one, two, or three, ring atoms are heteroatoms independently selected from N, O, and S, and the remaining ring atoms are carbon. Exemplary heteroaryl moieties include benzofuranyl, benzo[d]thiazolyl, benzo[d]thiazolium, isoquinolinyl, isoquinolinium, quinolinyl, quinolinium, thiophenyl, imidazolyl, imidazolium, oxazolyl, oxazolium, furanyl, thiazolyl, thiazolium, pyridinyl, pyridinium, furyl, thienyl, pyridyl, pyrrolyl, pyrrolidinium, indolyl, indolinium, and the like.

The term "heterocyclo," as used herein alone or as part of another group, denotes a saturated or unsaturated monovalent monocyclic group of 4 to 8 ring atoms in protonated or unprotonated form, in which one or two ring atoms are heteroatom(s), independently selected from N, O, and S, and the remaining ring atoms are carbon atoms. Additionally, the heterocyclic ring may be fused to a phenyl or heteroaryl ring, provided that the entire heterocyclic ring is not completely aromatic. Exemplary heterocyclo groups include the heteroaryl groups described above, pyrrolidino, pyrrolidinium, piperidino, piperidinium, morpholino, morpholinium, piperazino, piperazinium, and the like.

The term "hydrocarbon" as used herein describes a compound or radical consisting exclusively of the elements carbon and hydrogen.

The term "substituted" as in "substituted aryl," "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON($R_A$)($R_B$), wherein $R_A$ and $R_B$ are independently hydrogen, alkyl, or aryl), amino(—N($R_A$)($R_B$), wherein $R_A$ and $R_B$ are independently hydrogen, alkyl, or aryl), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

As used herein "possible reaction sites" in the amine monomers are nitrogen atoms bonded to one or more hydrogen atoms.

Having described the invention in detail, it will be apparent that modifications and variations are possible without departing from the scope of the invention defined in the appended claims.

EXAMPLES

The following non-limiting examples are provided to further illustrate the present invention. The following assays were used for the in vitro and in vivo testing detailed in the examples below.

Protocol 1: Conditions Mimicking the Lower Small Intestine (a Assay).

Amine polymers were measured in conditions mimicking those found in the lower small intestine (Northfield, T C and McColl, I (1973) "Postprandial concentrations of free and conjugated bile salts down the length of the normal human small intestine", Gut 14: 513-518, Borgstrom, B, et al. (1957) "Studies of intestinal digestion and absorption in the human", J Clin Invest 36: 1521-1536.)

The following test solution was prepared: 50 mM N,N-Bis(2-hydroxyethyl)-2-aminoethanesulfonic acid (BES), 50 mM sodium BES, 6.5 mM sodium phosphate, 0.93 mM sodium glycocholate, 0.93 mM sodium glycodeoxycholate, 150 mM sodium chloride, pH 7.0. The test solution was stored at −20° C. Before use the test solution was thawed in a 37° C. water bath, stirred vigorously on a stir plate for greater than 20 minutes, and filtered through a Nalgene 0.45 micron cellulose nitrate filter unit. This was found to provide reproducible results Amine polymers to be analyzed were freeze-dried a minimum of 18 hours and were accurately dispensed into 16×100 mm borosilicate test tubes, with each tube containing between 23 and 28 mg of test sample. The precise weight was noted and the above solution was added using a 10 mL disposable pipette, so that the polymer concentration was 2.5 mg/mL. The tubes were covered with a sheet of Teflon, clamped and tumbled end-over-end (30-40 revolutions per minute) inside an atmospheric chamber at 37° C. for three hours. The polymers were recovered by centrifugation at 500×g for 10 minutes and the supernatants were sampled, filtered through a 96 well 0.45 micron Whatman Unifilter 800 by centrifugation at 1000×g for 10 minutes to remove any remaining particulates. Filtrates were transferred to either glass IC vials with rubber septa or 96 well polypropylene deep well sample plates.

To determine the concentration of glycocholate (GC) and glycodeoxycholate (GDC) in the filtrate, 50 μL of the sample solution was injected onto a HPLC system, equipped with Phenomenex Luna C8 (2) column (100 Å, 5 μm, 50×2.00 mm), and a UV detector. The sample was analyzed using a gradient of water, 25 mM phosphate buffer (pH=3) and acetonitrile at a flow rate of 0.4 mL/min. The signal of GC and GDC was detected at a wavelength of 205 nm from the UV detector. Calibration solutions comprised of GC and GDC standards of different concentrations were also injected onto the same HPLC system. The calibration curve of each component was then constructed by plotting the peak area vs. concentration. Based on the peak area of the GC and GDC found in the sample and the corresponding calibration curve, the concentration of each component in the sample was calculated in mM.

By comparing the equilibrium concentrations of glycocholate ($GC_{eq}$) and glycodeoxycholate ($GDC_{eq}$), in the presence of the polymer to their concentrations in test solution in the absence of the polymer, the amount of each component bound under these experimental conditions in mmoles/g polymer was calculated.

In some cases, the concentration of phosphate was also determined by injection of 20 uL of filtrate onto strong anion exchange columns (Dionex AG11-HC 50×4 mm ID and Dionex AS11-HC 250×4 mm ID) using a Waters Alliance 2795 Separation Module equipped with a 6 column switching valve installed inside a column oven and a Dionex Conductivity Detector CD25 (with DS3 flow cell and ASRS Ultra 11.4 mm Suppressor). The mobile phase was 30 mM KOH buffer with a 1 mL/min flow rate and a run time of 15 minutes per sample. Phosphate standards of different concentrations were also injected onto the same system and the calibration curve was then constructed by plotting the peak area vs. concentration. Based on the peak area found in the sample and the corresponding calibration curve, the concentration of phosphate in the sample was calculated in mM.

By comparing the equilibrium concentrations of phosphate ($P_{eq}$) and in the presence of the polymer to their concentrations in test solution in the absence of the polymer, the amount of phosphate bound under these experimental conditions in mmoles/g polymer was calculated.

Protocol 2: Conditions Mimicking the Upper Small Intestine (Assay B).

Amine polymers were also measured in conditions mimicking those found in the upper small intestine after a meal (Fordtran, J S and Locklear, T W (1966) "Ionic constituents and osmolality of gastric and small-intestinal fluids after eating", Am J Dig Dis 11: 503-521; Northfield, T C and McColl, I (1973) "Postprandial concentrations of free and conjugated bile salts down the length of the normal human small intestine", Gut 14: 513-518; Evans, D F, et al. (1988) "Measurement of gastrointestinal pH profiles in normal ambulant human subjects", Gut 29: 1035-1041). The bile salt binding performance of test polymers was evaluated at a polymer concentration of 2.5 mg/mL in the manner described in Protocol 1 above, with the exception that the following test solution was used: 50 mM N,N-Bis(2-hydroxyethyl)-2-aminoethanesulfonic acid (BES), 50 mM sodium BES, 6.5 mM sodium phosphate, 4.6 mM sodium glycocholate, 4.6 mM sodium glycodeoxycholate, 1.2 mM oleyl glycerol, 9 mM oleic acid, 150 mM sodium chloride, pH 7.0. Freeze-dried polymer was precisely dispensed into the 16×100 mm borosilicate test tubes, with each tube containing between 28 and 33 mg of test sample. In certain cases, the concentration of polymer was adjusted from 2.5 mg/mL to 1 mg/mL. Otherwise the procedure was identical to that described in Protocol 1 above, except filtrates submitted for analytical analysis were only dispensed into glass IC vials.

To determine the concentration of glycocholate (GC), glycodeoxycholate (GDC), oleyl glycerol (OG) and oleic acid (OA) concentrations in filtrate samples, 20 µL was injected onto a HPLC system that was equipped with a Phenomenex Luna C8 (2) column (100 Å, 5 µm, 50×2.00 mm,) and a UV detector. The sample was analyzed using a gradient of water, 25 mM phosphate buffer (pH=3) and acetonitrile at a flow rate of 0.4 mL/min. The signal of GC, GDC, OG and OA is detected at a wavelength of 205 nm from the UV detector. Calibration solutions comprised of GC, GDC, OG and OA standards of different concentrations were also injected onto the same HPLC system. The calibration curve of each component was then constructed by plotting the peak area vs. concentration. Based on the peak area of the GC, GDC, OG or OA found in the sample and the corresponding calibration curve, the concentration of each component in the sample is calculated in mM.

By comparing the equilibrium concentrations of glycocholate (GCeq), glycodeoxycholate (GDCeq), oleyl glycerol (OGeq) and/or oleic acid (OAeq) in the presence of the polymer to their concentrations in test solution in the absence of the polymer, the amount of each component bound under these experimental conditions in mmoles/g polymer was calculated.

Hamster Model. To collect in vivo data, Male Golden Syrian hamsters (8-9 weeks old) were obtained from Charles River Laboratories (Wilmington, Mass.). Upon arrival, the animals were placed on rodent diet Teklad 2018 (Madison, Wis.). Food and water were provided ad libitum throughout the course of the study Animals were acclimated for at least seven days, and then randomized by body weight into groups of at least five animals each. All animals were then placed on a high-fat, high-sucrose western diet, D12079B (Research Diet, New Brunswick, N.J.) for three days before the study started Amine polymers were blended into western diet at a dose of 0.5% to prepare the test diets. To initiate the study, all hamsters were moved into individual metabolic cages allowing the separation and collection of feces. Animals from the test groups were switched to the test diets, while animals from the untreated group were kept on western diet without added amine polymer. Food intake was measured for the next four consecutive days. For each hamster, feces from the last three days of the treatment period were collected, pooled, lyophilized, and then homogenized by grinding in a mortar and pestle. The feces samples were then extracted for fecal bile salt analysis.

In some cases, a baseline treatment period was conducted where all groups of animals were placed in metabolic cages as described above and fed only on western diet without added test article. Feces were collected as described above and the effect of amine polymer on bile salt fecal excretion was determined by comparing baseline versus treatment periods. Otherwise, the effect of amine polymer on bile salt fecal excretion was determined by comparing untreated versus test groups.

Hamster fecal bile salts were analyzed using a modification of the procedure reported by Porter and colleagues (Porter, J L. et al. 2003. Accurate enzymatic measurement of fecal bile salts in patients with malabsorption. J Lab Clin Med. 141:411-8). For each extraction, a 100 mg aliquot of dry feces was weighed into a 16×100 mm Pyrex test tube. Ethylene glycol (1 mL) with 0.7N NaOH was then added. The test tube was capped with a marble and heated at 190-200° C. for 2 h. After cooling, 1 mL of 20% NaCl and 0.2 mL 6N HCl were added. After brief mixing, 6 ml diethyl ether was added. The tube was capped, vortexed for 5 minutes, and then centrifuged at 1,000×g for 5 minutes. The diethyl ether phase was transferred into a 20 mL glass vial. Two additional extractions with 6 mL diethyl ether were performed and the extracts were pooled. The ether was completely evaporated under a stream of air. The residue was then dissolved in 3 mL methanol and bile salts (cholic acid, 3-OH-12-oxo-cholanic acid, chenodeoxycholic acid, deoxycholic acid, and lithocholic acid) were quantified by LC-MS.

Example 1

N,N,N',N'-tetrakis(3-aminopropyl)-1,4-butanediamine ($C_4$ BTA) polymers with dihaloalkane cross-linkers Synthesis of crosslinked N,N,N',N'-tetrakis(3-aminopropyl)-1,4-butanediamine materials were conducted using parallel synthesis. A solution of N,N,N',N'-tetrakis(3-aminopropyl)-1,4-butanediamine ($C_4$ BTA) (40 wt. % of a N,N-dimethylformamide (DMF) solution) was dispensed into 40 mL glass vials. The crosslinking monomer of formula X—$R_1$—X, wherein X was bromo and $R_1$ was as listed in the table below, were added to each vial. Additional DMF and methanol (MeOH) were added resulting in a total solid content of 40 wt. % where the solvents are in at a ratio of 1:1 (by volume). The vials were capped and heated for 17 hours at 58° C. The resulting polymer gel was swollen and ground in MeOH, washed in MeOH (twice), ammonium hydroxide (10 vol. %, twice) then water (three times) and lyophilized until dry. Bile acid (BA) binding capacity, affinity, and retention for each resulting polymer were determined via the A assay, B assay and hamster model as described above, and results are reported below.

Synthesis of N,N,N',N'-tetrakis(3-aminopropyl)-1,4-butanediamine To a mixture of 1,4-diamino butane and acrylonitrile in dioxane was added 40% KOH solution under nitrogen. The reaction was stirred at room temperature over night and HPLC was used to monitor the reaction. After the completion of reaction, the mixture was diluted with tert-butyl methyl ether. The organic phase was washed with brine, then dried over anhydrous sodium sulfate. After concentration of the solution, 3,3',3'',3'''-(butane-1,4-diylbis(azanetriyl))tetrapropanenitrile was obtained. A suspension of 3,3',3'',3'''-(butane-1,4-diylbis(azanetriyl))tetrapropanenitrile in 1:1 methanol:water was placed in a Parr hydrogenation apparatus. To the mixture was charged wet Raney cobalt catalyst. The mixture was hydrogenated under 700 psi at 70° C. for 18 hours. After cooling to room temperature, the reaction was filtered through celite. The filtrate was concentrated to yield N,N,N',N'-tetrakis(3-aminopropyl)-1,4-butanediamine ($C_4$ BTA) as a pale yellow oil.

N,N,N',N'-tetrakis(3-aminopropyl)-1,8-octanediamine ($C_8$ BTA), N,N,N',N'-tetrakis(3-aminopropyl)-1,10-decanediamine ($C_{10}$ BTA), and N,N,N',N'-tetrakis(3-aminopropyl)-1,12-dodecanediamine ($C_{12}$ BTA) were synthesized following same procedure.

| Sample # | Bisacrylamide Crosslinking Monomer | Monomer: Crosslinking Monomer Molar Ratio | Crosslinking Monomer (mg) | $C_4$ BTA (uL) | DMSO (uL) |
|---|---|---|---|---|---|
| 2-C3 | N, N'-Octylene bis(acrylamide) | 1:2.2 | 1911 | 1135 | 5450 |
| 2-D2 | N, N'-Decylene bis(acrylamide) | 1:1.6 | 1759 | 1293 | 5450 |

| Sample # | BA binding affinity A assay (mmol/g) | BA binding capacity B assay (mmol/g) | BA binding retention Hamster (mmol/g) | BA Binding % Primary Bile Acids in feces* | Swelling (gm/gm) |
|---|---|---|---|---|---|
| 2-C3 | 0.60 | 2.97 | 0.39 | 21.5 | 2.00 |
| 2-D2 | 0.69 | 3.00 | 0.44 | 49.7 | 1.52 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

| Sample # | Crosslinking monomer ($R_1$) | Monomer: Crosslinking Monomer Molar Ratio | Crosslinking Monomer (mg) | $C_4$ BTA (uL) | MeOH (uL) | DMF (uL) | BA Binding affinity A assay (mmol/g) | BA binding capacity B assay (mmol/g) | BA Binding retention Hamster (mmol/g) | BA binding % Primary Bile Acids in feces* | Swelling (g/g) |
|---|---|---|---|---|---|---|---|---|---|---|---|
| 1-A1 | $C_8$ alkylene | 1:1.6 | 6705 | 5080 | 11126 | 11126 | 0.44 | 3.34 | 0.41 | 5.9 | 1.42 |
| 1-A2 | $C_8$ alkylene | 1:2.2 | 6358 | 3503 | 9338 | 9338 | 0.50 | 3.29 | | | 0.79 |
| 1-A3 | $C_{10}$ alkylene | 1:1.6 | 6868 | 4717 | 10947 | 10947 | 0.58 | 3.24 | 0.66 | 13.9 | 0.67 |
| 1-A4 | $C_{10}$ alkylene | 1:2.2 | 6537 | 3265 | 9291 | 9291 | 0.65 | 2.95 | 0.52 | 25.0 | 0.60 |
| 1-A5 | $C_{10}$ alkylene | 1:2.8 | 6083 | 2387 | 8045 | 8045 | 0.64 | 1.86 | | | 1.13 |
| 1-A6 | $C_{12}$ alkylene | 1:1.6 | 7011 | 4403 | 10795 | 10795 | 0.68 | 3.25 | 0.77, 0.81 | 23.4, 20.0 | 0.41 |
| 1-B1 | $C_{12}$ alkylene | 1:2.2 | 6694 | 3057 | 9250 | 9250 | 0.68 | 2.66 | 0.47 | 22.1 | 0.50 |

†average of 2 studies
*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 2

N,N,N',N'-tetrakis(3-aminopropyl)-1,4-butanediamine ($C_4$ BTA) polymers with bisacrylamide crosslinkers Synthesis of crosslinked N,N,N',N'-tetrakis(3-aminopropyl)-1,4-butanediamine materials were conducted using parallel synthesis. A solution of N,N,N',N'-tetrakis(3-aminopropyl)-1,4-butanediamine (40 wt. % of a dimethyl sulfoxide (DMSO) solution) was dispensed into 40 mL glass vials. The bisacrylamide crosslinking monomer listed in the table below was added to each vial. Additional DMSO was added resulting in a total solid content of 40 wt. %. The vials were capped and heated for 17 hours at 58° C. The resulting polymer gel was swollen and ground in MeOH, washed in MeOH (twice), NaOH (0.5M once) then water (three times) and lyophilized until dry. Bile acid (BA) binding capacity, affinity, and retention for each resulting polymer were determined via the A assay, B assay and hamster model as described above, and results are reported in the table below.

Example 3

N,N,N',N'-tetrakis(3-aminopropyl)-1,4-butanediamine ($C_4$ BTA) polymers with epichlorohydrin (ECH)—Comparative example Synthesis of crosslinked N,N,N',N'-tetrakis(3-aminopropyl)-1,4-butanediamine materials were conducted using parallel synthesis. A solution of N,N,N',N'-tetrakis(3-aminopropyl)-1,4-butanediamine (40 wt. % of a N,N-dimethylformamide (DMF) solution) was dispensed into 40 mL glass vials. Epichlorohydrin (ECH) was added to each vial. Additional DMF and methanol were added resulting in a total solid content of 40 wt. % where the solvents are in at a ratio of 1:1 (by volume). The vials were capped and heated for 17 hours at 58° C. The resulting polymer gel was swollen and ground in MeOH, washed in MeOH (twice), NaOH (0.5M once) then water (three times) and lyophilized until dry. Bile acid binding capacity, affinity, and retention for each resulting polymer were determined via the A assay, B assay and hamster model as described above, and results are reported in the table below.

| Sample | Crosslinking Monomer | Monomer: Crosslinking Monomer Molar Ratio | Crosslinking Monomer (mg) | C4 BTA (uL) | Methanol (uL) | DMF (uL) | Bile acid binding affinity A assay (mmol/g) | Bile acid binding capacity B assay (mmol/g) | Bile acid binding retention Hamster (mmol/g) | BA binding % Primary Bile Acids in feces* | Swelling g/g |
|---|---|---|---|---|---|---|---|---|---|---|---|
| 3-A1 | ECH | 1:1.6 | 39829 | 88720 | 72046 | 72046 | 0.34 | 3.15 | 0.12 | 4.7 | 52.06 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 4

N,N,N',N'-tetrakis(3-aminopropyl)-1,12-dodecanediamine ($C_{12}$ BTA) polymers with 1,3-bis(3-iodopropyl)-1H-imidazol-3-ium Synthesis of crosslinked N,N,N',N'-tetrakis(3-aminopropyl)-1,4-butanediamine materials were conducted using parallel synthesis. N,N,N',N'-tetrakis(3-aminopropyl)-1,12-dodecanediamine was dispensed into a 40 mL glass vial. 1,3-bis(3-iodopropyl)-1H-imidazol-3-ium and N-methylpyrrolidone (NMP) was added to the vial. The vial was capped and heated for 17 hours at 58° C. The resulting polymer gel was swollen and ground in MeOH, washed in MeOH (twice), hydrochloric acid (1M, three times) then water (three times) and lyophilized until dry. Bile acid binding capacity, affinity, and retention for each resulting polymer were determined via the A assay, B assay and hamster model as described above, and results are reported in the table below.

| Sample # | Monomer: Crosslinking Monomer Molar Ratio | $C_{12}$ BTA (mg) | 1,3-bis(3-iodopropyl)-1H-imidazol-3-ium Crosslinking monomer (mg) | NMP (uL) |
|---|---|---|---|---|
| 4-B3 | 1:1.26 | 2080 | 3253 | 5666 |

| Sample # | Bile acid binding affinity A assay (mmol/g) | Bile acid binding capacity B assay (mmol/g) | Bile acid binding retention Hamster (mmol/g) | BA binding % Primary Bile Acids in feces* | Swelling (g/g) |
|---|---|---|---|---|---|
| 4-B3 | 0.51 | 2.99 | 0.48 | 18.5 | 11.45 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 5

Preparation of 1,3-bis(3-iodopropyl)-1H-imidazol-3-ium

A slurry of imidazole sodium salt (18.3 g, 0.2 mol) and 1-bromo-3-chloropropane (50 mL, 0.5 mol) in 200 mL of THF was stirred at room temperature overnight. The mixture was then refluxed for 8 hours and concentrated to dryness. Acetone (250 mL) was added to the residue, followed by sodium iodide (150 g, 1 mol). The slurry was stirred under refluxing overnight. Solvent was removed under reduced pressure. To the residue was added 300 mL of 10% methanol in dichloromethane. Solid was removed by filtration. The filtrate was concentrated and purified by chromatography (silica gel, 10-15% methanol in dichloromethane). 11.5 g of desired product was obtained as a brown oil. MS m/e (MH+), calcd 404.93. found 404.73. $^1$H NMR confirmed the structure.

| Crosslinking monomer | Structure |
|---|---|
| $C_{10}$ bis-imidazolium | 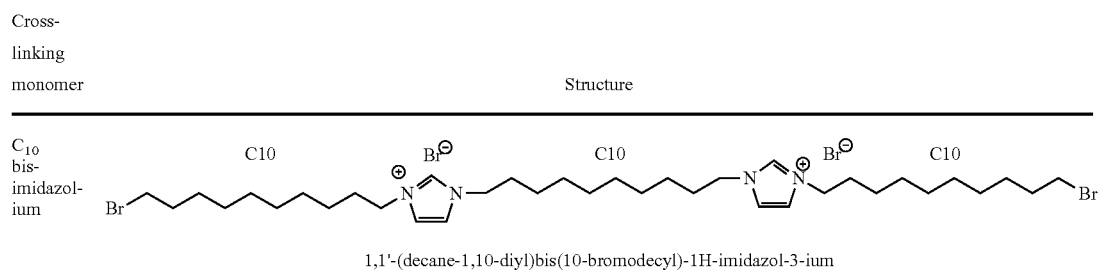<br>1,1'-(decane-1,10-diyl)bis(10-bromodecyl)-1H-imidazol-3-ium |
| $C_{12}$ bis-imidazolium | 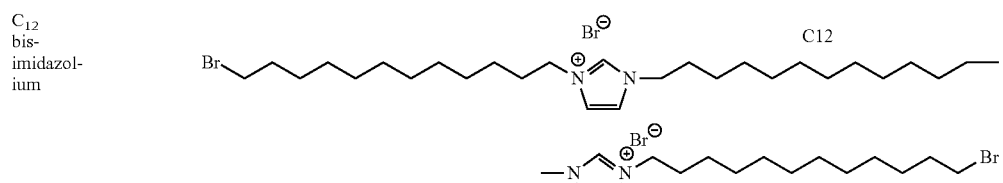<br>1,1'-(dodecane-1,12-diyl)bis(12-bromododecyl)-1H-imidazol-3-ium |

-continued

| Cross-linking monomer | Structure |
|---|---|
| $C_{12}$ core, $C_3$ bis-imidazolium | 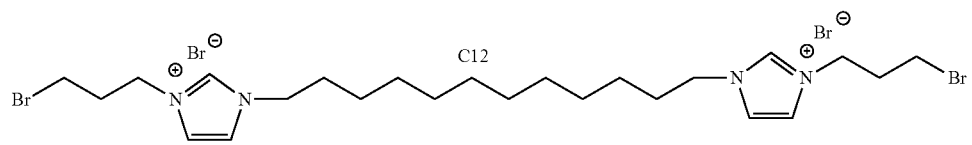<br>1,1'-(dodecane-1,12-diyl)bis(3-bromopropyl)-1H-imidazol-3-ium |
| $C_3$ bis-imidazolium | 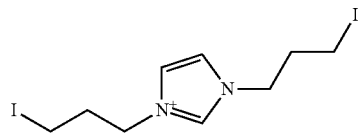 [SMILES: ICCCn1cc[n+](CCCI)c1]<br>1,3-bis(3-iodopropyl)-1H-imidazol-3-ium |

| Amine Monomer | Structure |
|---|---|
| $C_4$ BTA | 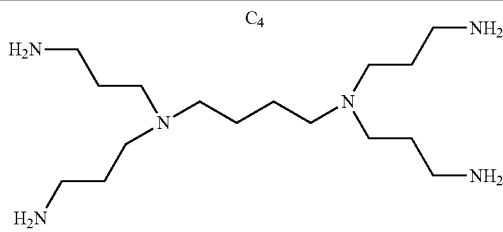 [SMILES: "C4" ; NCCCN(CCCN)CCCCN(CCCN)CCCN]<br>N,N,N',N'-tetrakis(3-aminopropyl)-1,4-butanediamine |
| $C_8$ BTA | 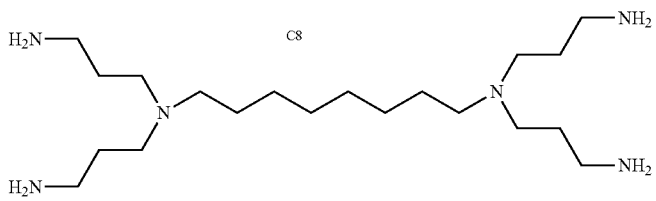<br>N,N,N',N'-tetrakis(3-aminopropyl)-1,8-octanediamine |
| $C_{10}$ BTA | 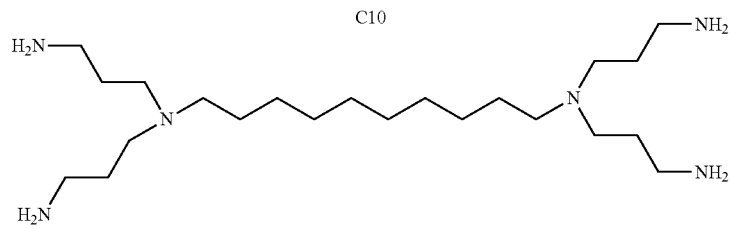 [SMILES: "C10" ; NCCCN(CCCN)CCCCCCCCCCN(CCCN)CCCN]<br>N,N,N',N'-tetrakis(3-aminopropyl)-1,10-decanediamine |
| $C_{12}$ BTA | 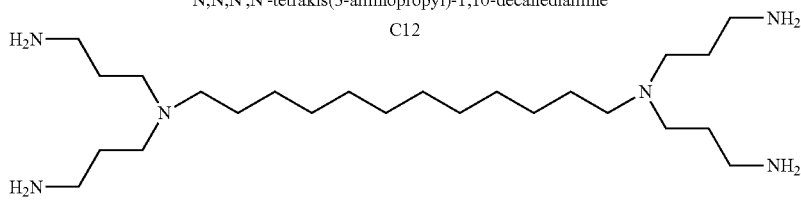<br>N,N,N',N'-tetrakis(3-aminopropyl)-1,12-dodecanediamine |

Example 6

$C_4$ BTA and $C_{10}$ BTA Monomers with Bis Imidazolium Crosslinking Monomers Synthesis of N,N,N',N'-tetrakis(3-aminopropyl)-1,4-butanediamine ($C_4$ BTA), N,N,N',N'-tetrakis(3-aminopropyl)-1,10-decanediamine ($C_{10}$ BTA) polymers materials were conducted using dispensing robots with liquid and powder dispensing capacities. $C_4$ BTA or $C_{10}$ BTA monomer was dispensed into 8 mL glass vials. Solutions of the crosslinking monomer of formula X—$R_1$—X wherein X is halo such as chloro or bromo and $R_1$ is a imidazolium hydrocarbon chain listed in the examples below. Crosslinkers were dispensed as 40 wt. % in dimethyl sulfoxide (DMSO). Solvent was added to each vial to make the final solid content concentration at 40 wt. %. Vials were equipped with magnetic stirrer, capped and heated for 17 hours at 70° C. Most vials contained a solid plug of polymer. The polymer was swollen and ground in dimethyl formamide (DMF), washed with aqueous hydrochloric acid (1 M), water, saturated solution sodium bicarbonate (NaHCO$_3$) three times, water (two times) and lyophilized until dry.

| Sample # | monomer/ crosslinker mole ratio | Monomer | weight (mg) | Crosslinking Monomer ($R_1$) | Weight (mg) | DMSO (mg) | BA binding Capacity B assay (mmol/g) | Affinity A assay (mmol/g) | Retention Hamster (mmol/g) | BA binding % Primary Bile Acids in feces* |
|---|---|---|---|---|---|---|---|---|---|---|
| 5-A1 | 1:1.6 | $C_4$ BTA | 200.0 | $C_{10}$ bisimidazolium | 879.7 | 1619.6 | | | | |
| 5-A2 | 1:2.2 | $C_4$ BTA | 200.0 | $C_{10}$ bisimidazolium | 1209.6 | 2114.4 | 2.59 | 0.59 | | |
| 6-A1 | 1:1 | $C_4$ BTA | 200.0 | $C_{10}$ bisimidazolium | 549.8 | 1124.7 | 2.68 | 0.58 | | |
| 6-A2 | 1:1.3 | $C_4$ BTA | 200.0 | $C_{10}$ bisimidazolium | 714.8 | 1372.1 | 2.57 | 0.50 | | |
| 6-A3 | 1:1.6 | $C_4$ BTA | 200.0 | $C_{10}$ bisimidazolium | 879.7 | 1619.6 | 2.82 | 0.54 | | |
| 7-A1 | 1:1.3 | $C_4$ BTA | 1049.4 | $C_{10}$ bisimidazolium | 3750.6 | 7200.0 | 2.71 | 0.57 | | |
| 7-A2 | 1:1.6 | $C_4$ BTA | 1037.3 | $C_{10}$ bisimidazolium | 4562.7 | 8400.0 | 2.91 | 0.56 | 0.48 | 12.1 |
| 8-A1 | 1:1 | $C_4$ BTA | 200.0 | $C_{12}$ bisimidazolium | 603.0 | 1084.0 | 2.82 | 0.58 | | |
| 8-A2 | 1:1.6 | $C_4$ BTA | 200.0 | $C_{12}$ bisimidazolium | 964.7 | 1572.4 | 2.69 | 0.66 | | |
| 8-B1 | 1:1 | $C_{10}$ BTA | 200.0 | $C_{12}$ bisimidazolium | 476.3 | 913.0 | 2.61 | 0.67 | | |
| 8-B2 | 1:1.6 | $C_{10}$ BTA | 200.0 | $C_{12}$ bisimidazolium | 762.1 | 1298.9 | 2.61 | 0.62 | | |
| 8-B3 | 1:1.6 | $C_{10}$ BTA | 200.0 | $C_{12}$ bisimidazolium | 762.1 | 1298.9 | 2.68 | 0.66 | | |
| 9-A1 | 1:1 | $C_4$ BTA | 1494.5 | $C_{12}$ bisimidazolium | 4505.0 | 8100.0 | 2.62 | 0.67 | | |
| 9-A2 | 1:1.6 | $C_4$ BTA | 786.9 | $C_{12}$ bisimidazolium | 3796.2 | 6187.3 | 2.62 | 0.66 | 0.44 | 10 |
| 9-B1 | 1:1 | $C_{10}$ BTA | 1537.7 | $C_{12}$ bisimidazolium | 3662.3 | 7020.0 | 2.70 | 0.68 | | |
| 9-B2 | 1:1.6 | $C_{10}$ BTA | 838.9 | $C_{12}$ bisimidazolium | 3197.0 | 5448.6 | 3.17 | 0.56 | | |
| 9-B3 | 1:1.6 | $C_{10}$ BTA | 838.9 | $C_{12}$ bisimidazolium | 3197.0 | 5448.6 | 2.7 | 0.63 | 0.47 | 16.4 |
| 10-A1 | 1:1.6 | $C_4$ BTA | 1138.0 | $C_{12}$ core, $C_3$ bisimidazolium | 4062.0 | 7800.0 | 3.17 | 0.59 | 0.47 | 17.5 |
| 10-A2 | 1:1.6 | $C_{10}$ BTA | 1361.3 | $C_{12}$ core, $C_3$ bisimidazolium | 3838.7 | 7800.0 | 3.12 | 0.58 | 0.47 | 27.5 |

*% Primary Bile Acids in feces as % of total measured: i.e. (Cholic acid + chenodeoxycholic acid) x 100/(Cholic acid + chenodeoxycholic acid + 3-OH-12Oxo-Cholanic Acid + deoxycholic acid + lithocholic acid)

Example 7

N,N,N',N'-tetrakis(3-aminopropyl)-1,4-butanediamine ($C_4$ BTA) terpolymers with 1-(3-aminopropyl)imidazole (API) as comonomer, and 1,10-dibromodecane (DBD), as crosslinking monomer Synthesis of crosslinked N,N,N',N'-tetrakis(3-aminopropyl)-1,4-butanediamine materials were conducted using parallel synthesis. A solution of N,N,N',N'-tetrakis(3-aminopropyl)-1,4-butanediamine (40 wt. % of a N,N-dimethylformamide (DMF) solution) was dispensed into 40 mL glass vials. 1,10-Dibromodecane (DBD), the crosslinking monomer and 1-(3-aminopropyl)imidazole (API), the comonomer, were added to each vial in the amounts described in the table below. Additional DMF and methanol were added resulting in a total solid content of 40 wt. % where the solvents were in at a ratio of 1:1 (by volume). The vials were capped and heated for 17 hours at 58° C. The resulting polymer gel was swollen and ground in MeOH, washed in MeOH (twice), NaOH (0.1M three times) then water (three times) and lyophilized until dry. Bile acid binding capacity, affinity, and retention for each resulting polymer were determined via the A assay, B assay and hamster model, and results are reported in the table below.

| Sample # | Monomer: Comonomer: Crosslinking Monomer Mole Ratio | DBD (mg) | C₄ BTA (uL) | API (uL) | DMF (uL) | methanol (uL) | BA binding affinity A assay (mmol/g) | BA binding capacity B assay (mmol/g) | BA binding retention Hamster (mmol/g) | BA binding % Primary Bile Acids in feces* | Swelling g/g |
|---|---|---|---|---|---|---|---|---|---|---|---|
| 11-D1 | 0.75:0.25:1.6 | 2588 | 1421 | 129 | 3426 | 3426 | 0.52 | 3.00 | 0.56 | 7.6 | 63.63 |
| 11-D2 | 0.5:0.5:1.6 | 3261 | 1119 | 405 | 3758 | 3758 | 0.56 | 2.92 | 0.62 | 10.4 | 49.36 |
| 11-D3 | 0.25:0.75:1.6 | 4406 | 605 | 876 | 4323 | 4323 | 0.58 | 2.66 | 0.52 | 10.7 | |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 8

N,N,N',N'-tetrakis(3-aminopropyl)-1,4-butanediamine ($C_4$ BTA) with guanidine hydrochloride as a crosslinking monomer Synthesis of polymers with guanidine hydrochloride as a crosslinker consisted of three components: N,N,N',N'-tetrakis(3-aminopropyl)-1,4-butanediamine monomer ($C_4$ BTA), guanidine hydrochloride, and a comonomer. All the reactions were carried out using an appropriate size round bottom flask with a nitrogen inlet port and hot plates equipped with silicon oil baths.

In a typical reaction, N,N,N',N'-tetrakis(3-aminopropyl)-1,4-butanediamine monomer was dispensed into a round bottom flask with a nitrogen inlet port. Then guanidine hydrochloride and comonomer (if present) were added to the flask. The reaction flasks were capped using a rubber septum and nitrogen flow was introduced from the nitrogen inlet port. The reaction flask were then heated for 18 hours at 120° C. and then for 4 hours at 180° C. The polymer formed was swollen and ground in 1M hydrochloric acid solution and then washed with ethanol (two times), water, 3M sodium hydroxide (two times) and water (three times) and lyophilized until dry. Bile acid binding capacity, affinity, and retention for each resulting polymer were determined via the A assay, B assay and hamster model and results are reported in the table below.

| Sample # | Crosslinking Monomer | Comonomer | C₄ BTA: crosslinker: Comonomer (mol ratio) | C₄ BTA (g) | Crosslinker (g) | Comonomer (g) | BA binding A assay (mmol/g) | BA binding B assay (mmol/g) | BA binding Hamster (mmol/g) | BA binding % Primary Bile Acids in feces* | Swelling g/g |
|---|---|---|---|---|---|---|---|---|---|---|---|
| 12-B5 | Guanidine HCl | None | 1:2:0 | 20.00 | 12.07 | 0 | 0.48 | 3.39 | 0.43 | 20.9 | |
| 13-A1 | Guanidine HCl | 1,6-diamino-hexane | 1:1.56:1.56 | 3.49 | 1.64 | 2.00 | 0.48 | 3.27 | 0.5 | 15.5 | 4.03 |
| 13-A2 | Guanidine HCl | 1,8-diamino-octane | 1:1.56:1.56 | 2.81 | 1.32 | 2.00 | 0.54 | 3.2 | 0.495 | 20.8 | 2.76 |
| 13-A3 | Guanidine HCl | 1,10-diamino-decane | 1:1.56:1.56 | 2.36 | 1.11 | 2.00 | 0.60 | 3.08 | 0.46 | 25.3 | 2.44 |
| 13-A4 | Guanidine HCl | 1,12-diamino-dodecane | 1:1.56:1.56 | 2.03 | 0.95 | 2.00 | 0.65 | 3.21 | 0.595 | 22.2 | 2.41 |
| 13-B1 | Guanidine HCl | 1,12-diamino-dodecane | 1:3.57:3.57 | 1.33 | 1.43 | 3.00 | 0.69 | 2.17 | 0.37 | 52.3 | 1.05 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

| Crosslinking monomer | Structure |
|---|---|
| TMBMP-DBD | 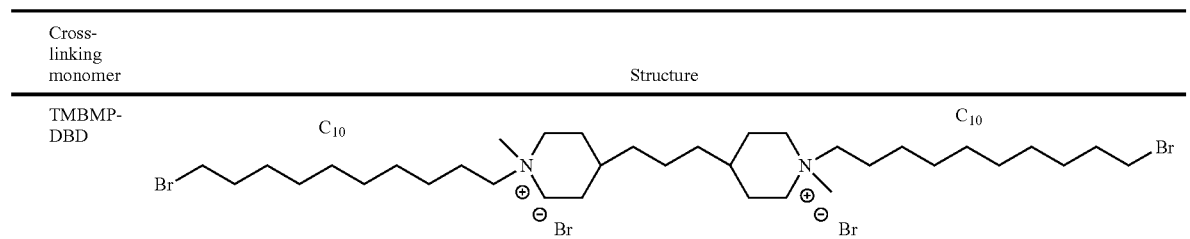 |

Bis-1-bromodecane-4,4'-trimethylenebis(1-methylpiperidine)

| Cross-linking monomer | Structure |
|---|---|
| TBMP-DBDD | 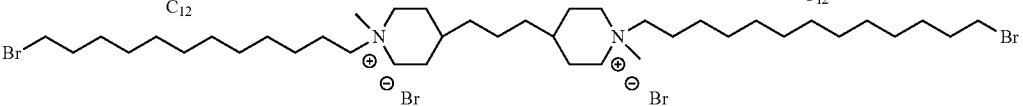<br>Bis-1-bromododecane-4,4'-trimethylenebis(1-methylpiperidine) |
| TMBMP-DBUD | 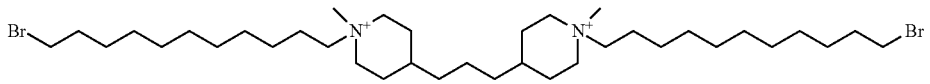 [SMILES: C[N+]1(CCCCCCCCCCCBr)CCC(CCCC2CC[N+](C)(CCCCCCCCCCCBr)CC2)CC1]<br>4,4'-(propane-1,3-diyl)bis(1-(11-bromoundecyl)-1-methylpiperidinium) |

Example 9

Synthesis of polymers of N,N,N',N'-tetrakis(3-aminopropyl)-1,4-butanediamine ($C_4$ BTA) and with dihalo bis piperidinium as crosslinkers and ligands Synthesis of polymers with dihalobis piperidinium as crosslinkers consisted of two components: N,N,N',N'-tetrakis(3-aminopropyl)-1,10-dacanediamine monomer ($C_{10}$ BTA) or N,N,N',N'-tetrakis(3-aminopropyl)-1,4-butanediamine ($C_4$ BTA) and dihalobis piperidinium (TMBMP-DBD). The reactions were carried out using a 250 mL size round bottom flask with a nitrogen inlet port and hot plates equipped with silicon oil baths.

In a typical reaction, a BTA monomer was dissolved in methanol to make a 50 wt. % solution and then dispensed into a round bottom flask. Then TMBMP-DBD or TMBMP-DBDD was added to the flask as a 50 wt. % solution in methanol. The reaction flasks were capped using a rubber septum and nitrogen flow was introduced from the nitrogen inlet port. The reaction flasks were then heated for 18 hours at 55° C. The polymers formed with $C_4$ BTA were swollen and ground in methanol and washed with methanol (two times), 1M hydrochloric acid, and water (three times) and lyophilized until dry. The polymers formed with $C_{10}$ BTA were swollen and ground in methanol and washed with methanol (two times), 0.5M hydrochloric acid, water, 0.5M sodium bicarbonate (two times) and water (three times) and lyophilized until dry. Bile acid binding capacity, affinity, and retention for each resulting polymer were determined via the A assay, B assay and hamster model and results are reported in the table below.

| Sample # | Amine monomer | Crosslinking Monomer | Monomer: crosslinker (mol ratio) | BTA (g) | $CH_3OH$ (g) | Crosslinking monomer (g) | Bile acid binding affinity A assay (mmol/g) | Bile acid binding capacity B assay (mmol/g) | Bile acid binding retention Hamster (mmol/g) | BA binding % Primary Bile Acids in feces* | Swelling g/g |
|---|---|---|---|---|---|---|---|---|---|---|---|
| 14-A1 | $C_4$ BTA | TBMP-DBD | 1:2 | 1.58 | 9.96 | 8.38 | 0.55 | 2.73 | 0.37 | 14.0 | 7.6 |
| 15-A1 | $C_{10}$ BTA | TBMP-DBD | 1:1.6 | 1.2 | 5.22 | 4.02 | 0.54 | 2.90 | | | 11.18 |
| 15-A2 | $C_{10}$ BTA | TBMP-DBDD | 1:1.6 | 1.2 | 5.49 | 4.29 | 0.66 | 2.79 | 0.53 | 18.8 | 1.83 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 10

Ligand Modification

Polymer synthesized with BTA and dihalobis piperidinium crosslinker were further modified by reacting with alkyl halides to attach a pendant alkyl ligand to the scaffold. In a typical reaction, polymer scaffold was first soaked in methanol in a 250 mL round bottom flask and then different amount of alkyl halide ligand (as listed in table below) was added to the flask. The reactions were carried out at 55° C. for 18 hours. The polymer were then washed with methanol (2 times), 1 M hydrochloric acid, 1 M sodium chloride (2 times), and water (3 times) and lyophilized until dry. Bile acid binding capacity, affinity, and retention for each resulting polymer were determined via the A assay, B assay and hamster model and results are reported in the table below.

| Sample # | Polymer scaffold | Ligand | Polymer scaffold: Ligand (mol ratio) | Polymer scaffold (g) | Methanol (g) | Ligand (g) | BA binding affinity A assay (mmol/g) | BA binding capacity B assay (mmol/g) | BA binding retention Hamster (mmol/g) | BA binding Hamster % Primary Bile Acids in feces* | Swelling g/g |
|---|---|---|---|---|---|---|---|---|---|---|---|
| 16-A1 | C$_4$ BTA/ TMBMP/DBD | C$_{10}$ alkyl | 1:0.95 | 2.8 | 31.6 | 1.2 | 0.65 | 2.25 | 0.38 | 4.6 | 3.22 |
| 16-A2 | C$_4$ BTA/ TMBMP/DBD | C$_{10}$ alkyl | 1:1.75 | 2.2 | 27.69 | 1.8 | 0.62 | 2.11 | | | 2.29 |
| 16-A3 | C4$_4$ BTA/ TMBMP/DBD | C$_{10}$ alkyl | 1:3.45 | 1.6 | 23.73 | 2.4 | 0.671 | 1.98 | 0.4 | 4.4 | 2.11 |

*% Primary Bile Acids in feces as % of total measured: i.e. (Cholic acid + chenodeoxycholic acid) × 100/ (Cholic acid + chenodeoxycholic acid + 3-OH-12Oxo-Cholanic Acid + deoxycholic acid + lithocholic acid)

Example 11

Synthesis of a crosslinker, Bis-1-bromo-decane-4,4'-trimethylenebis(1-methylpiperidine)

Into a round bottomed flask was weighed 60 g (0.20 moles) of dibromodecane and 20 mL of methanol. The flask was heated to 55° C. for 15-20 minutes. Then 10.0 g (0.041 mol) of 4,4'-Trimethylenebis(1-methylpiperidine) was added to the solution. The reaction mixture was allowed to stir for 12 hours and the reaction was stopped by the removal of heat and cooling to room temperature. The product was isolated by precipitation of the reaction solution into a solution of acetone:hexane 3:1 followed by filtration and washing with hexanes. The yield was 24.6 g 91% yield. The product was identified by $^1$H NMR and mass spec.

Example 12

Preparation of TMBMP-DBUD

A mixture of 11-bromoundecanol (31.65 g, 0.126 mol) and 4,4'-trimethylenebis(1-methylpiperidine) (5 g, 0.021 mol) in methanol (50 mL) was refluxed for 17 hours. Methanol was removed by rotary evaporation. To the residue was added toluene (100 mL) and the mixture was stirred at 50° C. for 2 hours. Solvent was removed by filtration. The solid was washed with toluene (100 mL) and ether (2×100 mL). After drying under high vacuum, 4,4'-(propane-1,3-diyl)bis(1-(11-hydroxyundecyl)-1-methylpiperidinium) was obtained as a white powder (15.5 g, 100%). MS m/e (M$^{2+}$), calculated 290.3. found 290.5.

4,4'-(propane-1,3-diyl)bis(1-(11-hydroxyundecyl)-1-methylpiperidinium) (15.5 g, 0.21 mol) was placed in a pressure flask. Hydrobromic acid (50 mL, 48 wt. % in water) was added and the flask was tightened to seal. The reaction was stirred at 120° C. for 17 hours. The reaction mixture was azeotroped with THF and toluene to remove excess hydrobromic acid. The residue was dried in vacuum oven at 35° C. for 24 hours to give 17.27 g crude product as a light brown powder (94.9% yield).

The crude product (4.02 g) was recrystallized in isopropanol (20 mL) to give 4,4'-(propane-1,3-diyl)bis(1-(11-bromoundecyl)-1-methylpiperidinium) as an off-white solid (3.11 g, 77.4% recovery). MS m/e (M$^{2+}$), calculated 353.2. found 353.3.

Example 13

N,N,N',N'-tetrakis(3-aminopropyl)-1,3-propanediamine (C$_3$ BTA), N,N,N',N'-tetrakis(3-aminopropyl)-1,8-octaneanediamine (C$_8$ BTA), N,N,N',N'-tetrakis(3-aminopropyl)-1,10-decanediamine (C$_{10}$ BTA) and N,N,N',N'-tetrakis(3-aminopropyl)-1,12-dodecanediamine (C12 BTA) gel synthesis Synthesis of N,N,N',N'-tetrakis(3-aminopropyl)-1,3-propanediamine, N,N,N',N'-tetrakis(3-aminopropyl)-1,8-octaneanediamine, N,N,N',N'-tetrakis(3-aminopropyl)-1,10-decanediamine and N,N,N',N'-tetrakis(3-aminopropyl)-1,12-dodecanediamine polymers materials were conducted using dispensing robots with liquid and powder dispensing capacities. N,N,N',N'-tetrakis(3-aminopropyl)-1,3-propanediamine or N,N,N',N'-tetrakis(3-aminopropyl)-1,8-octaneanediamine or N,N,N',N'-tetrakis(3-aminopropyl)-1,10-decanediamine or N,N,N',N'-tetrakis(3-aminopropyl)-1,12-dodecanediamine monomer was dispensed into 8 mL glass vials. Solutions of the crosslinking monomer of formula X—R$_1$—X wherein X is halo such as chloro or bromo and R$_1$ is a hydrocarbon chain listed in the examples below, 1,10-dibromodecane was dispensed at 40 wt. % in dimethyl sulfoxide (DMSO) and 1,12-dibromododecane was neat. Solvent was added to each vial to make the final solid content concentration at 40 wt %. Vials were equipped with magnetic stirrer, capped and heated for 17 hours at 60° C. Most vials contained a solid plug of polymer. The polymer was swollen and ground in dimethyl formamide (DMF), washed with aqueous hydrochloric acid (1 M), water, sodium hydroxide (0.01 M, three times), water (two times) and lyophilized until dry.

| Sample # | Monomer: cosslinker mole ratio | monomer | Wt. (mg) | Cross-linker (R$_1$) | wt (mg) | DMSO (mg) | Bile acid binding Capacity B assay (mmol/g) | Bile acid binding Affinity A assay (mmol/g) | Bile acid binding Retention Hamster (mmol/g) | Bile acid binding % Primary Bile Acids in feces* |
|---|---|---|---|---|---|---|---|---|---|---|
| 17-A1 | 1:0.5 | C$_8$ BTA | 300.0 | C$_{10}$ alkylene | 120.8 | 631.2 | | | | |
| 17-A2 | 1:0.5 | C$_{10}$ BTA | 300.0 | C$_{10}$ alkylene | 112.3 | 618.5 | | | | |
| 17-A3 | 1:0.5 | C$_{12}$ BTA | 300.0 | C$_{10}$ alkylene | 105.0 | 607.5 | | | | |
| 17-B1 | 1:1 | C$_8$ BTA | 300.0 | C$_{10}$ alkylene | 241.6 | 812.4 | 3.33 | | | |
| 17-B2 | 1:1 | C$_{10}$ BTA | 300.0 | C$_{10}$ alkylene | 224.7 | 787.0 | 3.22 | | | |
| 17-B3 | 1:1 | C$_{12}$ BTA | 300.0 | C$_{10}$ alkylene | 210.0 | 764.9 | 3.32 | | | |

-continued

| Sample # | Monomer:cosslinker mole ratio | monomer | Wt. (mg) | Cross-linker ($R_1$) | wt (mg) | DMSO (mg) | Bile acid binding Capacity B assay (mmol/g) | Bile acid binding Affinity A assay (mmol/g) | Bile acid binding Retention Hamster (mmol/g) | Bile acid binding % Primary Bile Acids in feces* |
|---|---|---|---|---|---|---|---|---|---|---|
| 17-C1 | 1:1.6 | $C_8$ BTA | 300.0 | $C_{10}$ alkylene | 386.6 | 1029.8 | 3.21 | | | |
| 17-C2 | 1:1.6 | $C_{10}$ BTA | 300.0 | $C_{10}$ alkylene | 359.5 | 989.2 | 2.91 | | | |
| 17-C3 | 1:1.6 | $C_{12}$ BTA | 300.0 | $C_{10}$ alkylene | 335.9 | 953.9 | 2.98 | | | |
| 17-D1 | 1:2.2 | $C_8$ BTA | 300.0 | $C_{10}$ alkylene | 531.5 | 1247.3 | 2.93 | | | |
| 17-D2 | 1:2.2 | $C_{10}$ BTA | 300.0 | $C_{10}$ alkylene | 494.3 | 1191.4 | 2.74 | | | |
| 17-D3 | 1:2.2 | $C_{12}$ BTA | 300.0 | $C_{10}$ alkylene | 461.9 | 1142.9 | 2.61 | | | |
| 18-A1 | 1:1.6 | $C_{10}$ BTA | 6368.8 | $C_{10}$ alkylene | 7631.2 | 21000.0 | 3.07 | 0.68 | | |
| 19-A1 | 1:1.6 | $C_{10}$ BTA | 2911.5 | $C_{10}$ alkylene | 3488.5 | 9600.0 | 3.15 | 0.68 | 0.49 | 25.1 |
| 19-A2 | 1:1.6 | $C_{12}$ BTA | 3019.1 | $C_{10}$ alkylene | 3380.9 | 9600.0 | 3.00 | 0.70 | 0.56 | 28.3 |
| 20-A2 | 1:1.6 | $C_8$ BTA | 150.0 | $C_{10}$ alkylene | 193.3 | 514.9 | | | | |
| 20-B2 | 1:2.2 | $C_8$ BTA | 150.0 | $C_{10}$ alkylene | 265.8 | 623.6 | 2.77 | | | |
| 20-C2 | 1:2.8 | $C_8$ BTA | 150.0 | $C_{10}$ alkylene | 338.2 | 732.4 | 2.54 | | | |
| 20-D2 | 1:3.4 | $C_8$ BTA | 150.0 | $C_{10}$ alkylene | 410.7 | 841.1 | 2.24 | | | |
| 21-A1 | 1:1.6 | $C_3$ BTA | 150.0 | $C_{10}$ alkylene | 238.2 | 582.3 | 3.32 | 0.61 | | |
| 21-B1 | 1:2.2 | $C_3$ BTA | 150.0 | $C_{10}$ alkylene | 327.5 | 716.3 | 3.24 | | | |
| 21-C1 | 1:2.8 | $C_3$ BTA | 150.0 | $C_{10}$ alkylene | 416.8 | 850.3 | 3.10 | 0.69 | | |
| 21-D1 | 1:3.4 | $C_3$ BTA | 150.0 | $C_{10}$ alkylene | 506.2 | 984.3 | 2.86 | 0.71 | | |
| 22-A1 | 1:1.6 | $C_3$ BTA | 2923.5 | $C_{12}$ alkylene | 5076.5 | 12000.0 | 3.03 | 0.68 | 0.64 | 26.2 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 14

BTA Monomers with Different Core Structures

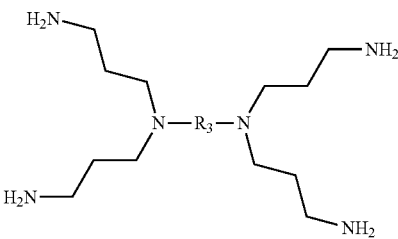

Synthesis of $N^1,N^{1'}$-(1,3-phenylenebis(methylene))bis($N^1$-(3-aminopropyl)propane-1,3-diamine) ($R_3$=1,3-phenylenedimethyl), $N^1,N^{1'}$-(1,4-phenylenebis(methylene))bis($N^1$-(3-aminopropyl)propane-1,3-diamine) ($R_3$=1,4-phenylenedimethyl), $N^2N^2,N^6,N^6$-tetrakis(3-aminopropyl)pyridine-2,6-dicarboxamide ($R_3$=2,6-diformylpyridine), $N^1,N^1,N^6,N^6$-tetrakis(3-aminopropyl)adipamide ($R_3$=1,6-dioxohexane-1,6-diyl), $N^1,N^1,N^4,N^4$-tetrakis(3-aminopropyl)succinamide ($R_3$=succinyl) and 1,3-bis(3-(bis(3-aminopropyl)amino)propyl)-1H-imidazol-3-ium ($R_3$=3,3'-(1H-imidazole-3-ium-1,3-diyl)dipropyl) crosslinked materials were conducted using dispensing robots with liquid and powder dispensing capacities. The selected monomer was dispensed into 8 mL glass vials. Solutions of the crosslinking monomer of formula X—$R_1$—X wherein X is halo such as chloro or bromo and $R_1$ is a hydrocarbon chain as listed in the table below was dispensed as 40 wt. % in dimethyl sulfoxide (DMSO). Solvents and $K_2CO_3$ were added to each vial. The vials were equipped with magnetic stirrer, capped and heated for 17 hours at 60° C. Most vials contained a solid plug of polymer. The polymer was swollen and ground in methanol, washed with aqueous hydrochloric acid (1 M), water, sodium hydroxide (0.01 M, three times), water (two times) and lyophilized until dry.

| Sample # | Crosslinking monomer | Monomer:crosslinker mole ratio | Monomer $R_3$ value | wt (mg) | 1,10-Dibromo-decane (mg) | $K_2CO_3$ (mg) | DMSO (mg) | BA binding Affinity A assay (mmol/g) | BA binding Capacity B assay (mmol/g) | BA binding Retention Hamster (mmol/g) | BA binding % Primary Bile Acids in feces* |
|---|---|---|---|---|---|---|---|---|---|---|---|
| 23-B1 | $C_{10}$ alkylene | 1:0.5 | 1,3-phenylenedimethyl | 400 | 102.9 | 568.6 | 754.3 | 0.672 | 2.7324 | | |
| 23-B2 | $C_{10}$ alkylene | 1:1 | 1,3-phenylenedimethyl | 400 | 205.8 | 568.6 | 908.6 | 0.6636 | 1.3948 | | |
| 23-C1 | $C_{10}$ alkylene | 1:0.5 | 2,6-diformylpyridine | 400 | 104.2 | 480 | 756.3 | | | | |
| 23-C2 | $C_{10}$ alkylene | 1:1 | 2,6-diformylpyridine | 400 | 208.4 | 480 | 912.7 | 0.6592 | 2.3176 | | |
| 23-D1 | $C_{10}$ alkylene | 1:0.5 | 1,6-dioxohexane-1,6-diyl | 400 | 115.8 | 426.6 | 773.7 | | | | |
| 23-D2 | $C_{10}$ alkylene | 1:1 | 1,6-dioxohexane-1,6-diyl | 400 | 231.5 | 426.6 | 947.3 | 0.6404 | 2.2948 | | |
| 24-A1 | $C_{10}$ alkylene | 1:1.6 | 1,3-phenylenedimethyl | 329.1 | 270.9 | 467.9 | 900 | 0.6586 | 1.3198 | | |
| 24-A2 | $C_{10}$ alkylene | 1:1.6 | 2,6-diformylpyridine | 327.2 | 272.8 | 392.7 | 900 | 0.6938 | 1.8654 | | |
| 24-A3 | $C_{10}$ alkylene | 1:1.6 | 1,6-dioxohexane-1,6-diyl | 311.5 | 288.5 | 332.2 | 900 | 0.6846 | 1.9758 | | |
| 25-A1 | $C_{10}$ alkylene | 1:1.6 | 1,3-phenylenedimethyl | 3949.4 | 3250.5 | 5614.3 | 10799.8 | 0.366 | 0.2862 | | |
| 25-A2 | $C_{10}$ alkylene | 1:1.6 | 1,3-phenylenedimethyl | 3926.3 | 3273.7 | 4711.9 | 10800 | 0.583 | 0.849 | 0.2 | 26.3 |
| 25-A3 | $C_{10}$ alkylene | 1:1.6 | 1,6-dioxohexane-1,6-diyl | 3983.9 | 3689.8 | 4248.7 | 11510.6 | 0.6502 | 1.495 | 0.25, 0.51 | 36.3, 29.2 |

| Sample # | Crosslinking monomer | Monomer: cross-linker mole ratio | Monomer R₃ value | wt (mg) | 1,10-Dibromo-decane (mg) | $K_2CO_3$ (mg) | DMSO (mg) | BA binding Affinity A assay (mmol/g) | BA binding Capacity B assay (mmol/g) | Retention Hamster (mmol/g) | BA binding % Primary Bile Acids in feces* |
|---|---|---|---|---|---|---|---|---|---|---|---|
| 26-A1 | $C_{10}$ alkylene | 1:0.5 | 1,3-phenylenedimethyl | 4600.6 | 1183.3 | 6540.1 | 8675.9 | 0.64905 | 2.7082 | | |
| 27-A1 | $C_{10}$ alkylene | 1:0.5 | 1,3-phenylenedimethyl | 2409.9 | 619.8 | 3425.8 | 4544.5 | 0.6652 | 2.6874 | | |
| 27-A2 | $C_{10}$ alkylene | 1:1 | 2,6-diformylpyridine | 2998.3 | 1562.4 | 3598.2 | 6841.1 | 0.5532 | 1.2818 | | |
| 28-A2 | $C_{10}$ alkylene | 1:1 | 1,3-phenylenedimethyl | 300 | 154.3 | 426.5 | 681.5 | 0.6668 | 2.8324 | | |
| 28-A3 | $C_{10}$ alkylene | 1:0.5 | 1,3-phenylenedimethyl | 300 | 231.5 | 426.5 | 797.2 | 0.6716 | 2.0856 | | |
| 29-A1 | $C_{10}$ alkylene | 1:0.5 | 1,3-phenylenedimethyl | 3943.4 | 1014.2 | 5605.8 | 7436.5 | 0.6628 | 2.1736 | | |
| 29-A2 | $C_{10}$ alkylene | 1:1 | 1,3-phenylenedimethyl | 2880.4 | 1481.7 | 4094.7 | 6543.2 | 0.67 | 1.8818 | | |
| 30-A1 | $C_{10}$ alkylene | 1:0.8 | 3,3'-(1H-imidazole-3-ium-1,3-diy)dipropyl | 300 | 108.2 | 373.6 | 612.2 | 0.573 | 2.889 | | |
| 30-A2 | $C_{10}$ alkylene | 1:1.2 | 3,3'-(1H-imidazole-3-ium-1,3-diyl)dipropyl | 300 | 162.2 | 373.6 | 693.3 | 0.617 | 2.7334 | | |
| 31-A1 | $C_{10}$ alkylene | 1:0.8 | 3,3'-(1H-imidazole-3-ium-1,3-diyl)dipropyl | 2001.4 | 721.5 | 2492.5 | 4084.5 | 0.6018 | 2.9138 | | |
| 31-A2 | $C_{10}$ alkylene | 1:1.2 | 3,3'-(1H-imidazole-3-ium-1,3-diyl)dipropyl | 2001.4 | 1082.1 | 2492.5 | 4624.8 | 0.6374 | 2.4926 | 0.5 | 16.2 |
| 32-A1 | $C_{10}$ alkylene | 1:0.8 | 3,3'-(1H-imidazole-3-ium-1,3-diyl)dipropyl | 4700 | 1694.4 | 5853.3 | 9591.6 | 0.638 | 2.3254 | 0.5 | 19.8 |
| 33-A1 | $C_{10}$ alkylene | 1:0.8 | Succinyl | 400 | 195.83 | 450.99 | 795.1 | 0.62 | 2.86 | | |
| 33-A2 | $C_{10}$ alkylene | 1:1.2 | Succinyl | 400 | 293.74 | 450.99 | 892.9 | 0.66 | 2.48 | | |
| 33-A3 | $C_{10}$ alkylene | 1:1.6 | Succinyl | 400 | 391.66 | 450.99 | 990.7 | 0.66 | 1.78 | | |
| 33-A4 | $C_{10}$ alkylene | 1:1.2 | Succinyl | 4000 | 2937.42 | 4509.85 | 8929.3 | 0.65 | 2.71 | 0.59 | 14.5 |
| 33-B1 | $C_{12}$ alkylene | 1:0.8 | Succinyl | 400 | 214.14 | 450.99 | 813.4 | 0.68 | 1.83 | | |
| 33-B2 | $C_{12}$ alkylene | 1:1.2 | Succinyl | 400 | 321.21 | 450.99 | 920.4 | 0.68 | 2.31 | | |
| 33-B3 | $C_{12}$ alkylene | 1:1.6 | Succinyl | 400 | 428.28 | 450.99 | 1027.3 | 0.66 | 1.33 | | |
| 33-B4 | $C_{12}$ alkylene | 1:1.2 | Succinyl | 4000 | 3212.11 | 4509.85 | 9203.7 | 0.68 | 1.95 | 0.39 | 25.0 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 15

$N^1,N^{1'}$-(1,3-phenylenebis(methylene))bis($N^1$-(3-aminopropyl)propane-1,3-diamine)

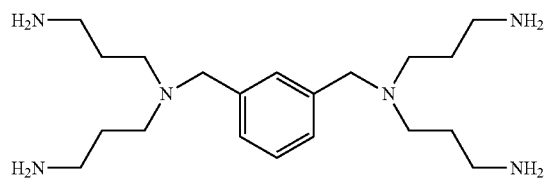 [SMILES: NCCCN(CCCN)Cc1cccc(CN(CCCN)CCCN)c1]

Tert-butyl 3,3'-azanediylbis(propane-3,1-diyl)dicarbamate (14.0 g, 0.038 mol) was dissolved in 150 mL of acetonitrile. To the solution was added 1,3-bis(chloromethyl)benzene (3.34 g, 0.019 mol), followed by diisopropylethylamine (13.2 mL, 0.076 mol). The reaction was stirred at 60° C. for 20 hours. The solvent was removed and the residue was purified by flash chromatography (silica gel, 15% methanol in dichloromethane) to give 7.56 g (52%) of pure tert-butyl-3,3',3",3"'-(1,3-phenylenebis(methylene))bis(azanetriyl)tetrakis(propane-3,1-diyl)tetracarbamate as a brown oil. MS m/e (MH⁺), calculated 765.55. found 765.67.

Tert-butyl 3,3',3",3"'-(1,3-phenylenebis(methylene))bis(azanetriyl)tetrakis-(propane-3,1-diyl)tetracarbamate (7.56 g, 0.099 mol) was dissolved in 40 mL of dichloromethane. To the solution was added trifluoroacetic acid (30.5 mL, 0.396 mol). The reaction was stirred at room temperature for 16 hours. Solvent was removed under reduced pressure and toluene (100 mL) was added to the residue to form a heteroazeotrope. After removal of toluene and remaining trifluoroacetic acid, a brown semi-solid was formed. To the residue was added 4N hydrochloric acid in dioxane (40 mL) and the mixture was stirred at room temperature for 30 minutes. A light brown solid formed. Ethyl ether (150 mL) was added to the mixture and the solid was filtered, washed with ethyl ether and dried under high vacuum to give 5.78 g $N^1,N^{1'}$-(1,3-phenylenebis(methylene))bis($N^1$-(3-aminopropyl)propane-1,3-diamine) as a hexahydrochloride salt in quantitative yield. MS m/e (MH⁺), calculated 365.33. found 365.39.

Example 16

$N^2,N^2,N^6,N^6$-tetrakis(3-aminopropyl)pyridine-2,6-dicarboxamide

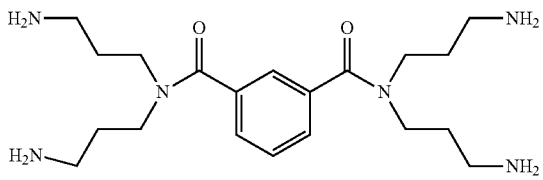 [SMILES: NCCCN(CCCN)C(=O)c1cccc(C(=O)N(CCCN)CCCN)c1]

A solution of tert-butyl 3,3'-azanediylbis(propane-3,1-diyl)dicarbamate (9.94 g, 0.03 mol) and diisopropylethyl amine (7.82 mL, 0.045 mol) in 200 mL of dichloromethane was cooled to 4° C. in an ice bath. Pyridine-2,6-dicarbonyl dichloride (3.06 g, 0.015 mol) was dissolved in 50 mL of dichloromethane and was added to the solution of tert-butyl 3,3'-azanediylbis(propane-3,1-diyl)dicarbamate dropwise. The internal temperature remained at or below 4° C. during the addition. After the addition, the reaction was warmed to room temperature and stirred for 3 hours. The reaction solution was washed with 1N HCl (2×150 mL), brine (150 mL), saturated NaHCO$_3$ solution (150 mL), and brine (150 mL). The organic phase was dried over MgSO$_4$ and concentrated. The crude product was passed through a silica gel plug (15% methanol in dichloromethane) to give 11.2 gram of tetra-Boc-protected N$^2$,N$^2$,N$^6$,N$^6$-tetrakis(3-aminopropyl)pyridine-2,6-dicarboxamide as a white solid (94%). MS m/e (MH$^+$), calculated 794.50. found 794.71.

To a solution of tetra-Boc-protected N$^2$,N$^2$,N$^6$,N$^6$-tetrakis (3-aminopropyl)pyridine-2,6-dicarboxamide (11.1 g, 0.014 mol) in 80 mL of dichloromethane was added trifluoroacetic acid (21.6 mL, 0.28 mol). The reaction was stirred at room temperature for 3 hours. Solvent was removed under reduced pressure and toluene (100 mL) was added to the residue to form a heteroazeotrope. Solvent and remaining trifluoroacetic acid were removed under reduced pressure. To the residue was added 4N HCl in dioxane (25 mL). The mixture was stirred at room temperature for 30 minutes and a white solid formed. Ethyl ether (150 mL) was added to the mixture and the solid was filtered, washed with ethyl ether and dried under high vacuum to give N$^2$,N$^2$,N$^6$,N$^6$-tetrakis (3-aminopropyl)pyridine-2,6-dicarboxamide as penta-hydrochloride salt in quantitative yield (8.02 g). MS m/e (MH$^+$), calculated 394.29. found 394.3.

Example 17

N$^1$,N$^1$,N$^6$,N$^6$-tetrakis(3-aminopropyl)adipamide

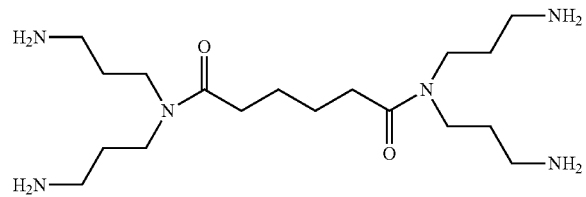 [SMILES: NCCCN(CCCN)C(=O)CCCCC(=O)N(CCCN)CCCN]

The title compound was prepared using same procedure described above for N$^2$,N$^2$,N$^6$,N$^6$-tetrakis(3-aminopropyl) pyridine-2,6-dicarboxamide. After drying under high vacuum, 6.03 g of N$^1$,N$^1$,N$^6$,N$^6$-tetrakis(3-aminopropyl)adipamide tetra-hydrochloride salt was obtained as a white solid (78%). MS m/e (MH$^+$), calculated 373.33. found 373.4.

Example 18

N$^1$,N$^1$,N$^4$,N$^4$-tetrakis(3-aminopropyl)succinamide

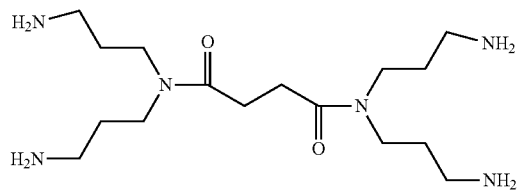 [SMILES: NCCCN(CCCN)C(=O)CCC(=O)N(CCCN)CCCN]

A solution of tert-butyl 3,3'-azanediylbis(propane-3,1-diyl)dicarbamate (15.0 g, 0.045 mol) and diisopropylethyl amine (8.6 mL, 0.0495 mol) in 200 mL of dichloromethane was cooled to 4° C. in ice bath. Succinyl chloride (2.68 mL, 0.0226 mol) was dissolved in 50 mL of dichloromethane and was added to the solution of tert-butyl 3,3'-azanediylbis (propane-3,1-diyl)dicarbamate dropwise. The internal temperature remained at or below 4° C. during the addition. After the addition, the reaction was warmed to room temperature and stirred for 2 hours. The reaction solution was washed with 1:1 mixture of 1N HCl and brine (2×150 mL), saturated NaHCO$_3$ solution (200 mL), and brine (200 mL). Organic phase was dried over MgSO$_4$ and concentrated. The crude product was purified on silica gel column (5-10% methanol in dichloromethane) to give 14.92 gram of t-Boc-protected N$^1$,N$^1$,N$^4$,N$^4$-tetrakis(3-aminopropyl)succinamide as a brown solid (88.6%).

A solution of tetra-Boc-protected N$^1$,N$^1$,N$^4$,N$^4$-tetrakis(3-aminopropyl)succinamide (14.9 g, 0.02 mol) in 4N HCl in dioxane (100 mL, 0.4 mol) was stirred at room temperature overnight. Precipitate formed in the solution. Diethylether (100 mL) was added to the reaction mixture. The slurry was stirred at room temperature for 30 min. Solid was filtered under nitrogen blanket and washed with diethylether (3×100 mL). After removal of residue solvent, desired product was obtained in quantitative yield as a tetrahydrochloride salt. MS m/e (MH$^+$), calculated 345.29. found 345.3.

Example 19

1,3-bis(3-(bis(3-aminopropyl)amino)propyl)-1H-imidazol-3-ium

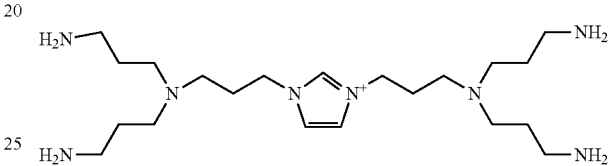

To a solution of 1,3-bis(3-iodopropyl)-1H-imidazol-3-ium iodide (5.02 g, 9.4 mmol) in 100 mL of acetonitrile was added tert-butyl 3,3'-azanediylbis(propane-3,1-diyl)dicarbamate (6.25 g, 18.8 mmol), followed by diisopropylethylamine (4.08 mL, 23.5 mmol). The reaction was stirred at 60° C. for 16 hours. Solvent was removed under reduced pressure. The crude product was purified by flash chromatography (silca gel, 15% methanol in dichloromethane containing 1% trimethylamine) 1,3-bis(3-(bis(3-(tert-butoxycarbonylamino)propyl)amino)propyl)-1H-imidazol-3-ium iodide was obtained as white solid (5.8 g, 66%). MS m/e (MH$^+$), calculated 811.6. found 811.7.

A mixture of 1,3-bis(3-(bis(3-(tert-butoxycarbonylamino) propyl)amino)propyl)-1H-imidazol-3-ium iodide (5.5 g, 5.8 mmol) in 4N HCl in dioxane (58.6 mL, 234 mmol) was stirred at room temperature overnight. Solvent was removed under reduced pressure. Toluene (3×100 mL) was added to form a heteroazeotrope. After removal of toluene and residue solvent, the desired product was obtained as a hexahydrochloride salt in quantitative yield. MS m/e (MH$^+$), calculated 411.39. found 411.4.

Example 20

Synthesis of Imidazolium Crosslinkers

Synthesis of Bis imiazole-n-alkane. A solution of Na-imidazole (0.1 mol) (imidazole sodium derivative, Aldrich 197637, CAS 5587-42-8) in 100 mL THF was prepared. An appropriate amount of the dialkyl bromide was added and the mixture was stirred overnight at room temperature. The solids were filtered off and the filtrate was dried under vacuum. The product was purified by column chromatography using 500 g of silica and ethyl acetate. The resulting yield was 50-80%. The product was identified by $^1$H NMR and mass spec.

Synthesis of 1-alkyl-3-(1-bromoalkyl) imidazolium bromide. Dibromoalkane (0.3 mol) was placed into a 3-necked flask that was fitted with an overhead stirrer. Acetone was added such that the resulting solution was 3 M. Alkyl imidazole (0.03 mol) was dissolved in acetone to result in a 2M solution. This was added to the flask and the reaction was stirred overnight at 45-50° C. The next day, the acetone was vacuumed off and the product was purified by column chromatography using 500 g of silica gel and 90:10 $CH_2Cl_2$: MeOH. The yield was in the range of 60-70% of materials that ranged from a clear oil to a white sold. Product was identified by $^1H$ NMR and mass spec.

Synthesis of polymer modified with 1,3-dialkylimidazolium bromide. The desired polyamine scaffold gel was dissolved in water and neutralized with an equimolar solution of NaOH. An appropriate amount of a solution of 1,3-dialkylimidazolium bromide in methanol was added to the polyamine solution. The mixture was heated to 75° C. for 24 hours. After cooling to room temperature the modified polyamine gel was washed by exposing the gel to a 2× methanol wash, 0.5 M HCl wash and 2× water washes. Each wash consisted of a process where the gel was stirred for 30 minutes, exposed to the washing solvent, centrifuged and the supernatant liquid was decanted off, and the wash solvent was added. After the final water wash, the gel was placed into a lyophilizer to remove the water. The gel was isolated as a white fluffy material.

Synthesis of n-alkyl bisimidazole. Imidazole sodium derivative (27 g, 0.29 moles) and tetrabutyl ammonium hydrogen sulfate (2.2 g, 6 mmol) (both commercially available from Aldrich) was weighed into a 1 L, 3 necked flask. An overhead stirrer, a condenser with a feed of dry, inert atmosphere was fitted to the flask. The remaining neck was fitted with a rubber septa. Anhydrous THF (250 mL) was added to the flask and stirred for 1 hour at room temperature. An appropriate amount of alkyl dibromide (1,12 dibromododecane, 16.g, 0.049 mol) in 50 mL THF was added. After stirring for 3-5 days and monitoring the progress with TLC, the solids were filtered off and the filtrate was dried under reduced pressure to generate an oil. The product was purified by adding $CH_2Cl_2$ and washing five times with water and then washing the organic layer with anhydrous magnesium sulfate. The purity was monitored by TLC (10% MeOH, 90% $CH_2Cl_2$), until no starting imidazole was present. The resulting yields were in the range of 80-90%. $^1H$ NMR ($CD_3OD$, 25° C., δ (ppm): 7.62 (s), 7.1, 6.90 (imidazole), 4.0 (tr), 1.8 (br), 1.25 (br, alkane). A similar synthesis procedure was used for 1,10-dibromodecane.

Synthesis of bis(1-bromoalkyl imidazolium bromide)alkane. In a dry sealed round bottomed flask, an appropriate amount of dibromoalkane (dibromododecane 48.7 g, 0.14 mol) was taken and 49 g of acetone, 1 g of MeOH was added as solvent. To this, freshly prepared n-alkyl bisimidazole (10 g, 0.033 mol) was added dropwise. It was heated at 55° C. for 2-3 days. The product was isolated by precipitating the product. The reaction solution was allowed to cool to room temperature and then this was added slowly to a glass beaker containing 250 mL of hexanes being rapidly stirred. The product form a precipitate oil. The hexanes were removed and the precipitate was stirred/washed with the following solvents to remove excess dibromoalkane; ethylacetate and diethyl ether. The white precipitate was placed in a vacuum oven to remove excess organic solvent.

The yields were in the range of 60%. $^1H$ NMR ($CD_3OD$, 25° C., δ (ppm): 9.1 (s), 7.7 (imidazolium), 4.21 (tr, —$CH_2$-imidazolium), 3.4 (—$CH_2Br$), 1.9 (br), 1.4 (br, alkane). A similar synthesis procedure was used to prepare all bisimidazolium alkylhalide crosslinkers e.g. bis imidazolium $C_{10}$ crosslinker, bis imidazolium $C_{12}$ crosslinker, bis imidazolium $C_{12}$ core $C_3$ crosslinker.

Example 21

Synthesis of a crosslinker, Bis-1-alkyl-4,4'-Trimethylenebis(1-methylpiperidine) ligand Into a round bottomed flask was weighed 42.34 g (0.20 moles) of dibromopropane and 20 mL of methanol. The flask was heated to 55° C. for 15-20 minutes. Then 10.0 g (0.041 mol) of 4,4'-trimethylenebis(1-methylpiperidine) was added to the solution. The reaction mixture was allowed to stir for 12 hours and the reaction was stopped by the removal of heat and cooling to room temperature. The product was isolated by precipitation of the reaction solution into a solution of acetone:hexane 3:1 followed by filtration and washing with hexanes. The yield was 24.6 g (91% yield). The product was identified by $^1H$ NMR and mass spectrometry.

Example 22

Monomer Approach Towards the Synthesis of Ligand-Containing N,N,N',N'-tetrakis(3-aminopropyl)-1,4-butanediamine ($C_4$ BTA) polymers Synthesis of ligand-containing BTA polymers by the monomer approach was conducted in a 4×6 library format with 8 mL vials. N-alpha-(tert-butoxycarbonyl)-L-tryptophan N-succinimidyl ester (Boc-Trp-Osu) was obtained commercially (TCI America CAS 3392-11-8). The synthesis was conducted in a two step process.

Step 1 (Recipe for BTA modified with ligand). A 75 wt. % solution of N,N,N',N'-tetrakis(3-aminopropyl)-1,4-butanediamine ($C_4$ BTA) in N-methylpyrrolidone (NMP) was dispensed into the vials, followed by a solution of ligand (20 wt. % in NMP). The vials were sealed and the mixture was stirred at 80° C., stirring at 500 RPM for 18 hours, then cooled to room temperature. Attachment of the ligand to $C_4$ BTA was confirmed using MS. The amounts of the $C_4$ BTA, NMP, and Boc-Trp-OSu use are listed in the table below.

Step 2 (Crosslinking the modified BTA monomer). The $C_4$ BTA-ligand mixture was subsequently treated with neat 1,10-dibromodecane (DBD) or epichlorohydrin (ECH). The reactions were sealed and heated at 80° C. for 18 hours with stirring at 500 RPM until the reaction mixture gelled. Samples that gelled were washed with methanol (2×), 1M NaOH solution, water (3×), then lyophilized dry. The amounts for the reactants are listed in the table below.

| Recipe # | $C_4$ BTA | NMP | Boc-Trp-OSu |
|---|---|---|---|
| 100-A1 | 911.14 | 1459.15 | 288.86 |
| 100-A2 | 734.37 | 2107.32 | 465.63 |
| 100-A3 | 529.07 | 2860.07 | 670.93 |
| 100-A4 | 339.34 | 3555.74 | 860.66 |

| Sample # | Amine Monomer | Ligand | Cross-linker | Amine: Cross-linker Mol Ratio | Ligand: Amine Mol Ratio to BTA | 100-A1 (mg) | 100-A2 (mg) | 100-A3 (mg) | 100-A4 (mg) | Cross-linker (mg) | BA binding affinity A assay (mmol/g) | BA binding capacity B assay (mmol/g) |
|---|---|---|---|---|---|---|---|---|---|---|---|---|
| 34-A1 | BTA | Boc-Trp-Osu | ECH | 1:2 | 1:0.25 | 650.435 | 0 | 0 | 0 | 130.28 | 0.47 | 2.95 |

-continued

| | | | | | | | | | | | | |
|---|---|---|---|---|---|---|---|---|---|---|---|---|
| 34-A2 | BTA | Boc-Trp-Osu | ECH | 1:4 | 1:0.25 | 650.435 | 0 | 0 | 0 | 260.56 | 0.41 | 0.62 |
| 34-A3 | BTA | Boc-Trp-Osu | ECH | 1:6 | 1:0.25 | 650.435 | 0 | 0 | 0 | 390.85 | 0.37 | 0.68 |
| 34-A4 | BTA | Boc-Trp-Osu | ECH | 1:8 | 1:0.25 | 650.435 | 0 | 0 | 0 | 521.13 | 0.36 | 1.01 |
| 34-B1 | BTA | Boc-Trp-Osu | ECH | 1:2 | 1:0.5 | 0 | 0 | 0 | 0 | 104.69 | 0.44 | 2.42 |
| 34-B2 | BTA | Boc-Trp-Osu | ECH | 1:4 | 1:0.5 | 0 | 0 | 0 | 0 | 209.38 | 0.42 | 1.26 |
| 34-B3 | BTA | Boc-Trp-Osu | ECH | 1:6 | 1:0.5 | 0 | 806.535 | 0 | 0 | 314.06 | 0.38 | 1.23 |
| 34-B4 | BTA | Boc-Trp-Osu | ECH | 1:8 | 1:0.5 | 0 | 806.535 | 0 | 0 | 418.75 | 0.37 | 1.15 |
| 35-A1 | BTA | Boc-Trp-Osu | DBD | 1:1 | 1:0.5 | 0 | 806.535 | 0 | 0 | 211.27 | 0.57 | 3.20 |
| 35-A2 | BTA | Boc-Trp-Osu | DBD | 1:2 | 1:0.25 | 0 | 806.535 | 0 | 0 | 422.54 | 0.65 | 2.31 |
| 35-A3 | BTA | Boc-Trp-Osu | DBD | 1:3 | 1:0.25 | 0 | 0 | 0 | 0 | 633.81 | 0.55 | 1.06 |
| 35-A4 | BTA | Boc-Trp-Osu | DBD | 1:4 | 1:0.25 | 0 | 0 | 0 | 0 | 845.09 | N/A | 1.81 |
| 35-B1 | BTA | Boc-Trp-Osu | DBD | 1:1 | 1:0.5 | 0 | 0 | 1013.94 | 0 | 169.77 | 0.58 | 2.80 |
| 35-B2 | BTA | Boc-Trp-Osu | DBD | 1:2 | 1:0.5 | 0 | 0 | 1013.94 | 0 | 339.54 | 0.63 | 1.74 |
| 35-B3 | BTA | Boc-Trp-Osu | DBD | 1:3 | 1:0.5 | 0 | 0 | 1013.94 | 0 | 509.30 | 0.46 | 0.63 |
| 35-B4 | BTA | Boc-Trp-Osu | DBD | 1:4 | 1:0.5 | 0 | 0 | 1013.94 | 0 | 679.07 | 0.48 | 0.76 |
| 35-C1 | BTA | Boc-Trp-Osu | DBD | 1:1 | 1:1 | 0 | 167.56 | 0 | 0 | 125.25 | N/A | 1.12 |
| 35-C2 | BTA | Boc-Trp-Osu | DBD | 1:2 | 1:1 | 0 | 167.56 | 0 | 0 | 250.51 | 0.54 | 0.88 |
| 35-C3 | BTA | Boc-Trp-Osu | DBD | 1:3 | 1:1 | 0 | 167.56 | 0 | 1119.4693 | 375.76 | 0.54 | 0.83 |

*Boc-Trp-Osu is 2-(tert-butoxycarbonylamino)-3-1H-indo-3-yl)-1 oxopropanyl
Animal samples prepared by the monomer approach follow.

| Sample # | Ligand | Amine:Cross-linker Mol Ratio | Ligand:Amine Mol Ratio | BTA (mg) | Ligand (mg) | NMP (uL) | Cross-linker (mg) | BA binding A assay (mmol/g) | BA binding B assay (mmol/g) | BA binding Hamster (mmol/g) | BA binding % Primary Bile Acids in feces* | Swelling (g/g) |
|---|---|---|---|---|---|---|---|---|---|---|---|---|
| 36-A1 | Boc-Trp-Osu | 1 | 0.25 | 3037.1 | 962.9 | 4731.4 | 2879.1 | 0.57 | 3.20 | 0.62 | 12.0 | 0.92 |
| 37-A1 | Boc-Trp-Osu | 1 | 0.25 | 5315 | 1685 | 1685 | 5038.4 | 0.58 | 3.28 | 0.51 | 17.7 | 0.80 |
| 38-B1 | Trp (De-Boc of 36-A1) | 1 | 0.25 | 3037.1 | 962.9 | 4731.4 | 2879.1 | 0.59 | 3.27 | 0.55 | 14.8 | 0.62 |
| 39-A1 | Amphiphilic | 0.33 | 0.25 | 2994.77 | 1005.2 | 18579.1 | N/A | 0.67 | 1.57 | 0.28 | 31.9 | 0.81 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Preparation of de-Boc Trp animal sample (38-B1). Following the attachment of Boc-Trp-OSu ligand onto the polymer as described above, the polymer was treated with two additional washes of HCl in dioxane (4M). The polymer was then washed with water, 10 vol. % NH$_4$OH (2×), and water (3×) before lyophilizing dry.

Example 23

Scaffold Approach Towards the Synthesis of Ligand-Containing C$_4$ BTA Polymers The scaffold was prepared by mixing C$_4$ BTA neat with a 50 wt. % 1,10-dibromodecane (DBD) in N-methylpyrrolidone (NMP). Additional NMP was added to give a total concentration of crosslinker and C$_4$ BTA equal to 37.5 wt. %. The mixture was heated at 70° C. stirring at 400 RPM until the mixture formed a gel. The gel was continued to be heated for a total of 22 hours before cooling. The solid was ground in methanol, washed with methanol, 1M NaCl, MeOH, water (3×), then lyophilized dry to give tacky particles.

The scaffold was portioned out into a 4×6 library plate with 8 mL vials. To this was added a 20 wt. % solution of ligand (thiazolium) in NMP. The vials were filled with NMP to achieve a total volume of 2.5 mL. The mixture was stirred at 80° C. for 18 hours, stirring at 500 RPM. Reactions were cooled, washed with methanol, 1M NaOH, and water, then lyophilized dry. The amounts used for the reactions follow.

| Sample # | Amine Monomer | Ligand | Cross-linker | Amine: Crosslinker Mol Ratio | Ligand: Amine Mol Ratio | BTA-DBD Scaffold (mg) | Ligand (mg) | NMP (uL) | BA binding affinity A assay (mmol/g) | BA binding capacity B assay (mmol/g) |
|---|---|---|---|---|---|---|---|---|---|---|
| 40-A1 | BTA | None | DBD | 0.625 | 0 | 300 | 0 | 2380 | 0.60 | 3.29 |
| 40-A2 | BTA | Thiazolium | DBD | 0.625 | 0.04 | 300 | 5.78 | 2374.22 | 0.60 | 3.29 |
| 40-A3 | BTA | Thiazolium | DBD | 0.625 | 0.08 | 300 | 11.56 | 2368.44 | 0.61 | 3.27 |
| 40-A4 | BTA | Thiazolium | DBD | 0.625 | 0.12 | 300 | 17.33 | 2362.67 | 0.60 | 3.23 |
| 40-A5 | BTA | Thiazolium | DBD | 0.625 | 0.16 | 300 | 23.11 | 2356.89 | 0.60 | 3.21 |
| 40-A6 | BTA | Thiazolium | DBD | 0.625 | 0.2 | 300 | 28.89 | 2351.11 | 0.61 | 3.20 |
| 40-B1 | BTA | Thiazolium | DBD | 0.625 | 0.25 | 300 | 36.11 | 2343.89 | 0.60 | 3.23 |
| 40-B2 | BTA | Thiazolium | DBD | 0.625 | 0.3 | 300 | 43.33 | 2336.67 | 0.60 | 3.17 |
| 40-B3 | BTA | Thiazolium | DBD | 0.625 | 0.35 | 300 | 50.56 | 2329.44 | 0.61 | 3.22 |
| 40-B4 | BTA | Thiazolium | DBD | 0.625 | 0.4 | 300 | 57.78 | 2322.22 | 0.60 | 3.20 |
| 40-B5 | BTA | Thiazolium | DBD | 0.625 | 0.45 | 300 | 65.00 | 2315 | 0.59 | 3.12 |
| 40-B6 | BTA | Thiazolium | DBD | 0.625 | 0.5 | 300 | 72.22 | 2307.78 | 0.61 | 3.16 |

Animal samples prepared by the scaffold approach are listed below:

| Sample # | Ligand | Solvent | Amine: Crosslinker Mol Ratio | Ligand: Amine Mol Ratio | BTA-DBD Scaffold (mg) | Ligand (mg) | Solvent (uL) |
|---|---|---|---|---|---|---|---|
| 41-A2 | Amphiphilic | NMP | 0.625 | 0.25 | 3000 | 399.4 | 28410.6 |
| 41-A1 | Amphiphilic | NMP | 0.625 | 0.1 | 3000 | 159.8 | 28650.2 |
| 41-B2 | Boc-Trp-Osu | NMP | 0.625 | 0.25 | 3000 | 377.3 | 28432.7 |
| 42-A1 | Tryptamine | NMP | 0.625 | 0.25 | 3000 | 261.4 | 18548.6 |
| 43-A3 | Thiazolium | NMP | 0.625 | 0.25 | 3000 | 358.1 | 18451.9 |
| 37-A3 | Thiazolium | NMP | 0.625 | 0.5 | 3000 | 716.2 | 18093.8 |
| 44-B6 | $C_{10}$ Pyridinium | NMP | 0.625 | 0.25 | 3000 | 356.4 | 38453.6 |
| 43-A2 | 3-(2-Bromoethyl Indole) | NMP | 0.625 | 0.1 | 3000 | 84.2 | 18725.8 |
| 44-A1 | $C_3$ thiophenium | DMSO | 0.625 | 0.25 | 3000 | 361 | 18449 |
| 44-A2 | $C_3$ thiophenium | DMSO | 0.625 | 0.5 | 3000 | 721.9 | 18088.1 |
| 45-A1 | (3-Bromopropyl) trimethyl-ammonium bromide | DMSO | 0.625 | 0.25 | 5000 | 408.77 | 17608.23 |
| 45-A2 | $C_3$ methyl imidazolium | DMSO | 0.625 | 0.25 | 5000 | 447.92 | 17569.08 |
| 45-A3 | $C_3$ pyrrolidinium | DMSO | 0.625 | 0.25 | 5000 | 435.44 | 17581.56 |
| 45-A4 | $C_3$ benz-thiazolium | DMSO | 0.625 | 0.25 | 5000 | 527.87 | 17489.13 |
| 45-A5 | $C_3$ methyl thiazolium | DMSO | 0.625 | 0.25 | 5000 | 620.35 | 17396.65 |

| Sample # | BA binding affinity A assay (mmol/g) | BA binding capacity B assay (mmol/g) | BA binding retention Hamster (mmol/g) | Bile acid binding % Primary Bile Acids in feces* | Swelling (g/g) |
|---|---|---|---|---|---|
| 41-A2 | 0.65 | 3.17 | 0.58 | 4.3 | 1.29 |
| 41-A1 | 0.64 | 3.25 | 0.62 | 5.7 | 1.00 |
| 41-B2 | 0.64 | 3.11 | 0.51 | 3.0 | 1.50 |
| 42-A1 | 0.62 | 3.25 | 0.60 | 8.1 | 0.64 |
| 43-A3 | 0.62 | 3.23 | 0.73, 0.42 | 6.4, 5.2 | 1.33 |
| 37-A3 | 0.59 | 2.99 | 0.35 | 6.4 | 8.30 |
| 44-B6 | 0.59 | 3.04 | 0.55 | 9.0 | 24.20 |
| 43-A2 | 0.62 | 3.25 | 0.67 | 6.1 | N/A |
| 44-A1 | 0.62 | 3.26 | | | 1.23 |
| 44-A2 | 0.63 | 3.16 | | | 0.75 |
| 45-A1 | 0.62 | 3.26 | | | 0.59 |
| 45-A2 | 0.62 | 3.27 | | | 0.56 |
| 45-A3 | 0.62 | 3.23 | | | 0.89 |
| 45-A4 | 0.62 | 3.23 | | | 0.40 |
| 45-A5 | 0.62 | 3.20 | | | 0.52 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 24

Thiazolium: 3-(3-iodopropyl)thiazol-3-ium

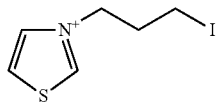

The titled compound was prepared using same procedure described above. Thiazole (4 g, 0.047 mol) and diiodopropane (27.2 mL, 0.24 mol) were refluxed in acetonitrile (15 mL) for 5 hours, then stirring was continued at room temperature overnight. The white precipitate was removed by filtration. To the filtrate was added diethyl ether 100 mL. The mixture was cooled in refrigerator overnight. The solid was filtered and washed with acetonitrile (20 mL) then ether (3×30 mL). After drying under reduced pressure, 17 g (95%) of desired product was obtained as a yellow solid. MS m/e (MH$^+$), calculated 253.95. found 254.0. $^1$H NMR confirmed the structure.

Example 25

$C_3$ Methyl Thiazolium:
3-(3-iodopropyl)-2-methylthiazol-3-ium

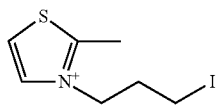

To a solution of 2-methylthiazole (3.0 g, 0.03 mol) in acetonitrile (15 mL) was added diiodopropane (17.4 mL, 0.15 mol). The reaction was refluxed for 5 hours, then stirring was continued at room temperature overnight. White precipitate was removed by filtration. To the filtrate was added diethyl ether (100 mL). White crystals formed. The mixture was cooled in refrigerator overnight. The solid was filtered and washed with acetonitrile (20 mL) then ether (3×30 mL). After drying under reduced pressure, 8.41 g product was obtained as a white solid (71%). MS m/e (MH$^+$), calculated 267.97. found 268.0. $^1$H NMR confirmed the structure.

Example 26

$C_3$ Benzthiazolium:
3-(3-bromopropyl)benzo[d]thiazol-3-ium

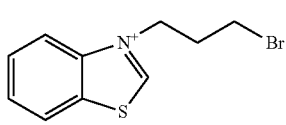 [SMILES: BrCCC[n+]1csc2ccccc21]

The titled compound was prepared using same procedure described above. Benzothiazole (22.5 mL, 0.2 mol) and 1,3-dibromopropane (102 mL, 1 mol) were refluxed for 48 hours to afford 35.5 g desired product as a yellow solid (69%). MS m/e (MH$^+$), calculated 257.98. found 258.0. $^1$HNMR confirmed the structure.

Example 27

$C_3$ Thiophenium ligand:
1-(3-iodopropyl)tetrahydro-1H-thiophenium

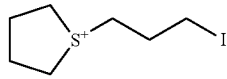

A mixture of tetrahydrothiophene (3.0 g, 0.034 mol) and diiodopropane (7.86 mL, 0.068 mol) in acetonitrile (3.4 mL) was stirred at 65° C. overnight. The solid was filtered and washed with acetonitrile (3×10 mL). After drying under high vacuum, the desired product was obtained as a white solid (6.13 g, 47%). MS m/e (MH$^+$), calculated 256.99. found 257.0. $^1$H NMR confirmed the structure.

Example 28

$C_{10}$ Pyridinium ligand: Synthesis of
1-bromodecyl-N-pyridinium bromide

To a vigorously stirring flask of 1,10-dibromodecane (337.2 mL; 1.5 mmol) was added pyridine in acetone (50 vol. %; 16.2 mL; 0.1 mmol) dropwise over 5 hours at 30° C. After the addition was complete, the mixture was heated to 45° C. for 18 hours. The reaction mixture was allowed to cool slightly and the resulting white precipitate was filtered over a Buchner funnel. The product was washed thoroughly with hexanes (3×100 mL) and vacuum dried. The product was identified by $^1$H NMR and mass spectrometry.

Example 29

Synthesis of Bis imiazole-n-alkane ligand

A solution of Na-imidazole (0.1 mol) (imidazole sodium derivative, Aldrich 197637, CAS 5587-42-8) in 100 mL THF. An appropriate amount of the dialkyl bromide was added and the mixture was stirred overnight at room temperature. The solids were filtered off and the filtrate was dried under vacuum. The product was purified by column chromatography using 500 g of silica and ethyl acetate. The resulting yield was 50-80%. The product was identified by $^1$H NMR and mass spectrometry.

Example 30

$C_3$ methyl imidazole ligand: Synthesis of
1-methyl-3-(1-bromopropyl) imidazolium bromide
ligand Dibromoalkane (0.3 mol) was placed into a 3-necked flask that was fitted with an overhead stirrer. Acetone was added such that the resulting solution was 3 M. Methyl imidazole (0.03 mol) was dissolved in acetone to result in a 2M solution. This was added to the flask and the reaction was stirred overnight at 45-50° C. The next day, the acetone was vacuumed off and the product was purified by column chromatography using 500 g of silica gel and 90:10 CH$_2$Cl$_2$: MeOH. The yield was in the range of 60-70% of materials

Example 31

Synthesis of 1-alkyl methyl pyrrolidine ligand

Dibromoalkane (0.3 mol) was placed into a 3-necked flask that was fitted with an overhead stirrer. Acetone was added such that the resulting solution was 3M. A 1-methylpyrrolidine solution (0.03 mol) was dissolved in acetone to result in a 2M solution. This was added to the flask and the reaction was stirred overnight at 55° C. The isolation method depended on the form of the product, for example, when the product precipitated out of solution, the solid was filtered and washed with acetone and when the product was an oil, the acetone was vacuumed off and the product was purified either by column chromatography using 500 g of silica gel and $CH_2Cl_2$:MeOH. The yield was in the range of 60-70% of materials that ranged from a clear oil to a white sold. The product was identified by $^1$H NMR and mass spectrometry.

Example 32

Synthesis of polymer modified with 1,3-dialkylimidazolium bromide ligand

The desired polyamine scaffold gel was dissolved in water and neutralized with an equimolar solution of NaOH. An appropriate amount of a solution of 1,3-dialkylimidazolium bromide in methanol was added to the polyamine solution. The mixture was heated to 75° C. for 24 hours. After cooling to room temperature the modified polyamine gel was washed by exposing the gel to a methanol wash (2×), 0.5 M HCl wash and water wash (2×). In each wash, the gel was stirred for 30 minutes, exposed to the washing solvent, and centrifuged; the supernatant liquid was decanted and the wash solvent was added to the gel. After the final water wash, the gel was placed into a lyophilizer to remove the water. The gel was isolated as a white fluffy material.

Example 33

Amphiphilic ligand: N-(2-(5-chloropentanamido) ethyl)-4-(nonyloxy)benzamide ligand

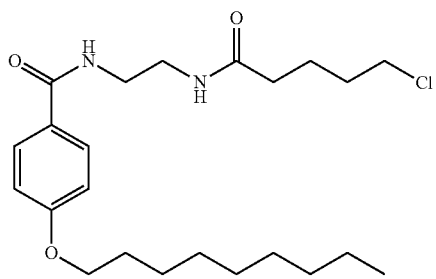 [SMILES: CCCCCCCCCOc1ccc(C(=O)NCCNC(=O)CCCCCl)cc1]

Step A: 1. 4-(nonyloxy)benzoyl chloride. To a suspension of 4-(nonyloxy)benzoic acid (6.02 g, 0.0228 mol) in 100 mL of dichloromethane was added DMF (0.176 mL, 0.00228 mol), followed by thionyl chloride (2.5 mL, 0.0342 mol). The reaction was stirred at room temperature for 2 hours and became a clear solution. The solvent was removed under reduced pressure. The residue was dried under high vacuum overnight. The product (6.54 gram) was obtained as a brown oil which was used for next step directly.

Step B: tert-butyl 2-(4-(nonyloxy)benzamido)ethylcarbamate. A solution of tert-butyl-2-aminoethylcarbamate (3.65 g, 0.0228 mol) and diisopropylethylamine (4.76 mL, 0.0274 mol) in 100 mL of dichloromethane was cooled to 4° C. in an ice bath. 4-(Nonyloxy)benzoyl chloride (6.54 g, 0.0228 mol) was dissolved in 50 mL of dichloromethane and was added to tert-butyl-2-aminoethylcarbamate solution dropwise. The internal temperature remained at or below 4° C. during the addition. After the addition, the reaction was warmed to room temperature and stirred for 2 hours. The mixture was washed with 1N HCl (2×150 mL), brine (150 mL), saturated $NaHCO_3$ solution (150 mL), and brine (150 mL). Organic phase was dried over $MgSO_4$ and concentrated. The crude product was passed through a silica gel plug (15% methanol in dichloromethane). The pure product (9.1 gram) was obtained as a white solid (98%).

Step C: tert-butyl 2-(4-(nonyloxy)benzamido)ethylcarbamate. To a solution of tert-butyl-2-(4-(nonyloxy)benzamido)ethylcarbamate (9.1 g, 0.0224 mol) in 100 mL of dichloromethane was added trifluoroacetic acid (17.25 mL, 0.224 mol). The reaction was stirred at room temperature for 16 hours. Solvent was removed under reduced pressure. Toluene (100 mL) was added to the residue to form a heteroazeotrope. Solvent and remaining trifluoroacetic acid were removed under reduced pressure. The residue was dried under high vacuum until no further weight change (2 days). The product was obtained as a trifluoroacetate salt, which was used directly for next step.

Step D: N-(2-(5-chloropentanamido)ethyl)-4-(nonyloxy) benzamide. A solution of tert-butyl-2-(4-(nonyloxy)benzamido)ethylcarbamate trifluoroacetate salt from previous step and diisopropylethylamine (11.7 mL, 0.0672 mol) in 150 mL of dichloromethane was cooled to 4° C. in an ice bath. 5-Chloro-valeroyl chloride (2.88 mL, 0.0224 mol) was dissolved in 50 mL of dichloromethane and was added to the above solution dropwise. The internal temperature remained at or below 4° C. during the addition. After the addition, the reaction was warmed to room temperature and stirred for 2 hours. It was then taken up with 150 mL of dichloromethane. The mixture was washed with 1N HCl (2×300 mL), brine (300 mL), saturated $NaHCO_3$ solution (300 mL), and brine (300 mL). Organic phase was dried over $MgSO_4$ and concentrated. The crude product was recrystallized in acetonitrile to give pure N-(2-(5-chloropentanamido)ethyl)-4-(nonyloxy)benzamide as a white solid (9.36 g, 98%). MS (EI) m/e (MNa$^+$), calculated (for $C_{23}H_{37}ClN_2O_3Na^+$) 447.24. found 447.21.

Example 34

Tryptamine ligand: N-(2-(1H-indol-3-yl)ethyl)-5-chloropentanamide

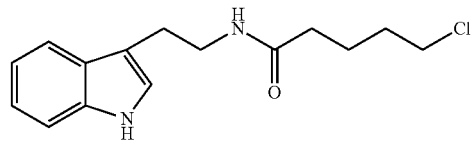 [SMILES: O=C(CCCCCl)NCCc1c[nH]c2ccccc12]

A solution of 2-(1H-indol-3-yl)ethanamine (5.10 g, 0.032 mol) and diisopropylethyl amine (7.23 mL, 0.042 mol) in 100 mL of dichloromethane was cooled to 4° C. in ice bath.

5-Chloro-valeroyl chloride (4.2 mL, 0.32 mol) was dissolved in 50 mL of dichloromethane and was added to the solution of 2-(1H-indol-3-yl)ethanamine dropwise. The internal temperature remained at or below 4° C. during the addition. After the addition, the reaction was warmed to room temperature and stirred for 2 hours. The mixture was washed with 1N HCl (2×150 mL), brine (150 mL), saturated NaHCO$_3$ solution (150 mL), and brine (150 mL). The organic phase was dried over MgSO$_4$ and concentrated. The crude product was purified by flash chromatography (silica gel, 15% methanol in dichloromethane). Pure product (7.9 gram) was obtained as a yellow solid (89%). MS m/e (MH$^+$), calculated 279.13. found 279.16. This synthesis can be used to make other amino acid-based ligands by substituting the appropriate amine reactant for 2-(1H-indol-3-yl)ethanamine (e.g., use of 3-methylbutan-1-amine to make a Leu-based ligand).

Example 35

DMP 504 Comparative Example

Dibromodecane (12.10 g, 0.039 mol) was dispensed with methanol (13 mL) and N,N-dimethylformamide (13 mL) into a round bottom flask (100 mL) under nitrogen with a mechanical stirrer and reflux condenser. Diaminohexane (4.55 g, 0.039 mol) was added to the flask and the mixture was brought to reflux while stirring. After 35 minutes gelation occurred and mechanical stirring was stopped. The resulting gel was cured at 85° C. for 17 hours. The polymer formed was swollen and ground in water (two times, 80 mL), methanol (two times, 80 mL), water (two times, 80 mL), ethanol (once, 500 mL), water (once, 100 mL), HCl (1M, 80 mL) ethanol (500 mL) and water (100 mL) and lyophilized until dry.

| Sample # | Bile acid binding affinity A assay (mmol/g) | Bile acid binding capacity B assay (mmol/g) | Bile acid binding retention (mmol/g) | Hamster |
|---|---|---|---|---|
| 46-A1 | 0.52 | 2.60 | 6.22 | 4.6 |

Example 36

N,N,N',N'-Tetrakis(3-aminopropyl)-1,12-diaminododecane (C$_{12}$ BTA), N,N,N',N'-Tetrakis(3-aminopropyl)-1,10-diaminodecane (C$_{10}$ BTA), N,N,N',N'-Tetrakis(3-aminopropyl)-1,8-diaminooctane (C$_8$ BTA), N,N,N',N'-Tetrakis(3-aminopropyl)-1,4-diaminobutane (C$_4$ BTA) beads synthesis with 1,3-dichloropropanol (DCP)

The synthesis of C$_{12}$ BTA-DCP, C$_{10}$ BTA-DCP, C$_8$ BTA-DCP, C$_4$ BTA-DCP beads were conducted in a Semi-Continuous Parallel Polymerization Reactor (SCPPR). C$_4$ BTA, C$_8$ BTA, C$_{10}$ BTA, and C$_{12}$ BTA monomers were dispensed into 11 mL glass tubes and cooled to 5° C. in an ice bath and water was added. Hydrochloric acid (HCl, 37 wt. % in water) was added slowly to this solution followed by mixing for 2 minutes. Dodecylbenzenesulfonic acid sodium salt (DDS) (molecular weight (MW) 348.48, 15 wt. % in water) and the crosslinker 1,3-dichloropropanol (DCP) (MW 128.99) were added to the solution followed by mixing for 5 minutes. The organic layer of heptanes and Span 80 (MW 428.60, 15 wt. % in heptanes) was then added to the aqueous solution. The test tubes were loaded into the SCPPR, sealed, and pressurized to 70 pounds/square inch (psi) (4.83×10$^5$ Pa). The reaction was allowed to react at 75° C. with stirring (400 rpm) for 17 hours. The resulting solid polymer beads were then swollen in ethanol, washed with (1) aqueous HCl (1 M), (2) water, (3) NaOH (1M), (4) water (3×) and lyophilized until dry. Various synthesis experiments are detailed in the table below.

| | Aqueous Layer | | | | | Organic layer | | |
|---|---|---|---|---|---|---|---|---|
| | Monomer | Solvent | Acid | Surfactant | Crosslinker | solvent | Surfactant | |
| Sample # | BTA Core | BTA wt. (mg) | water (mg) | HCl (mg) | DDS (mg) | DCP (mg) | heptanes (Mg) | span 80 (mg) | Polymer Product |
| 47-A1 | C$_{10}$ | 400 | 949.2 | 0.0 | 6.8 | 218.9 | 1947.7 | 155.8 | Beads |
| 47-A2 | C$_{10}$ | 400 | 965.5 | 0.0 | 13.8 | 218.9 | 1981.2 | 158.5 | Beads |
| 47-A3 | C$_{10}$ | 400 | 982.5 | 0.0 | 21.1 | 218.9 | 2016.0 | 161.3 | Beads |
| 47-A4 | C$_{10}$ | 400 | 1000.0 | 0.0 | 28.6 | 218.9 | 2052.0 | 164.2 | Gel |
| 47-A5 | C$_{10}$ | 400 | 1035.6 | 36.4 | 7.4 | 218.9 | 2125.1 | 170.0 | Beads |
| 47-A6 | C$_{10}$ | 400 | 1053.5 | 36.4 | 15.0 | 218.9 | 2161.7 | 172.9 | Beads |
| 47-B1 | C$_{10}$ | 400 | 1071.9 | 36.4 | 23.0 | 218.9 | 2199.6 | 176.0 | Beads |
| 47-B2 | C$_{10}$ | 400 | 1091.1 | 36.4 | 31.2 | 218.9 | 2238.9 | 179.1 | Beads |
| 47-B3 | C$_{10}$ | 400 | 1363.9 | 36.4 | 18.2 | 218.9 | 2798.6 | 223.9 | Gel |
| 47-B4 | C$_{10}$ | 400 | 1053.5 | 36.4 | 15.0 | 218.9 | 2161.7 | 172.9 | Beads |
| 47-B5 | C$_{10}$ | 400 | 834.4 | 36.4 | 12.8 | 218.9 | 1712.1 | 137.0 | Beads |
| 47-B6 | C$_{10}$ | 400 | 671.4 | 36.4 | 11.2 | 218.9 | 1377.8 | 110.2 | Gel |
| 47-C1 | C$_{10}$ | 400 | 1122.1 | 72.9 | 8.0 | 218.9 | 2302.5 | 184.2 | Beads |
| 47-C2 | C$_{10}$ | 400 | 1141.4 | 72.9 | 16.3 | 218.9 | 2342.2 | 187.4 | Gel |
| 47-C3 | C$_{10}$ | 400 | 1161.4 | 72.9 | 24.9 | 218.9 | 2383.2 | 190.7 | Beads |
| 47-C4 | C$_{10}$ | 400 | 1182.2 | 72.9 | 33.8 | 218.9 | 2425.8 | 194.1 | Beads |
| 48-A1 | C$_{12}$ | 400 | 1047.7 | 34.1 | 15.0 | 120.3 | 2149.9 | 172.0 | Beads |
| 48-A2 | C$_{12}$ | 400 | 1047.7 | 34.1 | 15.0 | 180.5 | 2149.9 | 172.0 | Beads |
| 48-A3 | C$_{12}$ | 400 | 1047.7 | 34.1 | 15.0 | 240.7 | 2149.9 | 172.0 | Beads |
| 48-A4 | C$_{12}$ | 400 | 1047.7 | 34.1 | 15.0 | 300.9 | 2149.9 | 172.0 | Beads |
| 48-A5 | C$_{12}$ | 400 | 1047.7 | 34.1 | 15.0 | 204.6 | 2149.9 | 172.0 | Beads |
| 48-A6 | C$_{12}$ | 400 | 1047.7 | 34.1 | 15.0 | 204.6 | 2149.9 | 172.0 | Beads |
| 48-B1 | C$_{12}$ | 400 | 1047.7 | 34.1 | 15.0 | 204.6 | 2149.9 | 172.0 | Beads |
| 48-B2 | C$_{12}$ | 400 | 1047.7 | 34.1 | 15.0 | 204.6 | 2149.9 | 172.0 | Gel |
| 48-B3 | C$_{12}$ | 400 | 949.2 | 0.0 | 6.8 | 204.6 | 1947.7 | 155.8 | Gel |

-continued

| | | Aqueous Layer | | | | Organic layer | | |
|---|---|---|---|---|---|---|---|---|
| | Monomer | Solvent | Acid | Sur-factant | Cross-linker | solvent | Sur-factant | |
| Sample # | BTA Core | BTA wt. (mg) | water (mg) | HCl (mg) | DDS (mg) | DCP (mg) | heptanes (Mg) | span 80 (mg) | Polymer Product |
| 48-B4 | $C_{12}$ | 400 | 965.5 | 0.0 | 13.8 | 204.6 | 1981.2 | 158.5 | Gel |
| 48-B5 | $C_{12}$ | 400 | 982.5 | 0.0 | 21.1 | 204.6 | 2016.0 | 161.3 | Gel |
| 48-B6 | $C_{12}$ | 400 | 1000.0 | 0.0 | 28.6 | 204.6 | 2052.0 | 164.2 | Beads |
| 48-C1 | $C_{12}$ | 400 | 1030.0 | 34.1 | 7.4 | 204.6 | 2113.5 | 169.1 | Beads |
| 48-C2 | $C_{12}$ | 400 | 1047.7 | 34.1 | 15.0 | 204.6 | 2149.9 | 172.0 | Beads |
| 48-C3 | $C_{12}$ | 400 | 1066.1 | 34.1 | 22.8 | 204.6 | 2187.6 | 175.0 | Gel |
| 48-C4 | $C_{12}$ | 400 | 1085.1 | 34.1 | 31.0 | 204.6 | 2226.7 | 178.1 | Gel |
| 48-C5 | $C_{12}$ | 400 | 1047.7 | 34.1 | 15.0 | 204.6 | 2149.9 | 10.7 | Gel |
| 48-C6 | $C_{12}$ | 400 | 1047.7 | 34.1 | 15.0 | 204.6 | 2149.9 | 50.2 | Gel |
| 48-D1 | $C_{12}$ | 400 | 1047.7 | 34.1 | 15.0 | 204.6 | 2149.9 | 89.6 | Beads |
| 48-D2 | $C_{12}$ | 400 | 1047.7 | 34.1 | 15.0 | 204.6 | 2149.9 | 129.0 | Beads |
| 48-D3 | $C_{12}$ | 400 | 1110.8 | 68.1 | 7.9 | 204.6 | 2279.3 | 182.3 | Beads |
| 48-D4 | $C_{12}$ | 400 | 1129.9 | 68.1 | 16.1 | 204.6 | 2318.6 | 185.5 | Beads |
| 48-D5 | $C_{12}$ | 400 | 1149.7 | 68.1 | 24.6 | 204.6 | 2359.3 | 188.7 | Beads |
| 48-D6 | $C_{12}$ | 400 | 1170.3 | 68.1 | 33.4 | 2401.4 | 192.1 | 204.6 | Gel |
| 49-A1 | $C_4$ | 400 | 1076.9 | 46.1 | 15.4 | 277.1 | 2209.7 | 176.8 | gel/beads |
| 49-A2 | $C_4$ | 400 | 1128.7 | 46.1 | 37.6 | 277.1 | 2316.2 | 185.3 | gel/beads |
| 49-A3 | $C_4$ | 400 | 1185.9 | 46.1 | 62.1 | 277.1 | 2433.5 | 194.7 | Beads |
| 49-A4 | $C_4$ | 400 | 1249.1 | 46.1 | 89.2 | 277.1 | 2563.2 | 205.1 | Beads |

Example 37

$C_{12}$ BTA-DCP, $C_{10}$ BTA-DCP, $C_8$ BTA-DCP, $C_4$ BTA-DCP Beads Synthesis for In Vivo Study A 250 mL 3-neck round bottom flask equipped with overhead stirrer, condenser, and thermometer was charged with $C_{12}$ BTA (5.0 g, 11.66 mmol) and water (11.39 mL). The resulting mixture was stirred in an ice bath for 5 minutes. Hydrochloric acid (1.15 ml, 11.66 mmol, 37 wt. % in water) was added slowly over a 2 minute period. The mixture was stirred for an extra 2 minutes in the ice bath before removing it. DDS (1.24 mL, 15 wt. % in water) was then added to the above mixture and stirred for 2 minutes. 1,3-Dichloro-2-propanol (2.56 g, 19.83 mmol) was added. Heptanes (21.59 mL) and Span 80 solution (20.32 mL, 15 wt. % in heptanes) were then added. The final mixture was stirred at 220 rpm with an overhead stirrer and heated in oil bath at 75° C. The internal temperature of the reaction was at 70° C. After 3 hours, a Dean-Stark treatment was performed to remove the water using the azeotrope of heptanes and water (at 80° C.). The reaction was ended after the mixture temperature reached 100° C. or when all the water in the reaction mixture was collected.

The reaction mixture was cooled to ambient temperature, stirring was stopped, and the organic layer was decanted. The beads were washed with 150 mL isopropyl alcohol, followed by one wash with HCl (150 ml, 1.0 M), one wash with water, two washes with $NH_4OH$ (150 mL, 10 wt. % in water), one wash saturated aqueous NaCl solution, and three washes with water. The beads were lyophilized for 48 hours. The final product was isolated in 80% yield (4.9 g). Various synthesis experiments are detailed below.

Acid loading of sample 51-D1. The isolated dry bead prepared from 51-D1 (example 37) was placed into a flask. Using 1 M HCl solution in water, an appropriate amount of HCl was added to the bead such that the resulting beads contained 5, 10, 15 and 20 weight percent of chloride. The chloride content in the bead was later confirmed by elemental analysis and found to be 5, 9, 12, and 19 wt. % respectively. The sample ID's for these compounds were given 79-A1, 79-A2, 79-A3 and 79-A4 respectively.

| | | Aqueous Layer | | | | Organic layer | | |
|---|---|---|---|---|---|---|---|---|
| | Monomer | Solvent | Acid | Sur-factant | Cross-linker | solvent | Sur-factant | |
| Sample # | BTA Core | BTA wt (mg) | water (mg) | HCl (mg) | DDS (mg) | DCP (mg) | heptanes (Mg) | span 80 (mg) | Polymer Product |
| 50-A1 | $C_{12}$ | 1600 | 4191 | 136 | 60 | 818 | 8600 | 688 | beads |
| 50-A2 | $C_{12}$ | 1600 | 4599 | 272 | 99 | 818 | 9437 | 755 | beads |
| 51-A1 | $C_4$ | 2000 | 5678 | 231 | 203 | 1385 | 11651 | 932 | beads |
| 51-B1 | $C_8$ | 2000 | 5300 | 196 | 76 | 1177 | 10877 | 870 | beads |
| 51-C1 | $C_{10}$ | 2000 | 5267 | 182 | 75 | 1094 | 10808 | 865 | beads |
| 51-D1 | $C_{12}$ | 2000 | 5239 | 170 | 75 | 1023 | 10750 | 860 | beads |
| 52-A1 | $C_8$ | 7460 | 19770 | 731 | 282 | 4390 | 40568 | 3245 | beads |
| 53-A1 | $C_{12}$ | 8250 | 21609 | 702 | 309 | 4219 | 44342 | 3547 | beads |

-continued

| | | Aqueous Layer | | | | | Organic layer | | |
|---|---|---|---|---|---|---|---|---|---|
| | | Monomer | Solvent | Acid | Surfactant | Crosslinker | solvent | Surfactant | |
| Sample # | BTA Core | BTA wt (mg) | water (mg) | HCl (mg) | DDS (mg) | DCP (mg) | heptanes (Mg) | span 80 (mg) | Polymer Product |
| 54-A1 | $C_{12}$ | 4312 | 11294 | 367 | 161 | 1427 | 23176 | 1854 | beads |
| 55-A1 | $C_{12}$ | 5000 | 13096 | 425 | 187 | 2106 | 26874 | 2150 | beads |
| 56-A1 | $C_{12}$ | 4312 | 11294 | 367 | 161 | 2595 | 23176 | 1854 | beads |
| 57-A1 | $C_{12}$ | 25000 | 65482 | 2128 | 935 | 12786 | 134369 | 10750 | beads |
| 58-A1 | $C_{12}$ | 5000 | 13096 | 426 | 187 | 3761 | 26874 | 2150 | beads |
| 59-A1 | $C_4$ | 5000 | 14731 | 577 | 737 | 3464 | 30227 | 2418 | beads |
| 60-A1 | $C_{12}$ | 10000 | 26193 | 851 | 374 | 5115 | 53748 | 4300 | beads |
| 61-A1 | $C_{12}$ | 5000 | 13096 | 426 | 187 | 2557 | 26874 | 2150 | beads |
| 62-A1 | $C_{12}$ | 5000 | 13096 | 426 | 187 | 2557 | 26874 | 2150 | beads |
| 63-A1 | $C_{12}$ | 4312 | 11294 | 367 | 161 | 1427 | 23176 | 1854 | beads |
| 64-A1 | $C_{12}$ | 5000 | 13096 | 425 | 187 | 2106 | 26874 | 2150 | beads |
| 65-Al | $C_{12}$ | 4312 | 11294 | 367 | 161 | 2595 | 23176 | 1854 | beads |
| 66-A1 | $C_{12}$ | 10000 | 26193 | 851 | 374 | 5115 | 53748 | 4300 | beads |
| 67-A1 | $C_{12}$ | 5000 | 13096 | 426 | 187 | 1956 | 26874 | 2150 | beads |
| 68-A1 | $C_{12}$ | 5000 | 13096 | 426 | 187 | 2256 | 26874 | 2150 | beads |
| 69-A1 | $C_{12}$ | 5000 | 13096 | 426 | 187 | 2407 | 26874 | 2150 | beads |
| 70-A1 | $C_{12}$ | 25000 | 65480 | 2125 | 935 | 10530 | 134370 | 10750 | beads |
| 80-A1 | $C_{12}$ | 5000 | 13096 | 425 | 187 | 2557 | 26874 | 2150 | beads |
| 81-A2 | $C_{12}$ | 5000 | 13096 | 425 | 187 | 2106 | 26874 | 2150 | beads |

Bile acid binding capacity, affinity, and retention for each resulting polymer were determined via the A assay, B assay and hamster model and results are reported in the table below.

| Library | BTA Core | BA binding capacity B Assay Data (mmol/g) | BA binding affinity A Assay Data (mmol/g) | BA binding retention Hamster (mmol/g) | % Primary Bile Acid in feces | Phosphate binding B Assay Data (mmol/g) | Swelling (g/g) | Tackiness* |
|---|---|---|---|---|---|---|---|---|
| 50-A1 | $C_{12}$ | 3.34 | 0.64 | 0.50 | 10.9 | | 0.65 | 2 |
| 50-A2 | $C_{12}$ | 3.33 | 0.64 | 0.43 | 12.8 | | 0.97 | 2 |
| 51-A1 | $C_4$ | 3.19 | 0.37 | 0.15 | 10.5 | | 5.98 | 0 |
| 51-B1 | $C_8$ | 3.28 | 0.45 | 0.33 | 3.5 | | 0.99 | 0 |
| 51-C1 | $C_{10}$ | 3.26 | 0.54 | 0.40 | 5.7 | | 0.27 | 1 |
| 51-D1 | $C_{12}$ | 3.32 | 0.64 | 0.34 | 8.5 | | 0.38 | 2 |
| 52-A1 | $C_8$ | 3.24 | 0.46 | 0.24 | 2.5 | 0.26 | 1.15 | 0 |
| 53-A1 | $C_{12}$ | 3.18 | 0.66 | 0.36 | 6.5 | | 0.69 | 2 |
| 54-A1 | $C_{12}$ | 3.25 | 0.65 | 0.35 | 14.8 | | 2.16 | 2 |
| 55-A1 | $C_{12}$ | 3.27 | 0.67 | 0.52 | 17.3 | 0.23 | 0.39 | 2 |
| 56-A1 | $C_{12}$ | 3.01 | 0.66 | 0.34 | 20.4 | 0.08, 0.10 | 0.82 | 0 |
| 57-A1 | $C_{12}$ | 3.03 | 0.67 | 0.38 | 18.8, 16.4 | 0.07 | 0.41 | 1 |
| 58-A1 | $C_{12}$ | 2.87 | 0.67 | 0.32 | 25.9 | 0.07 | 0.50 | 0 |
| 59-A1 | | 3.17 | 0.39 | | | 0.61 | 3.09 | |
| 79-A1 | $C_{12}$ | 2.99 | 0.66 | 0.55 | 18.6 | | 0.64 | 0 |
| 79-A2 | $C_{12}$ | 2.95 | 0.65 | 0.54 | 17.3 | | 0.64 | 0 |
| 79-A3 | $C_{12}$ | 2.85 | 0.62 | 0.51 | 14.3 | | 0.64 | 0 |
| 79-A4 | $C_{12}$ | 2.74 | 0.64 | | | | 0.64 | 0 |
| 60-A1 | $C_{12}$ | 3.08 | 0.67 | 0.41 | 11.6 | | 0.60 | 0 |
| 61-A1 | $C_{12}$ | 3.16 | 0.64 | | 12.7 | | 1.08 | 0 |
| 62-A1 | $C_{12}$ | 3.15 | 0.66 | | | | 0.26 | 0 |
| 63-A1 | $C_{12}$ | 3.30 | 0.63 | | | | 3.00 | 2 |
| 64-A1 | $C_{12}$ | 3.20 | 0.66 | | | | 1.30 | 1 |
| 65-A1 | $C_{12}$ | 2.83 | 0.66 | | | | 0.41 | 1 |
| 66-A1 | $C_{12}$ | 2.98 | 0.67 | | | | 0.50 | 1 |
| 67-A1 | $C_{12}$ | 3.13 | 0.65 | | | | 0.73 | 2 |
| 68-A1 | $C_{12}$ | 2.99 | 0.66 | | | | 0.37 | 2 |
| 69-A1 | $C_{12}$ | 3.15 | 0.66 | | | | 0.41 | 1 |
| 70-A1 | $C_{12}$ | | 0.65 | | | | | 2 |
| 80-A1 | $C_{12}$ | 3.12 | 0.66 | | | 0.15 | 0.65 | 22 |
| 81-A2 | $C_{12}$ | 3.14 | 0.66 | | | 0.20 | 0.97 | 2 |

*tackiness number 0 = free flowing beads, 1 = slightly soft beads, 2 = slightly sticky beads, 3 = sticky and soft

Example 38

$C_{12}$ BTA, $C_{10}$ BTA, $C_8$ BTA, $C_4$ BTA beads synthesis with 1,1'-(dodecane-1,12-diyl)bis(3-bromopropyl)-1H-imidazol-3-ium ($C_{12}$ core, $C_3$ bisimidazolium) crosslinker The synthesis of $C_{12}$ BTA-$C_{12}$ core, $C_3$ bisimidazolium, $C_{10}$ BTA-$C_{12}$ core, $C_3$ bisimidazolium, and $C_4$ BTA-$C_{12}$ core, $C_3$ bisimidazolium beads were conducted in a SCPPR. $C_4$ BTA, $C_8$ BTA, $C_{10}$ BTA, and $C_{12}$ BTA monomers were dispensed into 11 mL glass tubes and cooled to 5° C. in an ice bath and water was added. Hydrochloric acid (HCl, 37 wt. % in water) was added slowly to this solution followed by mixing for 2 minutes. DDS (15 wt. % in water) and a solution of the designated crosslinking monomer (40 wt. % in water) of formula X—$R_1$—X (wherein X is halo such as chloro or bromo and $R_1$ is $C_{12}$ core/$C_3$ bisimidazolium) were added. This solution was mixed for 5 minutes and the organic layer of heptanes and Span 80 (15 wt. % in heptanes) was added to the aqueous layer. The test tubes were loaded into the SCPPR, sealed, and pressurized to 70 psi. The reaction was run at 75° C. with stirring (400 rpm) for 17 hours. The solid polymer beads were then swollen in ethanol, washed with aqueous HCl (1 M), water (3×) and lyophilized until dry. Various synthesis experiments are detailed in the table below.

Example 39

$C_{12}$ BTA-$C_{12}$ Core, $C_3$ Bisimidazolium and $C_4$ BTA-$C_{12}$ Core, $C_3$ Bisimidazolium Beads for In Vivo Study A 500 mL 3-neck round bottom flask equipped with overhead stirrer, condenser, and thermometer was charged with $C_{12}$ BTA (5.0 g 11.66 mmol) and 5.67 mL water. The resulting mixture was stirred in an ice bath for 5 minutes. Hydrochloric acid (1.15 mL, 11.66 mmol, 37 wt. % in water) was added slowly over a two minute period. The mixture was stirred for an extra two minutes in the ice bath before removal. DDS (9.83 mL, 15 wt. % in water) was then added to the above mixture and stirred for two minutes. An organic phase of the crosslinking monomer (32.94 mL, 18.66 mmol, 40 wt. % in water) of formula X—$R_1$—X (wherein X is halo such as chloro or bromo and $R_1$ is $C_{12}$ core, $C_3$ bisimidazolium), heptanes (82.74 mL), and Span 80 solution (77.82 ml, 15 wt. % in heptanes) was added to the mixture. The final mixture was stirred at 220 rpm with an overhead stirrer and heated in oil bath at 75° C. The internal temperature of the reaction was at 70° C. After 3 hours, a Dean-Stark treatment was performed to remove the water using the azeotrope of heptanes and water at 80° C. This was achieved by increasing the temperature of the oil bath. The endpoint of the

| | Monomer | | Aqueous Layer | | | Crosslinker $C_{12}$ | Organic layer | | |
|---|---|---|---|---|---|---|---|---|---|
| Sample # | BTA Core | BTA wt (mg) | Solvent water (mg) | Acid HCl (mg) | Surfactant DDS (mg) | core/$C_3$ bisimidazolium (mg) | solvent heptanes (mg) | Surfactant span 80 (mg) | Polymer Product |
| 71-A1 | $C_4$ | 100 | 867 | 12 | 37 | 357 | 2600 | 208 | Gel |
| 71-A2 | $C_4$ | 100 | 867 | 12 | 37 | 357 | 2600 | 208 | Gel |
| 71-A3 | $C_4$ | 100 | 867 | 12 | 37 | 357 | 2600 | 208 | Gel |
| 71-A4 | $C_4$ | 100 | 867 | 12 | 37 | 357 | 2600 | 208 | Gel |
| 71-B1 | $C_4$ | 100 | 867 | 12 | 37 | 357 | 2600 | 208 | Gel |
| 71-B2 | $C_4$ | 100 | 867 | 12 | 37 | 357 | 2600 | 208 | Gel |
| 71-B3 | $C_4$ | 100 | 867 | 12 | 37 | 357 | 2600 | 208 | Gel |
| 71-B4 | $C_4$ | 100 | 867 | 12 | 37 | 357 | 2600 | 208 | Gel |
| 71-C1 | $C_4$ | 100 | 867 | 12 | 37 | 357 | 2600 | 208 | Gel |
| 71-C2 | $C_4$ | 100 | 995 | 12 | 42 | 424 | 2986 | 239 | Gel |
| 71-C3 | $C_4$ | 100 | 1124 | 12 | 48 | 491 | 3372 | 270 | Gel |
| 71-C4 | $C_4$ | 100 | 1253 | 12 | 53 | 558 | 3758 | 301 | Gel |
| 71-D1 | $C_4$ | 100 | 890 | 12 | 14 | 357 | 2670 | 214 | Gel |
| 71-D2 | $C_4$ | 100 | 872 | 12 | 32 | 357 | 2615 | 209 | Gel |
| 71-D3 | $C_4$ | 100 | 853 | 12 | 50 | 357 | 2560 | 205 | Beads |
| 71-D4 | $C_4$ | 100 | 835 | 12 | 69 | 357 | 2505 | 200 | Gel |
| 72-C1 | $C_{10}$ | 100 | 502 | 9 | 9 | 282 | 1507 | 15 | Gel |
| 72-C2 | $C_{10}$ | 100 | 619 | 9 | 10 | 282 | 1857 | 68 | Gel |
| 72-C3 | $C_{10}$ | 100 | 806 | 9 | 12 | 282 | 2419 | 153 | Gel |
| 72-C4 | $C_{10}$ | 100 | 1156 | 9 | 16 | 282 | 3468 | 312 | Gel |
| 72-D1 | $C_{10}$ | 100 | 960 | 9 | 0 | 282 | 2880 | 230 | Gel |
| 72-D2 | $C_{10}$ | 100 | 1057 | 9 | 40 | 282 | 3172 | 254 | Beads |
| 72-D3 | $C_{10}$ | 100 | 1177 | 9 | 88 | 282 | 3530 | 282 | Gel |
| 72-D4 | $C_{10}$ | 100 | 1326 | 9 | 149 | 282 | 3979 | 318 | Gel |
| 73-B1 | $C_{12}$ | 100 | 690 | 9 | 29 | 264 | 2071 | 166 | Beads |
| 73-B2 | $C_{12}$ | 100 | 690 | 9 | 29 | 264 | 2071 | 166 | Beads |
| 73-B3 | $C_{12}$ | 100 | 880 | 9 | 37 | 362 | 2640 | 211 | Beads |
| 73-B4 | $C_{12}$ | 100 | 880 | 9 | 37 | 362 | 2640 | 211 | Beads |
| 73-D1 | $C_{12}$ | 100 | 690 | 9 | 29 | 264 | 2071 | 166 | Beads |
| 73-D2 | $C_{12}$ | 100 | 690 | 9 | 29 | 264 | 2071 | 166 | Beads |
| 73-D3 | $C_{12}$ | 100 | 880 | 9 | 37 | 362 | 2640 | 211 | Beads |
| 73-D4 | $C_{12}$ | 100 | 880 | 9 | 37 | 362 | 2640 | 211 | Beads | process was when the temperature of the mixture reached 100° C. or when all the water in the reaction mixture was collected.

The reaction mixture was cooled to ambient temperature, stirring was stopped, and the organic layer was decanted. The beads were washed with 150 mL isopropyl alcohol, followed by one wash with HCl (150 mL, 1.0 M), one wash with water, one wash with saturated aqueous NaCl solution, and three washes with water. The beads were lyophilized for 48 hours. The final product was isolated in 80% yield (4.9 g).

|  | | Aqueous Layer | | | Organic layer | | | |
| --- | --- | --- | --- | --- | --- | --- | --- | --- |
| | | Monomer | | | Crosslinker | | | |
| Sample # | BTA Core | BTA wt (mg) | Solvent water (mg) | Acid HCl (mg) | Surfactant DDS (mg) | $C_{12}$ core, $C_3$ bisimidazolium (mg) | solvent heptanes (mg) | Surfactant span 80 (mg) | Polymer Product |
| 82-D3 | $C_4$ | 100 | 853 | 11.53 | 50.3 | 356 | 2560 | 204.8 | Bead |
| 74-A1 | $C_4$ | 2000 | 17069 | 231 | 1006 | 7139 | 51207 | 4097 | Beads |
| 75-A1 | $C_4$ | 3000 | 25603 | 346 | 1509 | 10709 | 76810 | 6145 | Beads |
| 76-A1 | $C_4$ | 6000 | 51207 | 692 | 3019 | 21418 | 153620 | 12290 | Beads |
| 77-A1 | $C_{12}$ | 3794 | 26189 | 323 | 1118 | 10000 | 78566 | 6285 | Beads |
| 77-A2 | $C_{12}$ | 3794 | 26189 | 323 | 1118 | 10000 | 78566 | 6285 | Beads |
| 78-A1 | $C_{12}$ | 5000 | 34510 | 426 | 1474 | 13177 | 103529 | 8282 | Beads |

Bile acid binding capacity, affinity, and retention for each resulting polymer were determined via the A assay, B assay and hamster model and results are reported in the table below.

| Sample # | BTA Core | B Assay (mmol/g) | A Assay (mmol/g) | In vivo binding (mmoles/g) | % Primary Bile Acid in feces | Swelling (g/g) | Tackiness | Ligand Grafted |
| --- | --- | --- | --- | --- | --- | --- | --- | --- |
| 77-A1 | $C_{12}$ | 2.74 | 0.62 | 0.49 | 9.6 | 32 | 0 | |
| 77-A2 | $C_{12}$ | 2.83 | 0.62 | 0.44 | 12.4 | 25 | 1 | |
| 75-A1 | $C_4$ | 3.06 | 0.54 | 0.34 | 3.7 | 25 | 1 | |

Example 40

Hydrophobic Post Polymerization of Beads Prepared with $C_4$ BTA and $C_{12}$ Core, $C_3$ Bisimidazolium Crosslinker for In Vivo Study Sample 82-D3, described in example 39 was repeated on a larger scale (3 g of BTA $C_4$ core was used) on the bench. The resultant beads were washed and described as above. To the resulting beads the following procedure was performed. N-methylpyrrolidone (NMP) was added to swell the $C_4$ BTA crosslinked $C_{12}$ core, $C_3$ bisimidazolium beads in 11 mL glass tubes. The hydrophobizing agent (either 1,12-dibromododecane or 1-bromodecane) was added and the glass tubes were fitted with overhead stirrers, sealed, and purged with nitrogen. The post polymerization reaction was allowed to proceed at 75° C. for 18 hours. After cooling, the beads were diluted with ethanol and purified by washing with ethanol (2×), 1M HCl (2×), and water (3×). The beads were dried by lyophilization overnight.

| Sample # | Beads | 1,12-dibromododecane (g) | 1-bromodecane (g) | N-methylpyrrolidone (mL) |
| --- | --- | --- | --- | --- |
| 83-A1 | 1.00 | 1.00 | | 4.50 |
| 83-A3 | 1.00 | 1.50 | | 5.70 |
| 84-A1 | 1.00 | | 1.00 | 4.50 |
| 84-A3 | 1.00 | | 1.50 | 5.70 |

Bile acid binding capacity, affinity, and retention for each resulting polymer were determined via the A assay, B assay and hamster model and results are reported in the table below.

| Sample # | B Assay (mmol/g) | A Assay (mmol/g) | Hamster in vivo binding (mmol/g) | % Primary Bile Acid in feces | Swelling (g/g) |
| --- | --- | --- | --- | --- | --- |
| 83-A1 | 2.94 | 0.60 | | | 10.1 |
| 83-A3 | 2.95 | 0.61 | 0.37 | 5.0 | 10.8 |
| 84-A1 | 2.99 | 0.61 | | | 47.4 |
| 84-A3 | 2.90 | 0.61 | | | 48.7 |

Example 41

Synthesis of $C_4$ BTA beads with TMBMP-DBD (4,4'-(propane-1,3-diyl)bis(1-(10-bromodecyl)-1-methylpiperidinium))

A 1 L reactor equipped with overhead stirrer, condenser and thermocouple was charged with $C_4$ BTA (7.24 g 22.9 mmol), water (56.0 mL), acetonitrile (27.2 mL), and DDS solution (23.9 mL, 15 wt. % in water). The mixture was stirred for 5 minutes. After a homogeneous solution was obtained, TMBMP-DBD (30.7 g, 36.6 mmol) was added. The resulting mixture was stirred for an extra 5 minutes before the addition of heptanes (182.9 mL) and Span 80 solution (172.0 mL, 15 wt. % in heptanes). The final mixture was stirred at 150 rpm with an overhead stirrer. The external oil was ramped to 75° C. in 1 hour. The internal temperature of the reaction was at 72-75° C. After 16 hours, a Dean-Stark treatment was performed to remove the acetonitrile and water at 80° C. This was achieved by increasing the temperature of the oil bath to 95° C. The end point of the process end point was when the temperature of the mixture reached 95° C. or when all the water in the reaction mixture was collected.

The reaction mixture was cooled to ambient temperature, stirring was stopped, and the organic layer was removed by vacuum. The beads were washed with 500 mL ethanol twice and collected by filtration. The beads were vacuum dried for 24 hours before the post polymerization. The final product was isolated in a 67% yield (25 g).

Post polymerization, a further reaction with halogenated hydrophobic ligand, was conducted using parallel synthesis. NMP and dry beads obtained from previous procedure were placed into a 12 mL test tube. Halogenated hydrophobic ligand solution (20 wt. % in NMP) was then added. The amount of each component was summarized in the table below. The mixture was stirred at 400 rpms with an overhead stirrer for 5 minutes before applying heat to 75° C. for 16 hour. The resulting beads were washed with NMP twice, ethanol twice, 0.5M HCl solution for three times, saturated NaCl solution, and water for three times followed by drying under vacuum.

| Sample # | Hydrophobic ligand | Monomer: Crosslinking Monomer: hydrophobic ligand Ratio | beads (mg) | Hydrophobic ligand (mg) | NMP (mg) |
|---|---|---|---|---|---|
| 85-A1 | 1,12-dibromododecane | 1:1.6:0.5 | 1000 | 99 | 4396 |
| 85-B1 | 1,12-dibromododecane | 1:1.6:1.5 | 1000 | 297 | 5187 |
| 86-A1 | 1-bromodecane | 1:1.6:0.5 | 1000 | 75 | 4300 |
| 86-B1 | 1-bromodecane | 1:1.6:1.5 | 1000 | 225 | 4902 |
| 87-B1 | 1,12-dichlorododecane | 1:1.6:1.5 | 1000 | 216 | 4865 |
| 88-A1 | 1-Chlorooctane | 1:1.6:1 | 1000 | 90 | 4359 |
| 88-B1 | 1-Chlorooctane | 1:1.6:3 | 1000 | 269 | 5076 |

Bile acid binding capacity, affinity, and retention for each resulting polymer were determined via the A assay, B assay and hamster model and results are reported in the table below.

| Sample # | Hydrophobic ligand | Monomer: Crosslinking Monomer: hydrophobic ligand Ratio | BA binding affinity A assay (mmol/g) | BA binding capacity B assay (mmol/g) | BA binding retention Hamster (mmol/g) | % Primary Bile Acid in feces | Swelling (g/g) |
|---|---|---|---|---|---|---|---|
| 85-A1 | 1,12-dibromododecane | 1:1.6:0.5 | 0.58 | 2.7 | | | 8 |
| 85-B1 | 1,12-dibromododecane | 1:1.6:1.5 | 0.6 | 2.6 | 0.46 | 10.7 | 6 |
| 86-A1 | 1-bromodecane | 1:1.6:0.5 | 0.59 | 2.72 | | | 43 |
| 86-B1 | 1-bromodecane | 1:1.6:1.5 | 0.63 | 2.56 | 0.48 | 8.3 | 39 |
| 87-B1 | 1,12-dichlorododecane | 1:1.6:1.5 | 0.59 | 2.61 | 0.38 | 5.9 | 7 |
| 88-A1 | 1-Chlorooctane | 1:1.6:1 | 0.55 | 2.45 | | | 31 |
| 88-B1 | 1-Chlorooctane | 1:1.6:3 | 0.57 | 2.61 | 0.38 | 4.8 | 25 |

Example 42

Synthesis of $C_4$ BTA beads with TMBMP-DBUD (4,4'-(propane-1,3-diyl)bis(1-(11-bromoundecyl)-1-methylpiperidinium))

Synthesis of $C_4$ BTA with TMBMP-DBUD was conducted using parallel synthesis. TMBMP-DBUD (438 mg) was dispensed into a 12 mL glass tube followed by addition of water (1,514 mg) and $C_4$ BTA (100 mg). After mixing $C_4$ BTA with TMBMP-DBUD, DDS (179 mg, 15 wt. % in water) was added. After that, the organic phase of heptane (2,733 mg) and Span 80 solution (2,667 mg, 15 wt. % in heptane) was added. The reaction mixture was stirred with an overhead stirrer at 400 rpm. The vial was capped and heated for 17 hours at 75° C.

Example 43

Synthesis of crosslinked beads of $C_{12}$ BTA beads with TMBMP-DBD (4,4'-(propane-1,3-diyl)bis(1-(10-bromodecyl)-1-methylpiperidinium)

A 250 mL 3-neck round flask equipped with overhead stirrer, condenser and thermometer was charged with $C_{12}$ BTA (1.63 g, 3.8 mmol) and water (14.4 mL). The resulting mixture was stirred in an ice bath for 5 minutes and hydrochloric acid (374 uL, 3.8 mmol, 37 wt. % in water) was added slowly. After the ice bath was removed, dodecylbenzenesulfonic acid sodium salt (2.77 mL, 15 wt. % in water) was then added to the above mixture and stirred for 2 minutes, followed by the addition of 4,4'-(propane-1,3-diyl)bis(1-(10-bromodecyl)-1-methylpiperidinium) (5.09 g, 6.01 mmol) was added. Heptanes (40.8 mL) and Span 80 solution (38.3 mL, 15 wt. % in heptanes) were then added respectively. The final mixture was stirred at 170 rpm with an overhead stirrer and heated in oil bath at 75° C. The internal temperature of the reaction was 75° C. After 16 hours, a Dean-Stark treatment was performed to remove the water using the azeotrope of heptanes and water (at 80° C.); achieved by increasing the temperature of the oil bath to 95° C. The end point of the process was when the temperature of the mixture reached 100° C. or when all the water in the reaction mixture was collected.

The reaction mixture was cooled to ambient temperature, stirring was stopped, and the organic layer was decanted. The beads were washed with two washes with ethanol, two washes with 0.5 M HCl solution, one wash with saturated aqueous NaCl solution, and two washes with water. The beads were vacuum-dried for 48 hours.

| Sample # | Monomer: Crosslinking Monomer Ratio | BA binding affinity A assay (mmol/g) | BA binding capacity B assay (mmol/g) | BA binding retention Hamster (mmol/g) | % Primary Bile Acid in feces | Swelling (g/g) |
|---|---|---|---|---|---|---|
| 89-A1 | 1:1.6 | 0.58 | 2.72 | 0.28 | 3.7 | 33 |

Example 44

Synthesis of Crosslinked Beads of $C_4$ BTA Beads with Dibromodecane Via the Prepolymer Route An Argonaut Advantage Series 3400 Process Chemistry workstation equipped with over head stirrer, reflux condenser, nitrogen inlet port, and Julabo FP88 refrigeration unit was used to prepare prepolymer solution. To the 250 mL reaction flask, 50 g (166.63 mmol) of 1,10-dibromodecane and 50 g ethanol were added. The mixture was heated to 50° C. at 300 rpm to make sure that 1,10-dibromodecane was completely dissolved in ethanol. In a separate 100 mL beaker, 32.965 g (104.14 mmol) of $C_4$ BTA and 32.96 g of ethanol were added to make a 50 wt. % solution of $C_4$ BTA in ethanol. This solution was then added to the 250 mL reaction flask containing 50 wt. % 1,10-dibromodecane solution in ethanol. The reaction was allowed to heat at 50° C. for 90 minutes. The reaction viscosity increased over the time but no gelation occurred. The reaction was cooled for 5 minutes using refrigeration unit. Then hydrochloric acid solution (30.37 mL of 37 wt. % aqueous hydrochloric acid in 65.9 mL deionized water) was added to the reaction mixture to quench the reaction. The reaction mixture was allowed to cool down to room temperature and then ethanol was removed by a rotary evaporator operated at room temperature. The resulting prepolymer solution was then filtered to remove any unreacted 1,10-dibromodecane. The solution was then stored in a 250 mL pyrex glass bottle with cap before next utilization. The percent solid content of the solution was determined by thermogravimetric analysis and was found to be 58 wt. % of prepolymer in water.

Bead synthesis was performed in a 250 mL Argonaut Advantage Series 3400 Process Chemistry workstation equipped with an over head stirrer, a reflux condenser, a nitrogen inlet port, and a Julabo FP88 refrigeration unit. Mineral oil was used as a continuous phase with 10 wt. % Span 80 as a surfactant. To the reactor, 30 g (21.5 mmol) of prepolymer solution (58 wt. % in water) was added. The reaction flask was stirred at 300 rpm and was heated to 50° C. Then 6.98 mL (27.925 mmol) of 4M sodium hydroxide, prepared previously, was added to the reaction flask and allowed to mix for 1 minute. The stirring was stopped and 101.17 mL of mineral oil solution containing 10 wt. % Span 80 was added to the reaction mixture. The stirring was resumed at 300 rpm, the reaction temperature was increased to 60° C. and the reaction was allowed to continue for 17 hours under inert nitrogen atmosphere. The reaction was cooled to room temperature with the help of refrigeration unit. The reaction content was then transferred to a filter frit to remove the excess continuous and discrete phases. Beads thus formed were then washed with 100 mL hexane (2 times), 100 mL ethanol (2 times), 100 mL aqueous hydrochloric acid solution (0.5M), 100 mL 10 vol. % aqueous ammonium hydroxide solution (2 times) and finally 100 mL deionized water (3 times). The beads were then vacuum dried for 48 hours to remove water. The final product weight was 5.2 gm.

Bile acid binding capacity, affinity, and retention for each resulting polymer were determined via the A assay, B assay and hamster model and results are reported in the table below.

| Sample # | BA Binding affinity A assay (mmol/g) | BA Binding capacity B assay (mmol/g) | BA Binding retention Hamster (mmol/g) | % Primary Bile Acid in feces | Swelling (g/g) |
|---|---|---|---|---|---|
| 90-A2 | 0.647 | 3.23 | 0.45 | 15.8 | 0.38 |

Example 45

Solution polymerization of N,N,N',N'-(3-aminopropyl)-diaminododecane-2-methyl-1,3-bis(oxiran-2-ylmethyl)-1H-imidazol-3-ium gel A 40 mL vial equipped with magnetic stirrer was charged with N,N,N',N'-(3-aminopropyl)-diaminododecane (4.0 g, 9.3 mmole) and water (4.7 mL). The mixture was stirred for 5 minutes; 2-methyl-1,3-bis(oxiran-2-ylmethyl)-1H-imidazol-3-ium (3.0 g, 13.1 mmole) was then added. The vial was heated in an oil bath at 70° C. with stirring for 17 hours. A slightly turbid hard gel was obtained. The gel was ground with an ultrasonic mixer for 30 minutes in methanol and then washed with methanol twice, 0.5 M hydrochloric acid once, and water three times.

| Sample # | Monomer | Crosslinker | Monomer/Crosslinker ratio |
|---|---|---|---|
| 91-A1 | Mon4 | Xlin 2 | 1:4 |
| 91-A2 | Mon4 | Xlin 2 | 1:7 |

ABBREVIATION

Mon4: N,N,N',N'-(3-aminopropyl)-diaminododecane
Xlin2: 2-methyl-1,3-bis(oxiran-2-ylmethyl)-1H-imidazol-3-ium having the structure:

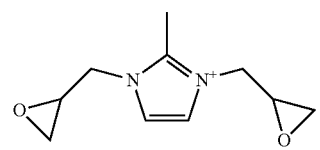

Bile acid binding capacity, affinity, and retention for each resulting polymer were determined via the A assay, B assay and hamster model and results are reported in the table below.

| Sample # | Bile acid binding capacity B assay (mmol/g) | Bile acid binding affinity A assay (mmol/g) | Bile acid retention Hamster (mmol/g) | Swelling (g/g) |
|---|---|---|---|---|
| 91-A1 | 3.07 | 0.58 | 0.40 | 10.68 |
| 91-A2 | 2.98 | 0.61 | 0.43 | 6.1 |

Example 46

Synthesis of Beads from Tris(3-aminopropyl)amine and TMBMP-DBD Crosslinker (Monomer/crosslinker=1/1.2)

A 500 mL three-neck flask equipped with overhead stirrer, condenser was charged with tris(3-aminopropylamine) (3.37 g, 17.9 mmole), water (29.5 mL), acetonitrile (20.3 mL), and dodecylbenzenesulfonic acid sodium salt solution (12.2 mL, 15 wt. % in water). The mixture was stirred for 5 minutes. After homogeneous solution was obtained, TMBMP-DBD (18.00 g, 21.4 mmol) was added. The resulting mixture was stirred for an extra 5 minutes before the addition of heptanes (95.7 mL) and sorbitan oleate (Span 80) solution (90.0 mL, 15 wt. % in heptanes). The final mixture was stirred at ~160 rpm with an overhead stirrer. The external oil was ramped to 75° C. in 1 hour. After 16 hours, a Dean-Stark treatment was performed to remove the acetonitrile and water at 80° C. This was achieved by increasing the temperature of the oil bath to 105° C. The process end point was identified by the temperature of the mixture reaching 95° C. or until all the water in the reaction mixture was collected.

The reaction mixture was allowed to cool to ambient temperature, stirring was stopped and the organic layer was removed by vacuum. The beads were washed with 500 mL 2-propanl twice before collecting by filtration. The beads were vacuum-dried for 24 hours before the post polymerization. Final product isolated was 15.5 g (70% yield).

Example 47

Synthesis of Beads from Tris(3-aminopropyl)amine and TMBMP-DBD Crosslinker (Monomer/crosslinker=1/1.5) (Sample #97-A1)

A 250 mL three-neck flask equipped with overhead stirrer, condenser was charged with tris(3-aminopropylamine) (1.35 g, 7.17 mmole), water (14.5 mL), acetonitrile (9.93 mL), and dodecylbenzenesulfonic acid sodium salt solution (5.93 mL, 15 wt. % in water). The mixture was stirred for 5 minutes. After homogeneous solution was obtained, TMBMP-DBD (9.00 g, 10.7 mmol) was added. The resulting mixture was stirred for an extra 5 minutes before the addition of heptanes (46.8 mL) and sorbitan oleate (Span 80) solution (44.0 mL, 15 wt. % in heptanes). The final mixture was stirred at 150-200 rpm with an overhead stirrer. The external oil was ramped to 75° C. in 1 hour. After 16 hours, a Dean-Stark treatment was performed to remove the acetonitrile and water at 80° C. This was achieved by increasing the temperature of the oil bath to 105° C. The process end point was identified by the temperature of the mixture reaching 95° C. or until all the water in the reaction mixture was collected.

The reaction mixture was allowed to cool to ambient temperature, stirring was stopped and the organic layer was removed by vacuum. The beads were washed with 500 mL 2-propanol twice, saturated sodium carbonate solution twice, saturated sodium chloride twice, and water twice before collecting by filtration. The beads were vacuum-dried for 24 hours before the post polymerization. Final product isolated was 10 g.

Example 48

Synthesis of Beads from Tris(3-aminopropyl)amine and TMBMP-DBD Crosslinker (Monomer/crosslinker=1/2.0) (Sample #98-A1)

A 150 mL three-neck flask equipped with overhead stirrer, condenser was charged with tris(3-aminopropylamine) (0.63 g 3.35 mmole), water (8.86 mL), acetonitrile (6.05 mL), and dodecylbenzenesulfonic acid sodium salt solution (3.56 mL, 15 wt. % in water). The mixture was stirred for 5 minutes. After homogeneous solution was obtained, TMBMP-DBD (5.60 g, 6.68 mmol) was added. The resulting mixture was stirred for an extra 5 minutes before the addition of heptanes (28.5 mL) and sorbitan oleate (Span 80) solution (26.8 mL, 15 wt. % in heptanes). The final mixture was stirred at ~180 rpm with an overhead stirrer. The external oil was ramped to 75° C. in 1 hour. After 16 hours, a Dean-Stark treatment was performed to remove the acetonitrile and water at 80° C. This was achieved by increasing the temperature of the oil bath to 105° C. The process end point was identified by the temperature of the mixture reaching 95° C. or until all the water in the reaction mixture was collected.

The reaction mixture was allowed to cool to ambient temperature, stirring was stopped and the organic layer was removed by vacuum. The beads were washed with hexane twice, ethanol twice, 0.5M HCl solution three times, saturated NaCl solution once, and water three times. The beads were then vacuum-dried for 24 hours.

Example 49

Post Polymerization of Beads Made from Tris(3-Aminopropyl)Amine and TMBMP-DBD with Halogenated Hydrophobic Ligand Post polymerization, a further reaction with halogenated hydrophobic ligand, was conducted using parallel synthesis. NMP or 2-propanol and dry beads obtained from Examples 46-48 above were placed into a 12 mL test tube. Halogenated hydrophobic ligand solution (20 wt. % in NMP) was then added. The amount of each component was summarized in the table below. The mixture was stirred at 400 rpm with an overhead stirrer for 5 minutes before applying heat to 75° C. for 16 hours. The resulting beads were washed with NMP twice, ethanol twice, 0.5M HCl solution three times, saturated NaCl solution once, and water three times followed by drying under vacuum.

| Sample # | Halogenated Hydrophobic ligand | Monomer: Crosslinking Monomer: hydrophobic ligand Ratio | beads (mg) | Hydrophobic ligand (mg) | NMP (mg) | 2-propanol (mg) |
|---|---|---|---|---|---|---|
| 92-A1 | 1,12-dibromo-dodecane | 1:1.2:0.5 | 900 | 124 | 4094 | NA |
| 92-B1 | 1,12-dibromo-dodecane | 1:1.2:1.5 | 900 | 371 | 5083 | NA |
| 93-A1 | 1,12-dibromo-dodecane | 1:1.5:0.5 | 1000 | 113 | 4454 | NA |
| 94-A1 | 1,12-dibromo-dodecane | 1:1.2:1.0 | 1000 | 275 | 5099 | NA |
| 95-A1 | 1,12-dibromo-dodecane | 1:1.2:0.5 | 1000 | 137 | 549 | 4000 |
| 95-B1 | 1,12-dibromo-dodecane | 1:1.2:1.0 | 1000 | 275 | 1099 | 4000 |
| 95-C1 | 1,12-dibromo-dodecane | 1:1.2:1.5 | 1000 | 412 | 1648 | 4000 |
| 96-A1 | 1,12-dibromo-dodecane | 1:1.5:0.5 | 1000 | 139 | 4556 | NA |
| 96-B1 | 1,12-dibromo-dodecane | 1:1.5:1.0 | 1000 | 278 | 5113 | NA |

| Sample # | Halogenated Hydrophobic ligand | Monomer: Crosslinking Monomer: hydrophobic ligand Ratio | Bile acid binding affinity A assay (mmol/g) | Bile acid binding capacity B assay (mmol/g) | Bile acid binding retention Hamster (mmol/g) | Swelling (g/g) |
|---|---|---|---|---|---|---|
| 97-A1 | NA | 1:1.5:0 | 0.48 | 2.31 | 0.23 | 79 |
| 98-A1 | NA | 1:2.0:0 | 0.5 | 2.67 |  | 85 |
| 92-A1 | 1,12-dibromo-dodecane | 1:1.2:0.5 | 0.53 | 2.46 |  | 18 |
| 92-B1 | 1,12-dibromo-dodecane | 1:1.2:1.5 | 0.56 | 2.57 | 0.34 | 14 |
| 93-A1 | 1,12-dibromo-dodecane | 1:1.5:0.5 | 0.57 | 2.56 | 0.38 | 16 |
| 94-A1 | 1,12-dibromo-dodecane | 1:1.2:1.0 | 0.59 | 2.58 | 0.34 | 15 |
| 95-A1 | 1,12-dibromo-dodecane | 1:1.2:0.5 | 0.55 | 2.69 |  | 46 |
| 95-B1 | 1,12-dibromo-dodecane | 1:1.2:1.0 | 0.57 | 2.70 |  | 49 |
| 95-C1 | 1,12-dibromo-dodecane | 1:1.2:1.5 | 0.57 | 2.64 |  | 50 |
| 96-A1 | 1,12-dibromo-dodecane | 1:1.5:0.5 | 0.59 | 2.55 | 0.36 | 11 |
| 96-B1 | 1,12-dibromo-dodecane | 1:1.5:1.0 | 0.62 | 2.51 | 0.38 | 6 |

Example 50

Preparation and bile acid binding study of N,N,N',N'-tetrakis(3-aminopropyl)-1,12-diaminododecane crosslinked with 1.4 mol 1,3-dichloropropanol (Sample 99; S 99)

A 500 mL 3-neck flask equipped with overhead stirrer, condenser, thermometer and an oil bath was charged with N,N,N',N' tetrakis(3-aminopropyl) 1,12 diaminododecane (20.0 g, 46.65 mmole) and water (47.84 mL). The resulting mixture was stirred in an ice-bath for 5 minutes. Hydrochloric acid, 5.06 mL (51.31 mmole, 37 wt % in water), was added slowly over a 10 minute period. The mixture was stirred for an extra 10 minutes in the ice bath before removal. The organic layer was then charged to the reactor as heptane (83.69 mL) followed by sorbitan oleate (Span 80) solution (78.71 ml, 15 wt. % in the heptane). The final mixture was stirred at 200 rpm with an overhead stirrer. The internal temperature of the reaction was raised to 70° C. before starting the addition of 1,3 dichloro-2-propanol (8.42 g, 65.31 mmole) slowly over two hours. Heating then continued for 17 hours. Dean-Stark treatment was subsequently performed to remove the water using the azeotrope of heptane and water (at 80° C.). This was achieved by increasing the temperature of the circulating oil bath to 100° C. for 3 hours and then to 110° C. The process end point was identified by the temperature of the mixture reaching 98° C. or until all the water initially added into the reaction mixture was collected. The reaction mixture was allowed to cool to ambient temperature, stirring was stopped and the organic layer was decanted off.

Sample 99 was subsequently washed to remove excess solvents and impurities as outlined in the table below. The beads were further exposed to HCl to reach a final content of 10.04 wt. % chloride by elemental analysis.

| Solvent | Solvent: beads ratio (gm:gm) | Time (mins) |
|---|---|---|
| Toluene | 6:1 | 20 |
| Methanol | 6:1 | 20 |
| Methanol | 6:1 | 20 |
| Methanol | 6:1 | 20 |

| Solvent | Solvent: beads ratio (gm:gm) | Time (mins) |
|---|---|---|
| 0.5M Hydrochloric Acid | 6:1 | 20 |
| 0.5M Hydrochloric Acid | 6:1 | 20 |
| Water | Excess-Flush until pH 4-5 | |
| 2M Sodium Hydroxide | 6:1 | 20 |
| 2M Sodium Hydroxide | 6:1 | 20 |
| Water | Excess-Flush until pH 6-7 | |
| Methanol | 6:1 | 20 |
| Toluene | 6:1 | 20 |
| Methanol | 6:1 | 20 |
| Water | 4L-flush on the filter | |

Bile acid binding capacity, affinity, and retention for Sample 99 were determined via the A assay, B assay and hamster model and results are reported in the table below, along with swelling ratio and bead size.

| Test Method | Result |
|---|---|
| Malvern Bead Size | d(0.5) = 102.8 um |
| Swelling | 1.2-1.6 g/g |
| B Assay | 3.18 mmol/g |
| A Assay | 0.65 mmol/g |
| Hamster | 0.43 mmol/g |

Additional Polymers Tested.

Five additional polymers known to bind bile acids were tested as comparator substances. Polymer lots and methods of purification are noted in the table below.

| Polymer | Source | Lot # | Purification |
|---|---|---|---|
| Cholestyramine (CT) | Sigma C4650 | 045K0658 | None |
| Colesevelam (CV) | Pharmacy | KB004434 | Purification of API from tablets |
| Colestipol (CP) | Pharmacy | 84RAC | None |
| Sevelamer (SV) | Pharmacy | 8-16-08 | Purification of API from tablets |
| Colestimide (CM) | Pharmacy | KB04438 | Purification of API from tablets |

Preparation of the BES Buffer.

A simple buffer was made consisting of 100 mM BES (N,N-Bis(2-hydroxyethyl)-2-aminoethanesulfonic acid) and 150 mM NaCl at a final pH of 7.0 in 4 L batches. Briefly, 42.65 g of BES (acid), 47.04 g of BES (Na-salt) and 35.06 g of NaCl were dissolved in MilliQ pure water. The volume was adjusted to 4 L and the pH was noted.

Preparation of the Binding Matrices.

On the day preceding the binding assay, a single bile acid was added to 300 ml of BES buffer to a concentration of 20 mM. The solution was allowed to mix 3-6 hours and then subsequently diluted in a series of two fold dilutions. The final dilution set, therefore, contained matrices at 0, 0.31, 0.62, 1.25, 2.5, 5, 10, and 20 mM bile acid. The bile acid and the amount weighed into the BES buffer are listed in the table below.

| Bile Acid | Abbreviation | Amount added (g) |
|---|---|---|
| Cholate | CA | 2.58 |
| Glycocholate | GC | 2.925 |
| Taurocholate | TC | 3.226 |
| Glycodeoxycholate | GDC | 2.829 |
| Taurodeoxycholate | TDC | 3.13 |

Assay Methods.

Polymer samples were dispensed in duplicate into 16×100 mm glass tubes, with each tube containing accurately weighed 8 to 12 mg of dried sample. Binding matrices as described above were dispensed into the sample tubes to give a final concentration of 1 mg test sample per mL of buffer. Control tubes with buffer only were also prepared. The samples were incubated at 37° C. for three hours to reach bile acid binding equilibrium while rotating on a rotisserie platform. Following incubation, the samples were centrifuged at 500×g for 30 minutes to pellet the bile acid binding polymer. The supernatant was collected and transferred to a 0.45 micron Whatman 96-well uniplate to remove small particles prior to analysis. The filtrate was used to determine bile acid concentration as described below. Samples were diluted with BES buffer as needed for a final anticipated concentration of less than 2 mM.

Analytical Methods.

To determine the concentration of bile acid in the isotherm sample, 50 μL of the sample solution was injected onto a HPLC system equipped with Phenomenex Luna C5 column (100 Å, 5 μm, 50×2.00 mm,) and a UV detector. The sample was analyzed using a gradient of 15 mM aqueous phosphate buffer (pH=3) and acetonitrile at a flow rate of 0.4 mL/min. The signal of the bile acid was detected at a wavelength of 205 nm from the UV detector. Calibration solutions comprised of the bile acid standards of different concentrations were also injected onto the same HPLC system. The calibration curve of the bile acid was then constructed by plotting the peak area vs. concentration. Based on the peak area of the bile acid peak found in the sample chromatogram and its calibration curve, the concentration of the bile acid in the sample was calculated.

Data Analysis.

Binding capacity was calculated as $(C_{start}-C_{eq})/1$, where $C_{start}$ (mM) is the starting concentration of bile acid in the binding matrix, $C_{eq}$ (mM) is the concentration of bile acid remaining in the sample at equilibrium after exposure to polymer, and 1 corresponds to the concentration of the bile acid binder (mg/ml). The units for the bound bile acid (e.g., TDC Bnd) and the unbound bile acid (e.g., TDC Unbd) are mmol bile acid/g binder. All assays were run in duplicate with values reported as an average, +/−SD.

| Binder | TDC Star (mM) | TDC Bnd | TDC Unbd | GDC Start (mM) | GDC Bnd | GDC Unbd | TC Start (mM) | TC Bnd | TC Unbd | GC Start (mM) | GC Bnd | GC Unbd | CA Start (mM) | CA Bnd | CA Unbd |
|---|---|---|---|---|---|---|---|---|---|---|---|---|---|---|---|
| CT | 18.94 | 3.26 | 15.68 | 18.57 | 3.05 | 15.53 | 20.42 | 3.29 | 17.14 | 18.17 | 1.80 | 16.37 | 19.63 | 2.85 | 16.78 |
| CT | 9.50 | 3.11 | 6.38 | 9.08 | 2.85 | 6.23 | 10.34 | 2.98 | 7.35 | 9.27 | 1.47 | 7.81 | 10.18 | 2.10 | 8.08 |
| CT | 4.94 | 3.16 | 1.78 | 4.65 | 2.78 | 1.87 | 5.22 | 2.09 | 3.13 | 4.73 | 0.97 | 3.76 | 5.61 | 1.79 | 3.82 |

-continued

| Binder | TDC Start (mM) | TDC Bnd | TDC Unbd | GDC Start (mM) | GDC Bnd | GDC Unbd | TC Start (mM) | TC Bnd | TC Unbd | GC Start (mM) | GC Bnd | GC Unbd | CA Start (mM) | CA Bnd | CA Unbd |
|---|---|---|---|---|---|---|---|---|---|---|---|---|---|---|---|
| CT | 2.56 | 2.20 | 0.36 | 2.36 | 1.75 | 0.60 | 2.64 | 1.07 | 1.57 | 2.42 | 0.60 | 1.82 | 2.68 | 0.91 | 1.78 |
| CT | 1.20 | 1.07 | 0.13 | 1.14 | 0.90 | 0.24 | 1.27 | 0.59 | 0.68 | 1.16 | 0.37 | 0.79 | 1.22 | 0.43 | 0.79 |
| CT | 0.61 | 0.55 | 0.06 | 0.57 | 0.46 | 0.11 | 0.64 | 0.32 | 0.32 | 0.59 | 0.20 | 0.39 | 0.63 | 0.24 | 0.39 |
| CT | 0.31 | 0.28 | 0.03 | 0.29 | 0.23 | 0.06 | 0.32 | 0.17 | 0.16 | 0.30 | 0.10 | 0.20 | 0.31 | 0.11 | 0.20 |
| CT | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CV | 18.94 | 4.45 | 14.50 | 18.57 | 4.16 | 14.41 | 20.42 | 4.44 | 15.98 | 18.17 | 3.62 | 14.55 | 19.63 | 4.84 | 14.80 |
| CV | 9.50 | 4.15 | 5.34 | 9.08 | 4.08 | 5.00 | 10.34 | 4.06 | 6.28 | 9.27 | 2.95 | 6.32 | 10.18 | 4.01 | 6.17 |
| CV | 4.94 | 4.17 | 0.78 | 4.65 | 3.77 | 0.88 | 5.22 | 2.80 | 2.41 | 4.73 | 1.96 | 2.77 | 5.61 | 3.10 | 2.50 |
| CV | 2.56 | 2.40 | 0.16 | 2.36 | 2.12 | 0.24 | 2.64 | 1.42 | 1.22 | 2.42 | 1.13 | 1.29 | 2.68 | 1.61 | 1.07 |
| CV | 1.20 | 1.12 | 0.083 | 1.14 | 1.05 | 0.097 | 1.27 | 0.80 | 0.472 | 1.16 | 0.67 | 0.494 | 1.22 | 0.84 | 0.380 |
| CV | 0.61 | 0.58 | 0.029 | 0.57 | 0.53 | 0.038 | 0.64 | 0.50 | 0.133 | 0.59 | 0.44 | 0.156 | 0.63 | 0.53 | 0.101 |
| CV | 0.31 | 0.308 | 0.000 | 0.29 | 0.288 | 0.000 | 0.32 | 0.324 | 0.000 | 0.30 | 0.261 | 0.037 | 0.31 | 0.313 | 0.000 |
| CV | 0.00 | 0.00 | 0.000 | 0.00 | 0.00 | 0.000 | 0.00 | 0.00 | 0.000 | 0.00 | 0.00 | 0.000 | 0.00 | 0.00 | 0.000 |
| CP | 18.94 | 5.367 | 13.577 | 18.57 | 5.702 | 12.869 | 20.42 | 4.632 | 15.791 | 18.17 | 4.159 | 14.011 | 19.63 | 5.040 | 14.593 |
| CP | 9.50 | 5.098 | 4.397 | 9.08 | 5.025 | 4.056 | 10.34 | 3.874 | 6.462 | 9.27 | 3.183 | 6.092 | 10.18 | 3.976 | 6.203 |
| CP | 4.94 | 4.340 | 0.604 | 4.65 | 3.989 | 0.658 | 5.22 | 1.992 | 3.226 | 4.73 | 1.587 | 3.146 | 5.61 | 2.370 | 3.237 |
| CP | 2.56 | 2.246 | 0.313 | 2.36 | 2.002 | 0.355 | 2.64 | 0.378 | 2.260 | 2.42 | 0.238 | 2.182 | 2.68 | 0.492 | 2.191 |
| CP | 1.20 | 0.893 | 0.309 | 1.14 | 0.819 | 0.324 | 1.27 | 0.029 | 1.243 | 1.16 | 0.026 | 1.138 | 1.22 | 0.012 | 1.205 |
| CP | 0.61 | 0.327 | 0.282 | 0.57 | 0.261 | 0.309 | 0.64 | 0.007 | 0.630 | 0.59 | 0.012 | 0.578 | 0.63 | 0.013 | 0.619 |
| CP | 0.31 | 0.049 | 0.258 | 0.29 | 0.022 | 0.266 | 0.32 | 0.007 | 0.317 | 0.30 | 0.005 | 0.293 | 0.31 | −0.011 | 0.324 |
| CP | 0.00 | 0.000 | 0.000 | 0.00 | 0.000 | 0.000 | 0.00 | 0.000 | 0.000 | 0.00 | 0.000 | 0.000 | 0.00 | 0.000 | 0.000 |
| SV | 18.94 | 7.748 | 11.196 | 18.57 | 7.523 | 11.049 | 20.42 | 6.626 | 13.797 | 18.17 | 7.781 | 10.390 | 19.63 | 8.169 | 11.464 |
| SV | 9.50 | 7.648 | 1.848 | 9.08 | 7.297 | 1.784 | 10.34 | 6.714 | 3.622 | 9.27 | 5.722 | 3.553 | 10.18 | 6.505 | 3.675 |
| SV | 4.94 | 4.769 | 0.175 | 4.65 | 4.489 | 0.157 | 5.22 | 3.480 | 1.738 | 4.73 | 3.033 | 1.700 | 5.61 | 2.970 | 2.637 |
| SV | 2.56 | 2.411 | 0.147 | 2.36 | 2.215 | 0.142 | 2.64 | 1.030 | 1.608 | 2.42 | 0.939 | 1.481 | 2.68 | 1.018 | 1.665 |
| SV | 1.20 | 1.059 | 0.144 | 1.14 | 1.004 | 0.139 | 1.27 | 0.110 | 1.163 | 1.16 | 0.100 | 1.065 | 1.22 | 0.062 | 1.156 |
| SV | 0.61 | 0.466 | 0.143 | 0.57 | 0.435 | 0.135 | 0.64 | 0.029 | 0.608 | 0.59 | 0.029 | 0.562 | 0.63 | 0.032 | 0.600 |
| SV | 0.31 | 0.173 | 0.135 | 0.29 | 0.160 | 0.129 | 0.32 | 0.016 | 0.307 | 0.30 | 0.012 | 0.287 | 0.31 | 0.001 | 0.312 |
| SV | 0.00 | 0.000 | 0.000 | 0.00 | 0.000 | 0.000 | 0.00 | 0.000 | 0.000 | 0.00 | 0.000 | 0.000 | 0.00 | 0.000 | 0.000 |
| S 99 | 18.94 | 7.181 | 11.763 | 18.57 | 7.022 | 11.549 | 20.42 | 6.626 | 13.797 | 18.17 | 5.559 | 12.611 | 19.63 | 7.338 | 12.295 |
| S 99 | 9.50 | 6.867 | 2.628 | 9.08 | 6.880 | 2.201 | 10.34 | 5.537 | 4.799 | 9.27 | 4.674 | 4.601 | 10.18 | 5.843 | 4.337 |
| S 99 | 4.94 | 4.729 | 0.216 | 4.65 | 4.445 | 0.202 | 5.22 | 3.563 | 1.655 | 4.73 | 3.168 | 1.565 | 5.61 | 4.432 | 1.175 |
| S 99 | 2.56 | 2.478 | 0.081 | 2.36 | 2.283 | 0.074 | 2.64 | 1.890 | 0.748 | 2.42 | 1.679 | 0.741 | 2.68 | 2.106 | 0.577 |
| S 99 | 1.20 | 1.144 | 0.058 | 1.14 | 1.090 | 0.052 | 1.27 | 0.831 | 0.441 | 1.16 | 0.734 | 0.430 | 1.22 | 0.888 | 0.329 |
| S 99 | 0.61 | 0.564 | 0.045 | 0.57 | 0.531 | 0.039 | 0.64 | 0.374 | 0.263 | 0.59 | 0.334 | 0.256 | 0.63 | 0.425 | 0.207 |
| S 99 | 0.31 | 0.274 | 0.034 | 0.29 | 0.260 | 0.028 | 0.32 | 0.171 | 0.153 | 0.30 | 0.148 | 0.151 | 0.31 | 0.186 | 0.127 |
| S 99 | 0.00 | 0.000 | 0.000 | 0.00 | 0.000 | 0.000 | 0.00 | 0.000 | 0.000 | 0.00 | 0.000 | 0.000 | 0.00 | 0.000 | 0.000 |
| CM | 18.94 | 5.391 | 13.552 | 18.57 | 5.225 | 13.346 | 20.42 | 4.941 | 15.482 | | | | 19.63 | 4.663 | 14.969 |
| CM | 9.50 | 5.068 | 4.427 | 9.08 | 4.798 | 4.283 | 10.34 | 4.194 | 6.141 | | | | 10.18 | 3.281 | 6.898 |
| CM | 4.94 | 4.376 | 0.569 | 4.65 | 3.858 | 0.789 | 5.22 | 2.120 | 3.097 | | | | 5.61 | 1.567 | 4.040 |
| CM | 2.56 | 2.250 | 0.309 | 2.36 | 1.819 | 0.538 | 2.64 | 0.306 | 2.332 | | | | 2.68 | 0.375 | 2.309 |
| CM | 1.20 | 0.905 | 0.297 | 1.14 | 0.675 | 0.467 | 1.27 | 0.029 | 1.244 | | | | 1.22 | 0.007 | 1.210 |
| CM | 0.61 | 0.324 | 0.285 | 0.57 | 0.127 | 0.443 | 0.64 | 0.008 | 0.630 | | | | 0.63 | 0.014 | 0.618 |
| CM | 0.31 | 0.043 | 0.265 | 0.29 | 0.009 | 0.280 | 0.32 | 0.004 | 0.320 | | | | 0.31 | −0.009 | 0.322 |
| CM | 0.00 | 0.000 | 0.000 | 0.00 | 0.000 | 0.000 | 0.00 | 0.000 | 0.000 | | | | 0.00 | 0.000 | 0.000 |

Data was graphically represented in an isotherm format in which Bound Bile Acid (mmol bile acid/g polymer) was plotted vs Unbound Bile Acid (mmol bile acid/g polymer). (FIGS. 1 and 2). Unbound Bile Acid is calculated as Ceq (mM)/1 mg/ml polymer. Bound Bile Acid is calculated as Cstart−Ceq/1 mg/ml polymer.

In view of the above, it will be seen that the several objects of the invention are achieved and other advantageous results attained. As various changes could be made in the above polymers, pharmaceutical compositions, and methods of treatment without departing from the scope of the invention, it is intended that all matter contained in the above description and shown in the accompanying drawing[s] shall be interpreted as illustrative and not in a limiting sense.

What is claimed is:

1. An amine polymer comprising the reaction product of an amine monomer having six, seven or eight possible reaction sites and a crosslinking monomer, wherein units of the polymer have the structure of formula 1

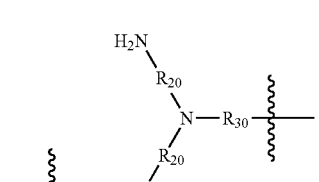

(1)

wherein $R_{10}$ is derived from the crosslinking monomer and is $C_2$ to $C_{16}$ alkylene, —NH—C(NH)—NH—, —NH—C(NH$_2{}^+$)—NH—, or $C_2$ to $C_{50}$ alkylene wherein one or more of the —CH$_2$— groups of the alkylene group is replaced with an amide, a carbonyl, an ether, an ester, a cycloalkyl, or a heterocyclo functional group, or one or more of the —CH$_2$— groups of the alkylene group is substituted with hydroxy;

$R_{30}$ is derived from the amine monomer and is $C_2$ to $C_{12}$ alkylene, arylene, diformylheterocyclo, or $C_2$ to $C_{12}$ alkylene wherein one or more of the —CH$_2$— groups of the alkylene group is replaced with an amide, a carbonyl, a cycloalkyl, an aryl, or a heterocyclo functional group;

each $R_{20}$ is independently $C_2$ to $C_6$ alkylene or $C_2$ to $C_6$ alkylene wherein one or more of the —$CH_2$— groups of the alkylene group is replaced with an amide functional group; and at least one of $R_{10}$ or $R_{30}$ is a hydrophobic group having a calculated log P (c Log P) of greater than 4.

2. The amine polymer of claim 1
wherein
$R_{10}$ is derived from the crosslinking monomer and is $C_2$ to $C_{16}$ alkylene, —NH—C(NH)—NH—, —NH—C(NH$_2^+$)—NH—, or $C_2$ to $C_{50}$ alkylene wherein one or more of the —$CH_2$— groups of the alkylene group is replaced with an amide, a carbonyl, an ether, an ester, a cycloalkyl, or a heterocyclo functional group, or one or more of the —$CH_2$— groups of the alkylene group is substituted with hydroxy;

$R_{30}$ is derived from the amine monomer and is $C_2$ to $C_6$ alkylene;

each $R_{20}$ is independently $C_2$ to $C_6$ alkylene or $C_2$ to $C_6$ alkylene wherein one or more of the —$CH_2$— groups of the alkylene group is replaced with an amide functional group; and $R_{10}$ is a hydrophobic group having a calculated log P (c Log P) of greater than 4.

3. The amine polymer of claim 1
wherein
$R_{10}$ is derived from the crosslinking monomer and is $C_8$ to $C_{16}$ alkylene, or $C_8$ to $C_{50}$ alkylene wherein one or more of the —$CH_2$— groups of the alkylene group is replaced with an amide, a carbonyl, an ether, an ester, a cycloalkyl, an aryl, or a heterocyclo functional group;

$R_{30}$ is derived from the amine monomer and is $C_2$ to $C_{12}$ alkylene, arylene, diformylheterocyclo, or $C_2$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; and each $R_{20}$ is independently $C_2$ to $C_6$ alkylene or $C_2$ to $C_6$ alkylene wherein one or more of the —$CH_2$— groups of the alkylene group is replaced with an amide functional group.

4. The amine polymer of claim 1, comprising repeat units derived from polymerization of an amine monomer and a crosslinking monomer, wherein the amine monomer is an amine of formula 2 having the structure:

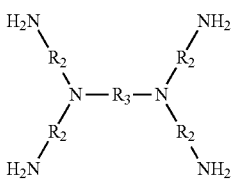

(2)

wherein each $R_2$ is independently $C_2$ to $C_8$ alkylene or $C_2$ to $C_8$ alkylene wherein one or more of the —$CH_2$— groups of the alkylene group is replaced with at least one amide functional group, and either (i) $R_3$ is $C_2$ to $C_{12}$ alkylene, arylene, diformylheterocyclo, or $C_2$ to $C_8$ alkylene wherein one or more of the —$CH_2$— groups of the alkylene group is replaced with an amide, a carbonyl, an ether, an ester, a cycloalkyl, an aryl, or a heterocyclo functional group; and the crosslinking monomer is guanidine, a guanidinium salt, a compound having the formula X—$R_1$—X, or a combination thereof, wherein each X is independently a leaving group, $R_1$ is $C_8$ to $C_{16}$ alkylene, dimethylbiphenyl, or 1,3-bis(m-haloC$_m$alkyl)-1H-imidazol-3-ium, 4,4'-(C$_x$alkane-1,x-diyl)bis(1-(m-haloC$_m$alkyl)-1-methylpiperidinium), or 1-(q-haloC$_q$alkyl)-3-(m-(3-(p-haloC$_p$alkyl)-1H-imidazol-3-ium-1-yl)C$_m$alkyl-1H-imidazol-3-ium, wherein m is an integer from 2 to 14, p is an integer from 2 to 14, q is an integer from 2 to 14, and x is an integer from 2 to 8; or (ii) $R_3$ is $C_8$ to $C_{16}$ alkylene, and the crosslinking monomer is a compound having the formula X—$R_1$—X, wherein each X is independently a leaving group, $R_1$ is $C_2$ to $C_6$ alkylene or $C_2$ to $C_6$ alkylene wherein one or more of the —$CH_2$— groups of the alkylene group is replaced with an amide, a carbonyl, an ether, an ester, a cycloalkyl, an awl, or a heterocyclo functional group, or one or more of the —$CH_2$— groups of the alkylene group is substituted with hydroxy.

5. The amine polymer of claim 4
wherein each $R_2$ is independently $C_2$ to $C_8$ alkylene or $C_2$ to $C_8$ alkylene wherein one or more of the —$CH_2$— groups of the alkylene group is replaced with an amide functional group; and $R_3$ is $C_2$ to $C_{12}$ alkylene, arylene, diformylheterocyclo, or $C_2$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; and a portion of the nitrogen atoms of the amine polymer are substituted with a ligand selected from aminoalkyl, aryl, arylalkyl, oxoalkyl, cycloalkyl, (cycloalkyl)alkyl, guanidino, heterocyclo, heterocycloalkyl, (trialkylammonio)alkyl, 2-(protected amino)-m-(heterocyclo)-1-oxoC$_m$alkyl, 2-(protected amino)-1-oxoC$_m$alkyl, 2-(protected amino)-3-methyl-1-oxoC$_m$alkyl, 2-(protected amino)-4-methyl-1-oxoC$_m$alkyl, 2-(protected amino)-1-oxo-m-arylC$_m$alkyl, 2-(protected amino)-m-(alkylthio)-1-oxoC$_m$alkyl, 2-(protected amino)-m-(aryl)-1-oxoC$_m$alkyl, 2-(protected amino)-m-carboxy-1-oxoC$_m$alkyl, 2-(protected amino)-m-guanidino-1-oxoC$_m$alkyl, 2-(protected amino)-(m−1)-hydroxy-1-oxoC$_m$alkyl, 2-(protected amino)-m-hydroxy-1-oxoC$_m$alkyl, 2-(protected amino)-m-mercapto-1-oxoC$_m$alkyl, m-(alkylamino)-m-oxoC$_m$alkyl, m-(alkylheterocyclo)C$_m$alkyl, m-amino-2-(protected amino)-1-oxoC$_m$alkyl, m-amino-2-(protected amino)-1,m-dioxoC$_m$alkyl, m-(x-aminoC$_x$alkyl)heterocyclo C$_m$alkyl, (m−1)-amino-m-(heterocyclo)-1-oxoC$_m$alkyl, m-(arylalkylamino)-m-oxoC$_m$alkyl, m-(x-(alkylthio)C$_x$alkylamino)-m-oxoC$_m$alkyl, m-(x-aminoC$_x$alkylamino)-m-oxoC$_m$alkyl, m-(x-amino-x-oxoC$_x$alkylamino)-m-oxoC$_m$alkyl, m-(x-carboxyC$_x$alkylamino)-m-oxoC$_m$alkyl, m-(heterocycloalkylamino)-m-oxoC$_m$alkyl, m-(x-hydroxyC$_x$alkylamino)-m-oxoC$_m$alkyl, m-((x−1)-hydroxyC$_x$alkylamino)-m-oxoC$_m$alkyl, m-(x-mercaptoC$_x$alkylamino)-m-oxoC$_m$alkyl, m-(x-trialkylammonioC$_x$alkyl)heterocycloC$_m$alkyl, m-(x-(2-(alkoxy)benzamido)C$_x$alkylamino)-m-oxoC$_m$alkyl, m-(x-(3-(alkoxy)

benzamido)$C_x$alkylamino)-m-oxo$C_m$alkyl, m-(x-(4-(alkoxy)benzamido)$C_x$alkylamino)-m-oxo$C_m$alkyl, a ligand of formula 4

  (4)

or a combination thereof, wherein $R_{46}$ is $C_6$ to $C_{16}$ alkylene, $R_{47}$ is 1,y-bis(1-methylpiperidin-4-yl)$C_y$alkylene, $R_{48}$ is $C_6$ to $C_{16}$ alkyl, m is an integer from 3 to 12, x is an integer from 1 to 12, y is an integer from 1 to 14, and z is an integer from 1 to 16.

6. The amine polymer of claim 1 wherein $R_{10}$ is $C_2$ to $C_6$ alkylene wherein one or more of the —$CH_2$— groups of the alkylene group is substituted with hydroxy.

7. The amine polymer of claim 6 wherein $R_{10}$ is —$CH_2$—CH(OH)—$CH_2$—.

8. The amine polymer of claim 7 wherein $R_{30}$ is decylene.

9. The amine polymer of claim 7 wherein $R_{30}$ is dodecylene.

10. The amine polymer of claim 1 wherein the binding affinity for bile acids is at least about 0.46 mmol/g when measured using an in vitro A assay,
   wherein the in vitro binding affinity for bile salts is determined under conditions that are intended to mimic in certain respects those conditions found in the lower small intestine, and wherein the amine polymer is analyzed using assay A (protocol 1) that combines the polymer to be analyzed in a desired concentration with a solution that mimics certain conditions present in the lower small intestine, after a period of time, the polymers are recovered by centrifugation and the supernatants are sampled, filtered to remove any remaining particulates and assayed for ion concentrations by liquid chromatography (LC), and wherein by comparing the equilibrium concentrations of glycocholate ($GC_{eq}$), glycodeoxycholate ($GDC_{eq}$), oleyl glycerol ($OG_{eq}$) and/or oleic acid ($OA_{eq}$) in the presence of the polymer to their concentrations in test solution in the absence of the polymer, the amount of each component bound under these experimental conditions in mmoles/g polymer is calculated.

11. The amine polymer of claim 1 wherein the binding capacity for bile acids is at least about 2.22 mmol/g when measured using the B assay,
   wherein the in vitro binding capacity for bile salts is determined under conditions that are intended to mimic in certain respects those conditions found in the upper small intestine after a meal, the amine polymer is analyzed using Assay B (protocol 2) in that the polymer to be analyzed is combined in a desired concentration with a solution that mimics certain conditions present in the upper small intestine, after a period of time, the polymers are recovered by centrifugation and the supernatants are sampled, filtered to remove any remaining particulates and assayed for ion concentrations by liquid chromatography (LC), and wherein by comparing the equilibrium concentrations of glycocholate ($GC_{eq}$), glycodeoxycholate ($GDC_{eq}$), oleyl glycerol ($OG_{eq}$) and/or oleic acid ($OA_{eq}$) in the presence of the polymer to their concentrations in test solution in the absence of the polymer, the amount of each component bound under these experimental conditions in mmoles/g polymer is calculated.

12. The amine polymer of claim 1 wherein the amine polymer is derived from the polymerization of an amine monomer and a crosslinking monomer wherein the amine monomer comprises N,N,N',N'-tetrakis(3-aminopropyl)-1,12-diaminododecane and the crosslinking monomer comprises 1,3-dichloropropanol.

13. A method of reducing serum LDL-cholesterol in an animal subject comprising administering an effective amount of an amine polymer of claim 1 to an animal subject in need thereof.

14. The method of claim 13 further comprising administering an agent that treats dyslipidemia to an animal subject.

15. The method of claim 14 wherein the agent that treats dyslipidemia is a hydroxymethyl-glutaryl-coenzyme A (HMG CoA) reductase inhibitor, a fibrate, a cholesterol absorption inhibitor, niacin (i.e. nicotinic acid or derivatives thereof), a phytosterol, an intestinal lipase inhibitor, an intestinal or secreted phospholipase A2 inhibitor, inhibitors of the synthesis or normal activity of Apo-B100, agonists of the synthesis or normal activity of ApoA, or any agent that modulates cholesterol absorption or metabolism, or a combination thereof to the animal subject.

16. The method of claim 15 wherein the agent that treats dyslipidemia is a HMG CoA reductase inhibitor, the HMG CoA reductase inhibitor comprising a statin selected from the group consisting of atorvastatin, cerivastatin, fluvastatin, lovastatin, mevastatin, pitavastatin, pravastatin, rosuvastatin, simvastatin, and a combination thereof.

17. The method of claim 15 wherein the agent that treats dyslipidemia is a fibrate, the fibrate comprising benzafibrate, ciprofibrate, clofibrate, gemfibrozil, fenofibrate, or a combination thereof.

* * * * *